United States Patent
Sugimoto et al.

(10) Patent No.: US 11,193,162 B2
(45) Date of Patent: Dec. 7, 2021

(54) NUCLEIC ACID DETECTION OR QUANTIFICATION METHOD USING MASK OLIGONUCLEOTIDE, AND DEVICE FOR SAME

(71) Applicant: Fuso Pharmaceutical Industries, Ltd., Osaka (JP)

(72) Inventors: Norihiko Sugimoto, Osaka (JP); Souji Eda, Osaka (JP); Masahiro Asakura, Osaka (JP); Kanako Abe, Okaka (JP); Hirotsugu Uehara, Osaka (JP); Kazumasa Kamei, Osaka (JP); Yoshihiko Uesaka, Ibaraki (JP); Yuichi Oku, Ibaraki (JP); Yusuke Shibahara, Ibaraki (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 203 days.

(21) Appl. No.: 15/116,503

(22) PCT Filed: Jan. 29, 2015

(86) PCT No.: PCT/JP2015/052501
§ 371 (c)(1),
(2) Date: Aug. 3, 2016

(87) PCT Pub. No.: WO2015/119035
PCT Pub. Date: Aug. 13, 2015

(65) Prior Publication Data
US 2017/0037457 A1 Feb. 9, 2017

(30) Foreign Application Priority Data
Feb. 5, 2014 (JP) .............................. JP2014-020183

(51) Int. Cl.
*C12Q 1/68* (2018.01)
*C12Q 1/6832* (2018.01)

(52) U.S. Cl.
CPC ................................. *C12Q 1/6832* (2013.01)

(58) Field of Classification Search
USPC ...... 435/6.1, 6.11, 91.1, 283.1, 287.1, 287.2; 436/94, 501; 536/23.1, 24.3, 24.33
See application file for complete search history.

(56) References Cited

U.S. PATENT DOCUMENTS

| | | | |
|---|---|---|---|
| 6,037,127 A | 3/2000 | Ebersole et al. | |
| 2003/0073073 A1* | 4/2003 | Wolde-Mariam | .... G01N 33/558 435/5 |

(Continued)

FOREIGN PATENT DOCUMENTS

| | | |
|---|---|---|
| CN | 1498275 A | 5/2004 |
| EP | 0357011 A2 | 3/1990 |

(Continued)

OTHER PUBLICATIONS

Rohrman et al., A Lateral Flow Assay for Quantitative Detection of Amplified HIV-1 RNA. PLOS One, 7, e45611, Sep. 2012.*

(Continued)

*Primary Examiner* — Frank W Lu
(74) *Attorney, Agent, or Firm* — Schwegman Lundberg & Woessner, P.A.

(57) ABSTRACT

Very simple, highly sensitive detection or quantification of target nucleic acids of interest has been achieved by: hybridizing mask oligonucleotides to regions in a single-stranded region of a nucleic acid to be assayed between which a region to be hybridized by an oligonucleotide probe is positioned, thereby opening the probe-hybridizing region and keeping the single-stranded region of the target nucleic (Continued)

acid stable, and then subjecting this nucleic acid having the single-stranded region to nucleic acid chromatography.

18 Claims, 34 Drawing Sheets

Specification includes a Sequence Listing.

(56) References Cited

U.S. PATENT DOCUMENTS

| | | | | |
|---|---|---|---|---|
| 2004/0110167 | A1* | 6/2004 | Gerdes | C12Q 1/6834 435/6.11 |
| 2005/0136412 | A1* | 6/2005 | Gingeras | B82Y 5/00 435/6.16 |
| 2006/0094005 | A1* | 5/2006 | Lee | C12Q 1/6834 435/6.11 |

FOREIGN PATENT DOCUMENTS

| | | |
|---|---|---|
| EP | 0698792 A1 | 2/1996 |
| EP | 2644699 A1 | 10/2013 |
| JP | H02-502250 | 7/1990 |
| JP | H0775599 | 3/1995 |
| JP | 2820749 | 8/1998 |
| JP | H10-253632 A | 9/1998 |
| JP | 3001906 B | 11/1999 |
| JP | 3197277 B | 6/2001 |
| JP | 2004-502464 A | 1/2004 |
| JP | 2006-201062 A | 8/2006 |
| WO | WO-89/04876 A1 | 6/1989 |
| WO | WO-02/04122 A2 | 1/2002 |
| WO | WO-02/04668 A2 | 1/2002 |
| WO | WO-2008/084888 A1 | 7/2008 |
| WO | WO-2008/105814 A2 | 9/2008 |
| WO | WO-2012/070618 A1 | 5/2012 |

OTHER PUBLICATIONS

Carter, D.J., et al., "Lateral Flow Microarrays: A Novel Platform for Rapid Nucleic Acid Detection Based on Miniaturized Lateral Flow Chromatography", Nucleic Acids Research, 35, (2007), 11 pgs.

Wei, J., et al., "Miniaturized Paper-Based Gene Sensor for Rapid and Sensitive Identification of Contagious Plant Virus", ACS Appl. Mater. Interfaces, 6, (2014), 22577-22584.

International Patent Application No. PCT/JP2015/052501, International Preliminary Report on Patentability dated Apr. 14, 2015, 9 pgs.

Barken, K.B., et al., "Effect of unlabeled helper probes on detection of an RNA target by bead-based sandwich hybridization", BioTechniques, 36, (Jan. 2004), 124-132.

Fuchs, B.M., et al., "Unlabeled Helper Oligonucleotides Increase the In Situ Accessibility to 16S rRNA of Fluorescently Labeled Oligonucleotide Probes", Applied and Environmental Microbiology, 66, (Aug. 2000), 3603-3607.

Metfies, K., et al., "Electrochemical detection of the toxic dinoflagellate Alexandrium ostenfeldii with a DNA-biosensor", Biosensors and Bioelectronics, 20, (2005), 1349-1357.

Thieme, D., et al., "Sandwich Hybridization Assay for Sensitive Detection of Dynamic Changes in mRNA Transcript Levels in Crude *Escherichia coli* Cell Extracts in Response to Copper Ions", Applied and Environmental Microbiology, 74, (Dec. 2008), 7463-7470.

Imahori, "Denaturation of nucleic acid", Seikagaku Jiten (Biochemistry dictionary), 3rd Ed., p. 280, (1998), w/ English Translation, 5 pgs.

Ujiiye, Takeshi, "A Simple Genetic Testing Tool 'Nucleic Acid Chromatography'", Japanese Journal of Clinical Chemistry, 36(1):19-24, (2007), w/ English Translation, 16 pgs.

* cited by examiner

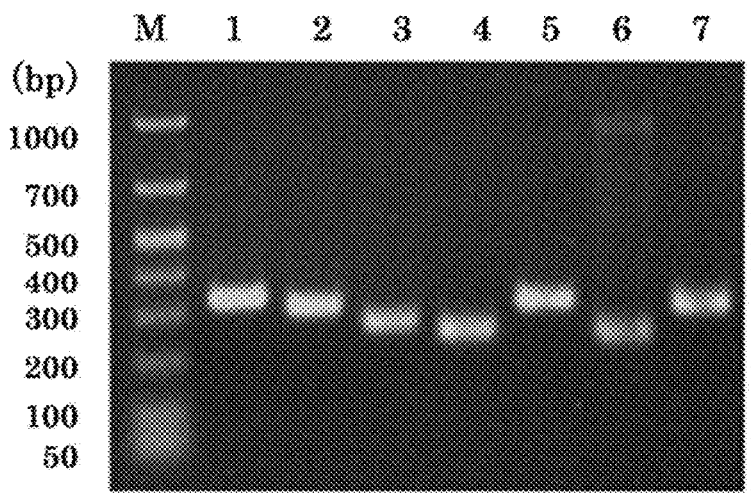

Lane 1: Detection of *Staphylococcus aureus* using the SA1F and SA1R primers.
Lane 2: Detection of *Staphylococcus epidermidis* using the SE1F and SE1R primers.
Lane 3: Detection of *Pseudomonas aeruginosa* using the PA1F and PA1R primers.
Lane 4: Detection of *Enterococcus faecalis* using the EF1F and EF1R primers.
Lane 5: Detection of *Escherichia coli* using the EC1F and EC1R primers.
Lane 6: Detection of *Enterobacter cloacae* using the ET1F and ET1R primers.
Lane 7: Detection of *Klebsiella pneumoniae* using the KP1F and KP1R primers.

Fig. 6

Hybridization of genomic DNA by nucleic acid chromatography

Lane 1: *Enterobacter cloacae*-derived DNA in the presence of mask oligonucleotides (ET)
Lane 2: *Enterobacter cloacae*-derived DNA in the absence of mask oligonucleotides
Lane 2: *Escherichia coli*-derived DNA in the presence of mask oligonucleotides (ET)
Arrow: probe reaction band A. Multiplex PCR of *Campylobacter jejuni*, *C. coli*, and *C. fetus* based on the cdtC gene Lane 1: *C. jejuni* (ATCC700819 strain), Lane 2: *C. jejuni* (81-176 strain), Lane 3: *C. coli* (ATCC33559 strain)
Lane 4: *C. coli* (ATCC43478 strain), Lane 5: *C. fetus* (ATCC27374 strain), Lane 6: *C. fetus* (ATCC19438 strain)
Lane 7: *C. hyointestinalis* (ATCC35217 strain), Lane 8: *C. lari* (ATCC43675),
Lane 9: *C. upsaliensis* (ATCC43956 strain), Lane 10: *E. coli* (C600 strain), M: φX174 *HaeIII* marker B. Bacterial strain-specific detection by multiplex PCR-nucleic acid chromatography Lane 1: C. jejuni (ATCC700819strain), Lane 2: C. jejuni (81-176strain), Lane 3: C. coli (ATCC33559strain)
Lane 4: C. coli (ATCC43478strain), Lane 5: C. fetus (ATCC27374strain), Lane 6: C. fetus (ATCC19438strain)
Lane 7: C. hyointestinalis (ATCC35217strain), Lane 8: C. lari (ATCC43675),
Lane 9: C. upsaliensis (ATCC43956strain), Lane 10: E. coli (C600strain), M: φX174 HaeIII marker Effects of mask oligonucleotides on EC-derived PCR products Lane 1 : Absence of mask oligonucleotides
Lane 2 : ECC3+ECC4
Lane 3 : ECC4
Lane 4 : CT7+CT8

Optimal mask oligonucleotide regions in nucleic acid chromatography

Lane 1 : Absence of mask oligonucleotides
Lane 2 : Presence of mask oligonucleotides for detection oligonucleotide (R2')
Lane 3 : Presence of mask oligonucleotides for capture oligonucleotide (R1')
Lane 4 : Presence of mask oligonucleotides for detection (R2') and capture (R1') oligonucleotides Correlation between the coloring intensity and amount of PCR products in nucleic acid chromatography using mask oligonucleotides Lane 1: Detection of human β-globin using the GM1F and GM1R primers
Lane 2: Detection of E. coli using the EC2F and EC2R primers

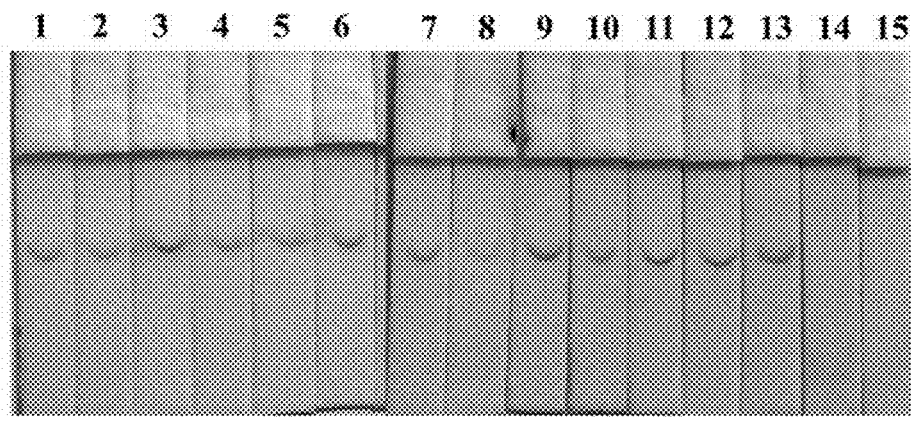

Detection of bacteria by nucleic acid chromatography based on 16S rRNA (excerpt)

Lane 1: *Staphylococcus aureus*(ATCC 12600strain), Lane 2: *Staphylococcus epidermidis*(ATCC 14990strain)
Lane 3: *Pseudomonas aeruginosa*(ATCC 10145strain), Lane 4: *Enterococcus faecalis*(ATCC 19433strain)
Lane 5: *Escherichia coli*(ATCC 11775 strain), Lane 6: *Enterobacter cloacae*(JCM 1232 strain)
Lane 7: *Campylobacter jejuni*(ATCC700819strain), Lane 8: *Eggerthella lenta*(JCM 9979strain)
Lane 9: *Corynebacterium diphtheriae*(JCM1310strain), Lane10: *Corynebacterium jeikeium*(JCM 9384 strain)
Lane 11: *Micrococcus luteus*(JCM 1464strain), Lane 12: *Propionibacterium acnes* (JCM 6425strain)
Lane 13: *Gardnerella vaginalis*(JCM 11026strain), Lane 14: *Candida albicans* (IFO 1385strain)
Lane 15: Negative Control

Fig. 16

PCR for *Candida* strains based on the ITS region

Lane M: BioMarker Low
Lane 1: *C. albicans* (NBRC1385 strain), Lane 2: *C. glabrata* (NBRC0005 strain)
Lane 3: *C. guilliermondii* (NBRC0566 strain), Lane 4: *C. kefyr* (NBRC0586 strain)
Lane 5: *C. krusei* (NBRC0011 strain), Lane 6: *C. lusitaniae* (ATCC66035 strain)
Lane 7: *C. metapsilosis* (NBRC0640 strain), Lane 8: *C. parapsilosis* (NBRC1396 strain)
Lane 9: *C. tropicalis* (NBRC1400 strain)

```
                        SEQUENCE LISTING

<160> NUMBER OF SEQ ID NOS: 137

<210> SEQ ID NO 1
<211> LENGTH: 30
<212> TYPE: DNA
<213> ORGANISM: Artificial sequence
<220> FEATURE:
<223> OTHER INFORMATION: An artificially synthesized oligonucleotide
      sequence

<400> SEQUENCE: 1
ggattcaatg tcacatgagc gtgataaaat                                          30

<210> SEQ ID NO 2
<211> LENGTH: 31
<212> TYPE: DNA
<213> ORGANISM: Artificial sequence
<220> FEATURE:
<223> OTHER INFORMATION: An artificially synthesized oligonucleotide
      sequence

<400> SEQUENCE: 2
aaagctcaag gatatgcgat tactgaagca g                                        31

<210> SEQ ID NO 3
<211> LENGTH: 28
<212> TYPE: DNA
<213> ORGANISM: Artificial sequence
<220> FEATURE:
<223> OTHER INFORMATION: An artificially synthesized oligonucleotide
      sequence

<400> SEQUENCE: 3
tcagaggtca tggaaaatct tcacgaac                                            28

<210> SEQ ID NO 4
<211> LENGTH: 35
<212> TYPE: DNA
<213> ORGANISM: Artificial sequence
<220> FEATURE:
<223> OTHER INFORMATION: An artificially synthesized oligonucleotide
      sequence

<400> SEQUENCE: 4
attgcctcag atttattaaa gcctgctaat tcttc                                    35

<210> SEQ ID NO 5
<211> LENGTH: 24
<212> TYPE: DNA
<213> ORGANISM: Artificial sequence
<220> FEATURE:
<223> OTHER INFORMATION: An artificially synthesized oligonucleotide
      sequence

<400> SEQUENCE: 5
aagatcggcg tattcatcgg cgtc                                                24
```

<210> SEQ ID NO 6
<211> LENGTH: 29
<212> TYPE: DNA
<213> ORGANISM: Artificial sequence
<220> FEATURE:
<223> OTHER INFORMATION: An artificially synthesized oligonucleotide
      sequence

<400> SEQUENCE: 6
cccaggtcct gatagaccag ttgataccc                              29

<210> SEQ ID NO 7
<211> LENGTH: 31
<212> TYPE: DNA
<213> ORGANISM: Artificial sequence
<220> FEATURE:
<223> OTHER INFORMATION: An artificially synthesized oligonucleotide
      sequence

<400> SEQUENCE: 7
gaagacaacg atttatgttt acgctttggc a                           31

<210> SEQ ID NO 8
<211> LENGTH: 27
<212> TYPE: DNA
<213> ORGANISM: Artificial sequence
<220> FEATURE:
<223> OTHER INFORMATION: An artificially synthesized oligonucleotide
      sequence

<400> SEQUENCE: 8
aattcggcgt atcagccatt ttcattt                                27

<210> SEQ ID NO 9
<211> LENGTH: 33
<212> TYPE: DNA
<213> ORGANISM: Artificial sequence
<220> FEATURE:
<223> OTHER INFORMATION: An artificially synthesized oligonucleotide
      sequence

<400> SEQUENCE: 9
gtcaggtaag gctaatttca ttaccagcaa agg                         33

<210> SEQ ID NO 10
<211> LENGTH: 26
<212> TYPE: DNA
<213> ORGANISM: Artificial sequence
<220> FEATURE:
<223> OTHER INFORMATION: An artificially synthesized oligonucleotide
      sequence

<400> SEQUENCE: 10
cggtcagcca tagggtaaat gaccac                                 26

<210> SEQ ID NO 11
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 11
gtttctggca cggcgtcagc                                        20

```
<210> SEQ ID NO 12
<211> LENGTH: 25
<212> TYPE: DNA
<213> ORGANISM: Artificial sequence
<220> FEATURE:
<223> OTHER INFORMATION: An artificially synthesized oligonucleotide
      sequence

<400> SEQUENCE: 12
tgtgtgtcta atcagttccg caggg                                           25

<210> SEQ ID NO 13
<211> LENGTH: 29
<212> TYPE: DNA
<213> ORGANISM: Artificial sequence
<220> FEATURE:
<223> OTHER INFORMATION: An artificially synthesized oligonucleotide
      sequence

<400> SEQUENCE: 13
cagccatcag gttgagcatc attaatctt                                       29

<210> SEQ ID NO 14
<211> LENGTH: 33
<212> TYPE: DNA
<213> ORGANISM: Artificial sequence
<220> FEATURE:
<223> OTHER INFORMATION: An artificially synthesized oligonucleotide
      sequence

<400> SEQUENCE: 14
cagccggaga aatagagaaa tcttatgaat cat                                  33

<210> SEQ ID NO 15
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 15
cggtcaacga gatgtggtct                                                 20

<210> SEQ ID NO 16
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 16
ggctcatctt ctagtggtgc                                                 20

<210> SEQ ID NO 17
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 17
ggccaaaagt gaagacattg                                                 20

<210> SEQ ID NO 18
```

```
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 18
ccatcttttc caggcgatgc                                              20

<210> SEQ ID NO 19
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 19
acaaatgggg ctggaggttc                                              20

<210> SEQ ID NO 20
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 20
caaccctcag gacaccactt                                              20

<210> SEQ ID NO 21
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 21
caactcggga tcggcaaaca                                              20

<210> SEQ ID NO 22
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 22
cgacagtacg cagccacgat                                              20

<210> SEQ ID NO 23
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 23
gccgtgctca atacagctcc                                              20

<210> SEQ ID NO 24
<211> LENGTH: 20
```

```
<212> TYPE: DNA
<213> ORGANISM: Artificial sequence
<220> FEATURE:
<223> OTHER INFORMATION: An artificially synthesized oligonucleotide
      sequence

<400> SEQUENCE: 24
ggacatgata tgggggcat                                                20

<210> SEQ ID NO 25
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 25
cgagacggcc ccagacctat                                               20

<210> SEQ ID NO 26
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 26
aagcaggcta tcggattctc                                               20

<210> SEQ ID NO 27
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 27
gtggctgacc ttaatgaacc                                               20

<210> SEQ ID NO 28
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 28
atcactggct ggcaaggcac                                               20

<210> SEQ ID NO 29
<211> LENGTH: 35
<212> TYPE: DNA
<213> ORGANISM: Artificial sequence
<220> FEATURE:
<223> OTHER INFORMATION: An artificially synthesized oligonucleotide
      sequence

<400> SEQUENCE: 29
cagtaatata atagtcttta tctacacttt ctaat                              35

<210> SEQ ID NO 30
<211> LENGTH: 25
<212> TYPE: DNA
```

<213> ORGANISM: Artificial sequence
<220> FEATURE:
<223> OTHER INFORMATION: An artificially synthesized oligonucleotide
      sequence

<400> SEQUENCE: 30
acttgtagag acacccgtta atact                                      25

<210> SEQ ID NO 31
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 31
taaagcgtcg cttagaaata atc                                        23

<210> SEQ ID NO 32
<211> LENGTH: 26
<212> TYPE: DNA
<213> ORGANISM: Artificial sequence
<220> FEATURE:
<223> OTHER INFORMATION: An artificially synthesized oligonucleotide
      sequence

<400> SEQUENCE: 32
taaatcttca agtattcgtg tagatg                                     26

<210> SEQ ID NO 33
<211> LENGTH: 26
<212> TYPE: DNA
<213> ORGANISM: Artificial sequence
<220> FEATURE:
<223> OTHER INFORMATION: An artificially synthesized oligonucleotide
      sequence

<400> SEQUENCE: 33
taaatatcga ttctgcacat atttta                                     26

<210> SEQ ID NO 34
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 34
cattgcgagt gaatttactg                                            20

<210> SEQ ID NO 35
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 35
gtgattacat tgacaattgt ttc                                        23

<210> SEQ ID NO 36
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 36
caaatggttt caacaaatta atg                                           23

<210> SEQ ID NO 37
<211> LENGTH: 16
<212> TYPE: DNA
<213> ORGANISM: Artificial sequence
<220> FEATURE:
<223> OTHER INFORMATION: An artificially synthesized oligonucleotide
      sequence

<400> SEQUENCE: 37
agcctagtcc agcggg                                                   16

<210> SEQ ID NO 38
<211> LENGTH: 17
<212> TYPE: DNA
<213> ORGANISM: Artificial sequence
<220> FEATURE:
<223> OTHER INFORMATION: An artificially synthesized oligonucleotide
      sequence

<400> SEQUENCE: 38
ttgtcattac ggggcgt                                                  17

<210> SEQ ID NO 39
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 39
gacctcaggc cgttaacat                                                19

<210> SEQ ID NO 40
<211> LENGTH: 16
<212> TYPE: DNA
<213> ORGANISM: Artificial sequence
<220> FEATURE:
<223> OTHER INFORMATION: An artificially synthesized oligonucleotide
      sequence

<400> SEQUENCE: 40
cgtgcatcgg gctgtg                                                   16

<210> SEQ ID NO 41
<211> LENGTH: 31
<212> TYPE: DNA
<213> ORGANISM: Artificial sequence
<220> FEATURE:
<223> OTHER INFORMATION: An artificially synthesized oligonucleotide
      sequence

<400> SEQUENCE: 41
gaagacaacg atttatgttt acgctttggc a                                  31

<210> SEQ ID NO 42
<211> LENGTH: 20
<212> TYPE: DNA
<213> ORGANISM: Artificial sequence
<220> FEATURE:

```
<223> OTHER INFORMATION: An artificially synthesized oligonucleotide
      sequence

<400> SEQUENCE: 42
tatacgcctt ttgaaacggt                                                   20

<210> SEQ ID NO 43
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 43
aatcaatggg gaaatttttt a                                                 21

<210> SEQ ID NO 44
<211> LENGTH: 24
<212> TYPE: DNA
<213> ORGANISM: Artificial sequence
<220> FEATURE:
<223> OTHER INFORMATION: An artificially synthesized oligonucleotide
      sequence

<400> SEQUENCE: 44
ttttaatgag tcaaagatta gcgg                                              24

<210> SEQ ID NO 45
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 45
taacagtaag ctggtcatgg                                                   20

<210> SEQ ID NO 46
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 46
cagtacaaca cgacgattta tg                                                22

<210> SEQ ID NO 47
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 47
gatcgctatc gagggtatt                                                    20

<210> SEQ ID NO 48
<211> LENGTH: 23
<212> TYPE: DNA
<213> ORGANISM: Artificial sequence
<220> FEATURE:
<223> OTHER INFORMATION: An artificially synthesized oligonucleotide
```

-continued sequence

<400> SEQUENCE: 48
ttatgagtgc taaacaagct aaa                                          23

<210> SEQ ID NO 49
<211> LENGTH: 18
<212> TYPE: DNA
<213> ORGANISM: Artificial sequence
<220> FEATURE:
<223> OTHER INFORMATION: An artificially synthesized oligonucleotide
      sequence

<400> SEQUENCE: 49
ggtcaacacc ccacagga                                                18

<210> SEQ ID NO 50
<211> LENGTH: 24
<212> TYPE: DNA
<213> ORGANISM: Artificial sequence
<220> FEATURE:
<223> OTHER INFORMATION: An artificially synthesized oligonucleotide
      sequence

<400> SEQUENCE: 50
aaatcattca aaagaatgct gaac                                         24

<210> SEQ ID NO 51
<211> LENGTH: 16
<212> TYPE: DNA
<213> ORGANISM: Artificial sequence
<220> FEATURE:
<223> OTHER INFORMATION: An artificially synthesized oligonucleotide
      sequence

<400> SEQUENCE: 51
tggcggtatg gatggg                                                  16

<210> SEQ ID NO 52
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 52
tgctgcatac gctctctga                                               19

<210> SEQ ID NO 53
<211> LENGTH: 14
<212> TYPE: DNA
<213> ORGANISM: Artificial sequence
<220> FEATURE:
<223> OTHER INFORMATION: An artificially synthesized oligonucleotide
      sequence

<400> SEQUENCE: 53
cgcggccctt tttt                                                    14

<210> SEQ ID NO 54
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 54
atattgccat tgtttatttt tc                                              22

<210> SEQ ID NO 55
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 55
ctatttttag cagcttgttc aa                                              22

<210> SEQ ID NO 56
<211> LENGTH: 24
<212> TYPE: DNA
<213> ORGANISM: Artificial sequence
<220> FEATURE:
<223> OTHER INFORMATION: An artificially synthesized oligonucleotide
      sequence

<400> SEQUENCE: 56
ctcatttacc aggaataatc ttac                                            24

<210> SEQ ID NO 57
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 57
gtgccgctca ccacaccatt                                                 20

<210> SEQ ID NO 58
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 58
tcacgacgac gaacgtacgc                                                 20

<210> SEQ ID NO 59
<211> LENGTH: 18
<212> TYPE: DNA
<213> ORGANISM: Artificial sequence
<220> FEATURE:
<223> OTHER INFORMATION: An artificially synthesized oligonucleotide
      sequence

<400> SEQUENCE: 59
accagtgggg agatcacg                                                   18

<210> SEQ ID NO 60
<211> LENGTH: 20
<212> TYPE: DNA
<213> ORGANISM: Artificial sequence
<220> FEATURE:
<223> OTHER INFORMATION: An artificially synthesized oligonucleotide
      sequence

```
<400> SEQUENCE: 60
gataaactcg ttaccggtca                                          20

<210> SEQ ID NO 61
<211> LENGTH: 18
<212> TYPE: DNA
<213> ORGANISM: Artificial sequence
<220> FEATURE:
<223> OTHER INFORMATION: An artificially synthesized oligonucleotide
      sequence

<400> SEQUENCE: 61
agaacagcct gcaggaga                                            18

<210> SEQ ID NO 62
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 62
aactacgtat ggctgagcc                                           19

<210> SEQ ID NO 63
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 63
tttagccttt gcaactccta                                          20

<210> SEQ ID NO 64
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 64
aaggggtagc agctgttaa                                           19

<210> SEQ ID NO 65
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 65
tagggatatg cacgcaaaag                                          20

<210> SEQ ID NO 66
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 66
```
gcttaataca gttacgatag                                        20

<210> SEQ ID NO 67
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 67
aagcataagt tttgcaaacg                                        20

<210> SEQ ID NO 68
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 68
gtttggattt tcaaatgttc c                                      21

<210> SEQ ID NO 69
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 69
ccttgcaccc tagatcctat                                        20

<210> SEQ ID NO 70
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 70
tcctgactct agtatcgcca                                        20

<210> SEQ ID NO 71
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 71
tcagatcgct cctagcggat                                        20

<210> SEQ ID NO 72
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 72
agcgccttta gggatacctc       20

<210> SEQ ID NO 73
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 73
taagccctag gggcgatgat       20

<210> SEQ ID NO 74
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 74
acgcaatgca aacaccggaa       20

<210> SEQ ID NO 75
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 75
gcttagaaac gggaattttt tta       23

<210> SEQ ID NO 76
<211> LENGTH: 25
<212> TYPE: DNA
<213> ORGANISM: Artificial sequence
<220> FEATURE:
<223> OTHER INFORMATION: An artificially synthesized oligonucleotide
      sequence

<400> SEQUENCE: 76
aaaagatcct attgatcaaa attgg       25

<210> SEQ ID NO 77
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 77
aaaacgcttt ggaatagcc       19

<210> SEQ ID NO 78
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 78
tttttttgct gaagtaaatg aac       23

<210> SEQ ID NO 79
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 79 gcctttggc tatgttcagt tta                                           23

<210> SEQ ID NO 80
<211> LENGTH: 24
<212> TYPE: DNA
<213> ORGANISM: Artificial sequence
<220> FEATURE:
<223> OTHER INFORMATION: An artificially synthesized oligonucleotide
      sequence

<400> SEQUENCE: 80
atatgcctag ctgttttaag tgaa                                         24

<210> SEQ ID NO 81
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 81
caatcaatgc atgagcactt t                                            21

<210> SEQ ID NO 82
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 82
tagaaaatcg ctttggttta gg                                           22

<210> SEQ ID NO 83
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 83
cataaccgac gcttttcaaa t                                            21

<210> SEQ ID NO 84
<211> LENGTH: 27
<212> TYPE: DNA
<213> ORGANISM: Artificial sequence
<220> FEATURE:
<223> OTHER INFORMATION: An artificially synthesized oligonucleotide
      sequence

<400> SEQUENCE: 84
ttcctataaa tataaagcga ttttcag                                      27

<210> SEQ ID NO 85
<211> LENGTH: 19
<212> TYPE: DNA
<213> ORGANISM: Artificial sequence
<220> FEATURE:
<223> OTHER INFORMATION: An artificially synthesized oligonucleotide sequence

<400> SEQUENCE: 85
ccgacgtaaa aatgtgcct                                              19

<210> SEQ ID NO 86
<211> LENGTH: 23
<212> TYPE: DNA
<213> ORGANISM: Artificial sequence
<220> FEATURE:
<223> OTHER INFORMATION: An artificially synthesized oligonucleotide sequence

<400> SEQUENCE: 86
ttttagcact aaaaaactgc aag                                         23

<210> SEQ ID NO 87
<211> LENGTH: 22
<212> TYPE: DNA
<213> ORGANISM: Artificial sequence
<220> FEATURE:
<223> OTHER INFORMATION: An artificially synthesized oligonucleotide sequence

<400> SEQUENCE: 87 cgcatttta ttaatgcttt cg                                           22

<210> SEQ ID NO 88
<211> LENGTH: 18
<212> TYPE: DNA
<213> ORGANISM: Artificial sequence
<220> FEATURE:
<223> OTHER INFORMATION: An artificially synthesized oligonucleotide sequence

<400> SEQUENCE: 88
gggctggcag agagagtg                                               18

<210> SEQ ID NO 89
<211> LENGTH: 20
<212> TYPE: DNA
<213> ORGANISM: Artificial sequence
<220> FEATURE:
<223> OTHER INFORMATION: An artificially synthesized oligonucleotide sequence

<400> SEQUENCE: 89
tcgtgggaac acaaccagtc                                             20

<210> SEQ ID NO 90
<211> LENGTH: 20
<212> TYPE: DNA
<213> ORGANISM: Artificial sequence
<220> FEATURE:
<223> OTHER INFORMATION: An artificially synthesized oligonucleotide sequence

<400> SEQUENCE: 90
gcctgataaa cttccgcctc                                             20

```
<210> SEQ ID NO 91
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 91
caaccagttg atgatggatc                                              20

<210> SEQ ID NO 92
<211> LENGTH: 18
<212> TYPE: DNA
<213> ORGANISM: Artificial sequence
<220> FEATURE:
<223> OTHER INFORMATION: An artificially synthesized oligonucleotide
      sequence

<400> SEQUENCE: 92
gccactctct ctgccagc                                                18

<210> SEQ ID NO 93
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 93
cgtgaagatt ttccatgacc                                              20

<210> SEQ ID NO 94
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 94
cataaacccg aggaataacg                                              20

<210> SEQ ID NO 95
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 95
ctaaagcgtc gcttagaaa                                               19

<210> SEQ ID NO 96
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 96
cttcaagtat tcgtgtagat gc                                           22

<210> SEQ ID NO 97
```

```
<211> LENGTH: 16
<212> TYPE: DNA
<213> ORGANISM: Artificial sequence
<220> FEATURE:
<223> OTHER INFORMATION: An artificially synthesized oligonucleotide
      sequence

<400> SEQUENCE: 97
cgctaaagcg tcgctt                                                       16

<210> SEQ ID NO 98
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 98
agtattcgtg tagatgcat                                                    19

<210> SEQ ID NO 99
<211> LENGTH: 33
<212> TYPE: DNA
<213> ORGANISM: Artificial sequence
<220> FEATURE:
<223> OTHER INFORMATION: An artificially synthesized oligonucleotide
      sequence

<400> SEQUENCE: 99
aaacagtaat ataatagtct ttatctacac ttt                                    33

<210> SEQ ID NO 100
<211> LENGTH: 25
<212> TYPE: DNA
<213> ORGANISM: Artificial sequence
<220> FEATURE:
<223> OTHER INFORMATION: An artificially synthesized oligonucleotide
      sequence

<400> SEQUENCE: 100
tagagacacc cgttaatact aaatg                                             25

<210> SEQ ID NO 101
<211> LENGTH: 35
<212> TYPE: DNA
<213> ORGANISM: Artificial sequence
<220> FEATURE:
<223> OTHER INFORMATION: An artificially synthesized oligonucleotide
      sequence

<400> SEQUENCE: 101
tcttctaaaa cagtaatata atagtcttta tctac                                  35

<210> SEQ ID NO 102
<211> LENGTH: 23
<212> TYPE: DNA
<213> ORGANISM: Artificial sequence
<220> FEATURE:
<223> OTHER INFORMATION: An artificially synthesized oligonucleotide
      sequence

<400> SEQUENCE: 102
acacccgtta atactaaatg att                                               23

<210> SEQ ID NO 103
<211> LENGTH: 22
```

```
<212> TYPE: DNA
<213> ORGANISM: Artificial sequence
<220> FEATURE:
<223> OTHER INFORMATION: An artificially synthesized oligonucleotide
      sequence

<400> SEQUENCE: 103
ggttggccaa tctactccca gg                                              22

<210> SEQ ID NO 104
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 104
tggtctcctt aaacctgtct tg                                              22

<210> SEQ ID NO 105
<211> LENGTH: 33
<212> TYPE: DNA
<213> ORGANISM: Artificial sequence
<220> FEATURE:
<223> OTHER INFORMATION: An artificially synthesized oligonucleotide
      sequence

<400> SEQUENCE: 105
gtcaggtaag gctaatttca ttaccagcaa agg                                  33

<210> SEQ ID NO 106
<211> LENGTH: 26
<212> TYPE: DNA
<213> ORGANISM: Artificial sequence
<220> FEATURE:
<223> OTHER INFORMATION: An artificially synthesized oligonucleotide
      sequence

<400> SEQUENCE: 106
cggtcagcca tagggtaaat gaccac                                          26

<210> SEQ ID NO 107
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 107
atggtgcacc tgactcctga                                                 20

<210> SEQ ID NO 108
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 108
agcaacctca aacagacacc                                                 20

<210> SEQ ID NO 109
<211> LENGTH: 20
<212> TYPE: DNA
```

<213> ORGANISM: Artificial sequence
<220> FEATURE:
<223> OTHER INFORMATION: An artificially synthesized oligonucleotide
      sequence

<400> SEQUENCE: 109
ggagaagtct gccgttactg                                               20

<210> SEQ ID NO 110
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 110
ggtcagccat agggtaaatg ac                                            22

<210> SEQ ID NO 111
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 111
ttatgatgtc agaggtcatg g                                             21

<210> SEQ ID NO 112
<211> LENGTH: 16
<212> TYPE: DNA
<213> ORGANISM: Artificial sequence
<220> FEATURE:
<223> OTHER INFORMATION: An artificially synthesized oligonucleotide
      sequence

<400> SEQUENCE: 112
gtttgatcct ggctca                                                   16

<210> SEQ ID NO 113
<211> LENGTH: 18
<212> TYPE: DNA
<213> ORGANISM: Artificial sequence
<220> FEATURE:
<223> OTHER INFORMATION: An artificially synthesized oligonucleotide
      sequence

<400> SEQUENCE: 113
taccagggta tctaatcc                                                 18

<210> SEQ ID NO 114
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 114
gcagcagtag ggaatcttcg                                               20

<210> SEQ ID NO 115
<211> LENGTH: 20
<212> TYPE: DNA
<213> ORGANISM: Artificial sequence

```
<220> FEATURE:
<223> OTHER INFORMATION: An artificially synthesized oligonucleotide
      sequence

<400> SEQUENCE: 115
cacactggaa ctgagacacg                                              20

<210> SEQ ID NO 116
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 116
tggtctgaga ggatgatcag t                                            21

<210> SEQ ID NO 117
<211> LENGTH: 19
<212> TYPE: DNA
<213> ORGANISM: Artificial sequence
<220> FEATURE:
<223> OTHER INFORMATION: An artificially synthesized oligonucleotide
      sequence

<400> SEQUENCE: 117
gtccagactc ctacgggag                                               19

<210> SEQ ID NO 118
<211> LENGTH: 17
<212> TYPE: DNA
<213> ORGANISM: Artificial sequence
<220> FEATURE:
<223> OTHER INFORMATION: An artificially synthesized oligonucleotide
      sequence

<400> SEQUENCE: 118
acaatgggcg aaagcct                                                 17

<210> SEQ ID NO 119
<211> LENGTH: 16
<212> TYPE: DNA
<213> ORGANISM: Artificial sequence
<220> FEATURE:
<223> OTHER INFORMATION: An artificially synthesized oligonucleotide
      sequence

<400> SEQUENCE: 119
gtaacaaggt ytccgt                                                  16

<210> SEQ ID NO 120
<211> LENGTH: 15
<212> TYPE: DNA
<213> ORGANISM: Artificial sequence
<220> FEATURE:
<223> OTHER INFORMATION: An artificially synthesized oligonucleotide
      sequence

<400> SEQUENCE: 120
cgttcttcat cgatg                                                   15

<210> SEQ ID NO 121
<211> LENGTH: 20
<212> TYPE: DNA
<213> ORGANISM: Artificial sequence
<220> FEATURE:
```

```
<223> OTHER INFORMATION: An artificially synthesized oligonucleotide
      sequence

<400> SEQUENCE: 121
aggtgaacct gcggaaggat                                                   20

<210> SEQ ID NO 122
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 122
ttggcggtgg gcccagcctg                                                   20

<210> SEQ ID NO 123
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 123
cacacgactc gacactttct                                                   20

<210> SEQ ID NO 124
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 124
ctacactgcg tgagcggaac                                                   20

<210> SEQ ID NO 125
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 125
tggtaggcct tctatatggg                                                   20

<210> SEQ ID NO 126
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 126
tctttggtgg cgggagcaat                                                   20

<210> SEQ ID NO 127
<211> LENGTH: 24
<212> TYPE: DNA
<213> ORGANISM: Artificial sequence
<220> FEATURE:
<223> OTHER INFORMATION: An artificially synthesized oligonucleotide
``` sequence

<400> SEQUENCE: 127
cattactgat ttgcttaatt gcac                                              24

<210> SEQ ID NO 128
<211> LENGTH: 24
<212> TYPE: DNA
<213> ORGANISM: Artificial sequence
<220> FEATURE:
<223> OTHER INFORMATION: An artificially synthesized oligonucleotide
      sequence

<400> SEQUENCE: 128
gtttttcttt gaaacaaact tgct                                              24

<210> SEQ ID NO 129
<211> LENGTH: 21
<212> TYPE: DNA
<213> ORGANISM: Artificial sequence
<220> FEATURE:
<223> OTHER INFORMATION: An artificially synthesized oligonucleotide
      sequence

<400> SEQUENCE: 129
ccgccagagg tctaaactta c                                                 21

<210> SEQ ID NO 130
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 130
ttccaaagga ggtgttttat                                                   20

<210> SEQ ID NO 131
<211> LENGTH: 25
<212> TYPE: DNA
<213> ORGANISM: Artificial sequence
<220> FEATURE:
<223> OTHER INFORMATION: An artificially synthesized oligonucleotide
      sequence

<400> SEQUENCE: 131
aattactaca cacagtggag tttac                                             25

<210> SEQ ID NO 132
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 132
gaaaacaaca cacctaaaa tg                                                 22

<210> SEQ ID NO 133
<211> LENGTH: 25
<212> TYPE: DNA
<213> ORGANISM: Artificial sequence
<220> FEATURE:
<223> OTHER INFORMATION: An artificially synthesized oligonucleotide
      sequence

```
<400> SEQUENCE: 133
cattacagaa tgaaaagtgc ttaac                                         25

<210> SEQ ID NO 134
<211> LENGTH: 22
<212> TYPE: DNA
<213> ORGANISM: Artificial sequence
<220> FEATURE:
<223> OTHER INFORMATION: An artificially synthesized oligonucleotide
      sequence

<400> SEQUENCE: 134 tcttttttg aaactttgc tt                                              22

<210> SEQ ID NO 135
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 135
gcctgccaga gattaaactc                                               20

<210> SEQ ID NO 136
<211> LENGTH: 26
<212> TYPE: DNA
<213> ORGANISM: Artificial sequence
<220> FEATURE:
<223> OTHER INFORMATION: An artificially synthesized oligonucleotide
      sequence

<400> SEQUENCE: 136
cacatgtgtt ttttattgaa caaatt                                        26

<210> SEQ ID NO 137
<211> LENGTH: 20
<212> TYPE: DNA
<213> ORGANISM: Artificial sequence
<220> FEATURE:
<223> OTHER INFORMATION: An artificially synthesized oligonucleotide
      sequence

<400> SEQUENCE: 137
cctaccgcca gaggttataa                                               20
```

NUCLEIC ACID DETECTION OR QUANTIFICATION METHOD USING MASK OLIGONUCLEOTIDE, AND DEVICE FOR SAME

This application is a U.S. National Stage Filing under 35 U.S.C. 371 from International Application No. PCT/JP2015/052501, filed on Jan. 29, 2015, and published as WO 2015/119035 A1 on Aug. 13, 2015, and which claims the benefit of priority under 35 U.S.C. § 119 to Japanese Patent Application No. 2014-020183, filed on Feb. 5, 2014, each of which is hereby incorporated by reference herein in its entirety.

TECHNICAL FIELD

The present invention relates to simple and highly sensitive methods for detecting or quantifying nucleic acids (for example, naturally-occurring nucleic acids, genomic DNA, cDNA, RNA, and nucleic acids amplified by polymerase chain reaction (PCR)) derived from various organisms including viruses, bacteria, and microorganisms; and devices and kits used to perform the methods.

BACKGROUND ART

For examining the presence and degree of bacterial or viral infection of humans and other mammals, host organisms, plants, food or drinks, and such, and for identifying the cause of various diseases suspected to be caused by viral or bacterial infection or genetic mutations (such as infectious diseases, cancer, metabolic diseases, genetic diseases), gene testing methods have been used as very useful methods because of their specificity and high sensitivity.

Gene testing methods can be broadly classified into methods that use hybridization of nucleic acids and methods that use polymerase chain reaction (PCR) of nucleic acids.

In the methods that use hybridization of nucleic acids, when a target nucleic acid to be detected is double stranded, the double-stranded nucleic acid is denatured into single strands; then a detectably labeled oligonucleotide probe complementary to a portion of the target single-stranded nucleic acid is allowed to hybridize, and then the target nucleic acid is detected using the label as an indicator.

In the methods that use PCR, when a nucleic acid to be detected is double stranded, the double-stranded nucleic acid is denatured by heat into single strands or to produce single-stranded regions; then a pair of complementary oligonucleotide primers are allowed to bind with portions of the single-stranded nucleic acids; the step of nucleic acid replication with a DNA polymerase is repeated again and again to amplify the target nucleic acid many times; and then the amplified nucleic acid (PCR product) is electrophoresed and the target nucleic acid is detected using the presence of a band with the predicted size as an indicator.

In both methods, when the nucleic acid to be detected is double stranded, the double-stranded nucleic acid needs to be denatured into single strands or so as to produce single-stranded regions. Even when the nucleic acid to be detected is already a single-stranded nucleic acid, such as rRNA or already denatured DNA, the nucleic acid has to be made single stranded in advance of detection by the above-mentioned methods. This is because single-stranded nucleic acids such as rRNA have secondary structures such as intramolecular loops formed by self-association through hydrogen bonds between complementary nucleotide sequences present within the molecule, and therefore it is necessary to denature them to make sure that they are single stranded with no secondary structures such as intramolecular loops so that oligonucleotide probes can bind to them.

When a target nucleic acid is made single stranded or allowed to produce single-stranded regions, it is often denatured by alkali or heat; but whichever method is used, when the denaturation conditions are eased (neutralized), the target nucleic acid immediately returns to the double-stranded state. Therefore, in order to hybridize oligonucleotide probes to the single-stranded target nucleic acid, the high temperature must be maintained, or the salt concentration or pH must be adjusted, or denaturants such as chaotropic ions and formamide must be added so that intermolecular binding forces such as hydrogen bonding are weakened to prevent association into double-strands and the target nucleic acid is maintained in the single-stranded state.

Furthermore, double-stranded nucleic acids reconstructed from denaturation conditions or from the single-stranded state may contain secondary structures such as intramolecular loops formed by hydrogen bonds between complementary nucleotide sequences present within the molecule, and/or may partially form incomplete double-strands.

In addition, the above-mentioned rRNA and such also form tertiary structures due to the same type of attracting force by which a double-stranded DNA forms a helical structure.

The essential part of these secondary and tertiary structures does not easily disappear under denaturation conditions such as high temperature, presence of salts, and presence of denaturants such as chaotropic ions and formamide. The presence of such higher-order structures in the target nucleic acid inhibits or interferes with hybrid formation between the oligonucleotide probes and the target nucleic acid. Furthermore, inhibition of the hybridization causes the oligonucleotide probes to bind nonspecifically to other regions in the targeted nucleic acid than the target complementary region to which the probe should bind, and new secondary and tertiary structures are formed at the target site of the target single-stranded nucleic acid. As a result, the target nucleic acid cannot be detected accurately.

On the other hand, there are reports that in the detection of target rRNA by hybridization assay using a fluorescence-labeled oligonucleotide probe, when helper oligonucleotides are bound to regions adjacent to or distant from a region of the target rRNA which the oligonucleotide probe binds to so that the region which the oligonucleotide probe binds to is not blocked, formation of higher-order structures such as those described above which inhibit binding of oligonucleotide probes to rRNA was decreased, non-specific binding of oligonucleotide probes to target rRNA was decreased, and specific binding of oligonucleotide probes to target rRNA was increased; and as a result, the target rRNA was more effectively detected using the fluorescence emitted by the fluorescence-labeled oligonucleotide probe as an indicator (Patent Document 1, Non-Patent Document 1, and Non-Patent Document 2).

Next, in the methods for detecting a target nucleic acid using PCR, operations for nucleic acid amplification itself with a PCR apparatus are not particularly complicated, and the time required for nucleic acid amplification is relatively short approximately four hours.

However, detection and identification of the PCR-amplified nucleic acid (PCR product) requires complicated processing steps involving agarose electrophoresis, fluorescent staining with EtBr or the like and destaining; detection of the nucleic acid using a special apparatus such as a UV transilluminator; and determination of its molecular weight.

Furthermore, in the detection and identification of the PCR product, non-specific PCR products having a molecular weight close to that of the PCR product of interest are sometimes detected, causing false positives. Furthermore, when the target nucleic acid to be detected is a wild-type nucleic acid, and when the nucleic acid in the sample has mutations (insertion, deletion, or such of nucleotides), PCR products with a molecular weight different from that predicted for the PCR product of the wild-type nucleic acid are detected. As a result, PCR products that should be recognized as positive are recognized as non-specifically amplified PCR products, thereby causing false negatives.

Meanwhile, there are also reports in which lateral-flow immunochromatography, which utilizes antigen-antibody reaction used for detection and identification of antigens and proteins, is used for detection and identification of nucleic acids.

In this lateral-flow immunochromatography, in principle, a labeled antibody for capturing an antigen (capture antibody) is placed at one end of a membrane strip made of nitrocellulose or the like; a sample containing the antigen is added to this; an antigen-capture antibody complex developed through the membrane strip is allowed to bind to an antibody for detection (detection antibody) immobilized at the other end of the membrane; and the antigen is detected using the label as an indicator. Several modifications of this method are also known (Patent Documents 2 and 3).

One approach is the following method: a pair of oligonucleotide primers are designed so that they can hybridize to a target nucleotide sequence and its complementary strand, and each of them is labeled with a different label (for example, biotin, fluorescent dye, or digoxigenin) (for example, one oligonucleotide primer is labeled with one of a pair of reactive elements (for example, biotin), and the other oligonucleotide primer is labeled with a detectable substance (for example, a fluorescent dye)); the target nucleic acid is amplified by performing PCR using the pair of oligonucleotide primers to obtain the double-stranded DNA (amplified target nucleic acid) carrying the two different labels; the amplified target nucleic acid is developed through a membrane strip which has the other member of the reactive pair (for example, avidin) at one end; and the amplified target nucleic acid captured by the reactive component (for example, avidin) is detected using the other label (for example, fluorescent dye) carried by the target nucleic acid as the indicator (Patent Document 4).

Another approach is a method for detecting a double-stranded nucleic acid, in which: a nucleic acid to be detected is subjected to PCR with PCR primers designed to prepare a target double-stranded nucleic acid having a single-stranded overhang at each end; a labeled oligonucleotide for capturing the target double-stranded nucleic acid via the terminal overhang nucleic acid is placed at one end of a membrane strip; the target double-stranded nucleic acid is added to this; the target double-stranded nucleic acid bound with the labeled oligonucleotide is developed through the membrane strip and is allowed to bind to an oligonucleotide for detection immobilized at the other end of the membrane via the terminal overhang nucleic acid; and the double-stranded nucleic acid is detected using the label as the indicator (Patent Document 5).

A further approach is a method for detecting amplified RNA, in which: amplified RNA is prepared; a labeled oligonucleotide for capturing the target RNA is placed at one end of a membrane strip; the target RNA is added to this; the target RNA bound with the labeled oligonucleotide is developed through the membrane strip and allowed to bind to an oligonucleotide for detection which is immobilized at the other end of the membrane; and the labeled RNA is detected using the label as the indicator (Patent Document 6).

PRIOR ART DOCUMENTS

Patent Documents

[Patent Document 1] Japanese Patent No. 2820749
[Patent Document 2] Japanese Patent No. 3197277
[Patent Document 3] Japanese Patent Application Kokai Publication No. (JP-A) H10-253632 (unexamined, published Japanese patent application)
[Patent Document 4] Japanese Patent No. 3001906
[Patent Document 5] WO 2012/070618
[Patent Document 6] JP-A (Kokai) 2006-201062

Non-Patent Documents

[Non-Patent Document 1] Applied and Environmental Microbiology, Vol. 66, No. 8, p. 3603-3607, 2000
[Non-Patent Document 2] BioTechniques, Vol. 36, No. 1, p. 124-132, 2004

SUMMARY OF THE INVENTION

Problems to be Solved by the Invention

As described above, in examining the presence and degree of bacterial or viral infection of humans and other mammals, host organisms, plants, food or drinks, and such, and in detecting viral or bacterial infection or genetic mutations, it is recognized that gene testing methods which utilize PCR with oligonucleotide primers or hybridization with an oligonucleotide probe complementary to a portion of the target nucleic acid to be detected are useful; however, there has been no method provided yet that allows simple and highly sensitive detection and quantification of target nucleic acids without complicated operations while stably maintaining the target nucleic acid in the single-stranded state or in the state of having a single-stranded region during the assay. Accordingly, there is a demand for novel methods enabling such detection and quantification, which may address recent concerns against pandemics, needs for food safety, and needs for identification of causes of diseases, treatment of such diseases, and development of therapeutic methods.

An objective of the present invention is to provide very simple and highly sensitive methods for detection and quantification of nucleic acids (for example, naturally-occurring nucleic acids, genomic DNA, cDNA, RNA, and nucleic acids amplified by PCR and such) derived from various organisms including viruses, bacteria, and microorganisms, and genetically engineered plants, and provide devices and kits used to perform such methods, and thereby satisfy the above-mentioned social needs.

Means for Solving the Problems

To solve the above-mentioned problems, the present inventors carried out dedicated research on how to simply and highly sensitively detect or quantify nucleic acids derived from various organisms including viruses, bacteria, microorganisms, and genetically engineered plants. They discovered that a target nucleic acid of interest can be detected/quantified in a very simple and highly sensitive manner by:

hybridizing mask oligonucleotides (oligonucleotide M1', oligonucleotide M2', . . . , and oligonucleotide MX', which will be described later) to regions in a target nucleic acid to be assayed that has a single-stranded region between which a region to which an oligonucleotide probe hybridizes is positioned, so that the region to which the probe hybridizes is opened and the target nucleic acid is maintained stably in the single-stranded state or in the state of retaining the single-stranded region; and
developing the target nucleic acid having the single-stranded region on a membrane and capturing it with the oligonucleotide probe, and then subjecting the target nucleic acid to immunoassay or chromatography (hereinafter referred to as "nucleic acid chromatography") to detect or quantify the target nucleic acid using the label possessed or generated by the captured target nucleic acid (in the present invention, it means a nucleic acid hybrid formed by hybridization of the target nucleic acid with one or more other oligonucleotides) as an indicator; and thereby completed the present invention.

More specifically, the present invention relates to the following methods, devices, kits, and such.

Embodiment 1

A method for detecting or quantifying one target nucleic acid or two or more different target nucleic acids contained in a sample by chromatography, wherein the method comprises:

(a) hybridizing at least one of oligonucleotides M1', M2', M3', and M4' to at least one of regions M1, M2, M3, and M4, respectively, in a single-stranded region of a target nucleic acid N, wherein the target nucleic acid N comprises a region R1 that is positioned between the regions M1 and M2, and a region R2 that is different from the region R1 and positioned between the regions M3 and M4, wherein the oligonucleotides M1', M2', M3', and M4' comprise a nucleotide sequence complementary to the regions M1, M2, M3, and M4, respectively;

(b) hybridizing an oligonucleotide R1' labeled with a label L1 to the region R1, wherein the oligonucleotide R1' comprises a nucleotide sequence complementary to said region;

(c) hybridizing an oligonucleotide R2' to the region R2, wherein the oligonucleotide R2' comprises a nucleotide sequence complementary to said region or comprises an anchor A at its terminus; and (d) detecting or quantifying a nucleic acid hybrid formed through (a) to (c) using the label L1 as an indicator; and (e) as necessary, when the sample contains two or more different target nucleic acids N, performing said (a) to (d) for each target nucleic acid N for detection or quantification of each target nucleic acid N.

Embodiment 2

The method of Embodiment 1, wherein the hybridization of said (a) comprises any of the following:

(i) hybridization of at least one of the oligonucleotides M1' and M2' to at least one of the regions M1 and M2, respectively;

(ii) hybridization of at least one of the oligonucleotides M3' and M4' to at least one of the regions M3 and M4, respectively;

(iii) hybridization of at least one of the oligonucleotides M1' and M2' to at least one of the regions M1 and M2, respectively, and hybridization of at least one of the oligonucleotides M3' and M4' to at least one of the regions M3 and M4, respectively;

(iv) hybridization of the oligonucleotides M1' and M2' to both the regions M1 and M2, respectively;

(v) hybridization of the oligonucleotides M3' and M4' to both the regions M3 and M4, respectively;

(vi) hybridization of the oligonucleotides M1' and M3' to both the regions M1 and M3, respectively;

(vii) hybridization of the oligonucleotides M1' and M4' to both the regions M1 and M4, respectively;

(viii) hybridization of the oligonucleotides M2' and M3' to both the regions M2 and M3, respectively;

(ix) hybridization of the oligonucleotides M2' and M4' to both the regions M2 and M4, respectively; or (x) hybridization of the oligonucleotides M1' and M2' to both the regions M1 and M2, respectively, and hybridization of the oligonucleotides M3' and M4' to both the regions M3 and M4, respectively.

Embodiment 3

The method of Embodiment 1 or 2, wherein the chromatography is performed based on capillary action in a development element, wherein the development element comprises at least one detection zone for capturing and then detecting or quantifying a nucleic acid hybrid formed through said (a) and (b) or formed through said (a) to (c).

Embodiment 4

The method of Embodiment 3, wherein
the oligonucleotide R2' is immobilized on the detection zone; and
a mixture of the following is applied to a portion of the development element:
(i) the sample containing the target nucleic acid N,
(ii) at least one of the oligonucleotides M1', M2', M3', and M4', and
(iii) the oligonucleotide R1' labeled with the label L1.

Embodiment 5

The method of Embodiment 3, wherein
an acceptor A' capable of binding with the anchor A is immobilized on the detection zone; and
a mixture of the following is applied to a portion of the development element:
(i) the sample containing the target nucleic acid N,
(ii) at least one of the oligonucleotides M1', M2', M3', and M4',
(iii) the oligonucleotide R1' labeled with the label L1, and
(iv) the oligonucleotide R2' comprising the anchor A at its terminus.

Embodiment 6

The method of Embodiment 1 or 2, wherein the chromatography is performed based on capillary action in a development element, using a device which comprises:

(i) a development element comprising at least one detection zone for capturing and then detecting or quantifying a nucleic acid hybrid formed through said (a) and (b) or formed through said (a) to (c), and (ii) an application zone provided in contact with the development element for applying at least the sample containing the target nucleic acid N.

Embodiment 7

The method of Embodiment 6, wherein the device further comprises
(iii) an enclosing zone provided in contact with both the application zone and the development element to enclose a desired oligonucleotide.

Embodiment 8

The method of Embodiment 6 or 7, wherein
the oligonucleotide R2' is immobilized on the detection zone;
the application zone or the enclosing zone encloses:
(i) at least one of the oligonucleotides M1', M2', M3', and M4', and
(ii) the oligonucleotide R1' labeled with the label L1; and
the sample containing the target nucleic acid N is applied to the application zone.

Embodiment 9

The method of Embodiment 6 or 7, wherein
the oligonucleotide R2' is immobilized on the detection zone;
the application zone or the enclosing zone encloses the oligonucleotide R1' labeled with the label L1; and
a mixture of the following is applied to the application zone:
(i) the sample containing the target nucleic acid N, and
(ii) at least one of the oligonucleotides M1', M2', M3', and M4'.

Embodiment 10

The method of Embodiment 6 or 7, wherein
the oligonucleotide R2' is immobilized on the detection zone;
the application zone or the enclosing zone encloses at least one of the oligonucleotides M1', M2', M3', and M4'; and
a mixture of the following is applied to the application zone:
(i) the sample containing the target nucleic acid N; and
(ii) the oligonucleotide R1' labeled with the label L1.

Embodiment 11

The method of Embodiment 6 or 7, wherein
the oligonucleotide R2' is immobilized on the detection zone; and
a mixture of the following is applied to the application zone:
(i) the sample containing the target nucleic acid N;
(ii) at least one of the oligonucleotides M1', M2', M3', and M4', and (iii) the oligonucleotide R1' labeled with the label L1.

Embodiment 12

The method of Embodiment 6 or 7, wherein
an acceptor A' capable of binding with the anchor A is immobilized on the detection zone;
the application zone or the enclosing zone encloses:
(i) at least one of the oligonucleotides M1', M2', M3', and M4',
(ii) the oligonucleotide R1' labeled with the label L1, and
(iii) the oligonucleotide R2' comprising the anchor A at its terminus; and the sample containing the target nucleic acid N is applied to the application zone.

Embodiment 13

The method of Embodiment 6 or 7, wherein
an acceptor A' capable of binding with the anchor A is immobilized on the detection zone;
the application zone or the enclosing zone encloses:
(i) the oligonucleotide R1' labeled with the label L1, and
(ii) the oligonucleotide R2' comprising the anchor A at its terminus; and
a mixture of the following is applied to the application zone:
(i) the sample containing the target nucleic acid N, and
(ii) at least one of the oligonucleotides M1', M2', M3', and M4'.

Embodiment 14

The method of Embodiment 6 or 7, wherein
an acceptor A' capable of binding with the anchor A is immobilized on the detection zone;
the application zone or the enclosing zone encloses the oligonucleotide R2' comprising the anchor A at its terminus; and
a mixture of the following is applied to the application zone:
(i) the sample containing the target nucleic acid N,
(ii) at least one of the oligonucleotides M1', M2', M3', and M4', and (iii) the oligonucleotide R1' labeled with the label L1.

Embodiment 15

The method of Embodiment 6 or 7, wherein
an acceptor A' capable of binding with the anchor A is immobilized on the detection zone;
the application zone or the enclosing zone encloses:
(i) at least one of the oligonucleotides M1', M2', M3', and M4', and
(ii) the oligonucleotide R2' comprising the anchor A at its terminus; and
a mixture of the following is applied to the application zone:
(i) the sample containing the target nucleic acid N, and
(ii) the oligonucleotide R1' labeled with the label L1.

Embodiment 16

The method of Embodiment 6 or 7, wherein
an acceptor A' capable of binding with the anchor A is immobilized on the detection zone;
the application zone or the enclosing zone encloses at least one of the oligonucleotides M1', M2', M3', and M4'; and
a mixture of the following is applied to the application zone:
(i) the sample containing the target nucleic acid N,
(ii) the oligonucleotide R1' labeled with the label L1, and
(iii) the oligonucleotide R2' comprising the anchor A at its terminus.

Embodiment 17

The method of Embodiment 6 or 7, wherein
an acceptor A' capable of binding with the anchor A is immobilized on the detection zone;
the application zone or the enclosing zone encloses:
(i) at least one of the oligonucleotides M1', M2', M3', and M4', and
(ii) the oligonucleotide R1' labeled with the label L1; and
a mixture of the following is applied to the application zone:
(i) the sample containing the target nucleic acid N, and
(ii) the oligonucleotide R2' comprising the anchor A at its terminus.

Embodiment 18

The method of Embodiment 6 or 7, wherein
an acceptor A' capable of binding with the anchor A is immobilized in the detection zone;
the application zone or the enclosing zone encloses the oligonucleotide R1' labeled with the label L1; and
a mixture of the following is applied to the application zone:
(i) the sample containing the target nucleic acid N,
(ii) at least one of the oligonucleotides M1', M2', M3', and M4', and
(iii) the oligonucleotide R2' comprising the anchor A at its terminus.

Embodiment 19

The method of Embodiment 6 or 7, wherein
an acceptor A' capable of binding with the anchor A is immobilized on the detection zone; and
a mixture of the following is applied to the application zone:
(i) the sample containing the target nucleic acid N,
(ii) at least one of the oligonucleotides M1', M2', M3', and M4',
(iii) the oligonucleotide R1' labeled with the label L1, and
(iv) the oligonucleotide R2' comprising the anchor A at its terminus.

Embodiment 20

The method of any one of Embodiments 1 to 3, 5 to 7, and 12 to 19, wherein the anchor A is an oligonucleotide, biotin, antibody, protein, or sugar chain; and the acceptor A' is an oligonucleotide, avidin, streptavidin, antibody, or protein.

Embodiment 21

The method of Embodiment 20, wherein the anchor A is biotin, and the acceptor A' is avidin or streptavidin.

Embodiment 22

The method of Embodiment 20, wherein the acceptor A' is an antibody.

Embodiment 23

The method of any one of Embodiments 3 to 22, wherein, when the sample contains two or more different target nucleic acids N, the development element comprises (i) two or more detection zones on which the respective oligonucleotides R2' that hybridize to the respective target nucleic acids N are immobilized; or
(ii) two or more detection zones on which different acceptors A' are immobilized, wherein the respective acceptors A' are capable of binding with the respective oligonucleotides R2' each of which comprises a different anchor A at its terminus, wherein the respective oligonucleotides R2' hybridize to the respective target nucleic acids N.

Embodiment 24

The method of any one of Embodiments 6 to 23, wherein the device further comprises an absorption zone provided in contact with the development element to absorb a sample that has been developed beyond the detection zone.

Embodiment 25

The method of any one of Embodiments 1 to 24, wherein the label L1 is a colloidal metal particle, a latex particle, a pigmented liposome, or an enzyme.

Embodiment 26

The method of Embodiment 25, wherein the colloidal metal particle is a colloidal gold particle, a colloidal platinum particle, a colloidal platinum-gold particle, a palladium particle, a colloidal silver particle, a colloidal rhodium particle, a colloidal ruthenium particle, or a colloidal iridium particle.

Embodiment 27

The method of Embodiment 25, wherein the enzyme is peroxidase, glucose oxidase, alkaline phosphatase, or β-galactosidase.

Embodiment 28

The method of any one of Embodiments 3 to 27, wherein the development element or the device is placed in a case made of a moisture-impermeable solid material.

Embodiment 29

A method for detecting or quantifying one target nucleic acid or two or more different target nucleic acids contained in a sample by chromatography, wherein the method comprises:
(a) hybridizing at least one of oligonucleotides M1' and M2' to at least one of regions M1 and M2, respectively, in a single-stranded region of a target nucleic acid N which is labeled with a label L2, wherein the target nucleic acid N comprises a region R1 that is positioned between the regions M1 and M2, wherein the oligonucleotides M1' and M2' comprise a nucleotide sequence complementary to the regions M1 and M2, respectively;
(b) hybridizing an oligonucleotide R1' labeled with a label L1 to the region R1, wherein the oligonucleotide R1' comprises a nucleotide sequence complementary to said region; and
(c) capturing a nucleic acid hybrid formed through said (a) and (b) by means of binding of the label L2 with a substance that binds to the label L2, and detecting or quantifying the nucleic acid hybrid using the label L1 as an indicator; and (d) as necessary, when the sample contains two or more different target nucleic acids N, performing said (a) to (c) for each target nucleic acid N for detection or quantification of each target nucleic acid N.

Embodiment 30

The method of Embodiment 29, wherein the hybridization of said (a) comprises hybridization of the oligonucleotides M1' and M2' to both the regions M1 and M2, respectively.

Embodiment 31

The method of Embodiment 29 or 30, wherein the chromatography is performed based on capillary action in a development element, wherein the development element comprises at least one detection zone for capturing and then detecting or quantifying a nucleic acid hybrid formed through said (a) and (b).

Embodiment 32

The method of Embodiment 31, wherein
the substance that binds to the label L2 is immobilized on the detection zone; and
a mixture of the following is applied to a portion of the development element:
(i) the sample containing the target nucleic acid N,
(ii) at least one of the oligonucleotides M1' and M2', and
(iii) the oligonucleotide R1' labeled with the label L1.

Embodiment 33

The method of Embodiment 29 or 30, wherein the chromatography is performed based on capillary action in a development element, using a device which comprises:
(i) a development element which comprises at least one detection zone for capturing and then detecting or quantifying a nucleic acid hybrid formed through said (a) and (b); and
(ii) an application zone provided in contact with the development element for applying at least the sample comprising the target nucleic acid N.

Embodiment 34

The method of Embodiment 33, wherein the device is further comprises
(iii) an enclosing zone provided in contact with both the application zone and the development element to enclose a desired oligonucleotide.

Embodiment 351

The method of Embodiment 33 or 34, wherein
the substance that binds to the label L2 is immobilized on the detection zone;
the application zone or the enclosing zone encloses:
(i) at least one of the oligonucleotides M1' and M2', and
(ii) the oligonucleotide R1' labeled with the label L1; and
the sample containing the target nucleic acid N is applied to the application zone.

Embodiment 36

The method of Embodiment 33 or 34, wherein
the substance that binds to the label L2 is immobilized on the detection zone;
the application zone or the enclosing zone encloses the oligonucleotide R1' labeled with the label L1; and
a mixture of the following is applied to the application zone:
(i) the sample comprising the target nucleic acid N, and
(ii) at least one of the oligonucleotides M1' and M2'.

Embodiment 37

The method of Embodiment 33 or 34, wherein
the substance that binds to the label L2 is immobilized on the detection zone;
the application zone or the enclosing zone encloses at least one of the oligonucleotides M1' and M2'; and
a mixture of the following is applied to the application zone:
(i) the sample containing the target nucleic acid N, and
(ii) the oligonucleotide R1' labeled with the label L1.

Embodiment 38

The method of Embodiment 33 or 34, wherein
the substance that binds to the label L2 is immobilized on the detection zone; and
a mixture of the following is applied to the application zone:
(i) the sample containing the target nucleic acid N,
(ii) at least one of the oligonucleotides M1' and M2', and
(iii) the oligonucleotide R1' labeled with the label L1.

Embodiment 39

The method of any one of Embodiments 31 to 38, wherein when the sample contains two or more different target nucleic acids N, each target nucleic acid N is labeled with a label L2 that is different from one another; and the development element comprises two or more detection zones on each of which a different substance that binds to each label L2 is immobilized.

Embodiment 40

A method for detecting or quantifying one target nucleic acid or two or more different target nucleic acids contained in a sample, wherein the method comprises:
(a) hybridizing at least one of oligonucleotides M3' and M4' to at least one of regions M3 and M4, respectively, in a single-stranded region of a target nucleic acid N which is labeled with a label L2, wherein the target nucleic acid N comprises a region R2 that is positioned between the regions M3 and M4, and wherein the oligonucleotides M3' and M4' comprise a nucleotide sequence complementary to the regions M3 and M4, respectively;
(b) hybridizing an oligonucleotide R2' to the region R2, wherein the oligonucleotide R2' comprises a nucleotide sequence complementary to said region or comprises an anchor A at its terminus; and
(c) detecting or quantifying a nucleic acid hybrid formed through said (a) and (b) by using the label L2 as an indicator; and
(d) as necessary, when the sample contains two or more different target nucleic acids N, performing said (a) to (c) for each target nucleic acid N for detection or quantification of each target nucleic acid N.

Embodiment 41

The method of Embodiment 40, wherein the hybridization of said (a) comprises hybridization of the oligonucleotides M3' and M4' to both the regions M3 and M4, respectively.

Embodiment 42

The method of Embodiment 40 or 41, wherein the detection or quantification is performed by:
(A) chromatography that utilizes capillary action in a development element which comprises at least one detection zone for capturing and then detecting or quantifying a nucleic acid hybrid formed through said (a) and (b); or
(B) applying a mixture of:
(i) the sample containing the target nucleic acid N,
(ii) at least one of the oligonucleotides M3' and M4', and
(iii) the oligonucleotide R2' comprising the anchor A at its terminus to a solid support having a volume capacity, on the surface of which an acceptor A' capable of binding with the anchor A is immobilized, and detecting or quantifying the nucleic acid hybrid formed through said (a) and (b) which has been captured by means of binding of the anchor A with the acceptor A'.

Embodiment 43

The method of Embodiment 42, wherein
the oligonucleotide R2' is immobilized on the detection zone; and
a mixture of the following is applied to a portion of the development element:
(i) the sample containing the target nucleic acid N, and
(ii) at least one of the oligonucleotides M3' and M4'.

Embodiment 44

The method of Embodiment 40 or 41, wherein the detection or quantification is performed by chromatography that utilizes capillary action in a development element, using a device which comprises:
(i) a development element comprising at least one detection zone for capturing and then detecting or quantifying a nucleic acid hybrid formed through said (a) and (b), and
(ii) an application zone provided in contact with the development element for applying at least the sample comprising the target nucleic acid N.

Embodiment 45

The method of Embodiment 44, wherein the device further comprises
(iii) an enclosing zone provided in contact with both the application zone and the development element to enclose a desired oligonucleotide.

Embodiment 46

The method of Embodiment 44 or 45, wherein
the oligonucleotide R2' is immobilized on the detection zone;
the application zone or the enclosing zone encloses at least one of the oligonucleotides M3' and M4'; and
the sample containing the target nucleic acid N is applied to the application zone.

Embodiment 47

The method of Embodiment 44 or 45, wherein
the oligonucleotide R2' is immobilized on the detection zone; and
a mixture of the following is applied to the application zone:
(i) the sample containing the target nucleic acid N, and
(ii) at least one of the oligonucleotides M3' and M4'.

Embodiment 48

The method of Embodiment 44 or 45, wherein
an acceptor A' capable of binding with the anchor A is immobilized on the detection zone;
the application zone or the enclosing zone encloses:
(i) at least one of the oligonucleotides M3' and M4', and
(ii) the oligonucleotide R2' comprising the anchor A at its terminus; and
the sample containing the target nucleic acid N is applied to the application zone.

Embodiment 49

The method of Embodiment 44 or 45, wherein
an acceptor A' capable of binding with the anchor A is immobilized on the detection zone;
the application zone or the enclosing zone encloses the oligonucleotide R2' comprising the anchor A at its terminus; and
a mixture of:
(i) the sample containing the target nucleic acid N, and
(ii) at least one of the oligonucleotides M3' and M4' is applied to the application zone.

Embodiment 50

The method of Embodiment 44 or 45, wherein
an acceptor A' capable of binding with the anchor A is immobilized on the detection zone;
the application zone or the enclosing zone encloses at least one of the oligonucleotides M3' and M4'; and
a mixture of:
(i) the sample containing the target nucleic acid N, and
(ii) the oligonucleotide R2' comprising the anchor A at its terminus is applied to the application zone.

Embodiment 51

The method of Embodiment 44 or 45, wherein
an acceptor A' capable of binding with the anchor A is immobilized on the detection zone; and
a mixture of:
(i) the sample containing the target nucleic acid N,
(ii) at least one of the oligonucleotides M3' and M4', and
(iii) the oligonucleotide R2' comprising the anchor A at its terminus is applied to the application zone.

Embodiment 52

The method of any one of Embodiments 48 to 51, wherein when the sample contains two or more different target nucleic acids N, each target nucleic acid N is labeled with an identical label L2; and the development element comprises two or more detection zones on which different acceptors A' are immobilized, wherein the respective acceptors A' are capable of binding with the respective oligonucleotides R2' each of which comprises a different anchor A at its terminus, wherein the respective oligonucleotides R2' hybridize to the respective target nucleic acids N.

Embodiment 53

The method of any one of Embodiments 48 to 51, wherein when the sample contains two or more different target nucleic acids N, each target nucleic acid N is labeled with a label L2 that is different from one another.

Embodiment 54

The method of any one of Embodiments 29 to 53, wherein the label L2 is biotin, a fluorescent dye, digoxigenin (DIG), an antibody, or an enzyme.

Embodiment 55

The method of Embodiment 54, wherein the label L2 is biotin, and the substance that binds to the label L2 is avidin or streptavidin.

Embodiment 56

The method of any one of Embodiments 29 to 38, wherein the substance that binds to the label L2 is an antibody or an enzyme-labeled antibody.

Embodiment 57

The method of any one of Embodiments 33 to 39 and 44 to 56, wherein the device further comprises an absorption zone provided in contact with the development element to absorb a sample that has been developed beyond the detection zone.

Embodiment 58

The method of any one of Embodiments 29 to 39, wherein the label L1 is a colloidal metal particle, a latex particle, a pigmented liposome, or an enzyme.

Embodiment 59

The method of Embodiment 58, wherein the colloidal metal particle is a colloidal gold particle, a colloidal platinum particle, a colloidal platinum-gold particle, a palladium particle, a colloidal silver particle, a colloidal rhodium particle, a colloidal ruthenium particle, or a colloidal iridium particle.

Embodiment 60

The method of Embodiment 58, wherein the enzyme is peroxidase, glucose oxidase, alkaline phosphatase, or β-galactosidase.

Embodiment 61

The method of any one of Embodiments 31 to 39 and 41 to 60, wherein the development element or the device is placed in a case made of a moisture impermeable solid material.

Embodiment 62

The method of any one of Embodiments 1 to 61, wherein the single-stranded region of the target nucleic acid N is produced by denaturing a double-stranded nucleic acid.

Embodiment 63

The method of any one of Embodiments 1 to 62, wherein the target nucleic acid N is a DNA or an RNA.

Embodiment 64

The method of any one of Embodiments 1 to 63, wherein the target nucleic acid N is a nucleic acid derived from a genome of a eukaryote, a prokaryote, a bacterium, or a virus; a nucleic acid derived from a genome fragment produced by cleavage of the genome with a restriction enzyme; or an artificially amplified nucleic acid.

Embodiment 65

The method of Embodiment 64, wherein the nucleic acid derived from a bacterial genome is any one of the following:
1) a genomic nucleic acid of *Staphylococcus aureus* (hereinafter referred to as SA) comprising the nucleic acid sequence of a portion or all of the region from position 2653499 to position 2662118, the region from position 2656232 to position 2657658, or the region from position 2656470 to position 2656799, in the genomic DNA of SA identified by GenBank Accession No. FR714927;
2) a genomic nucleic acid of *Staphylococcus epidermis* (hereinafter referred to as SE) comprising the nucleic acid sequence of a portion or all of the region from position 384731 to position 393399, the region from position 385337 to position 388504, or the region from position 385517 to position 385796, in the genomic DNA of SE identified by GenBank Accession No. AE015929;
3) a genomic nucleic acid of *Pseudomonas aeruginosa* (hereinafter referred to as PA) comprising the nucleic acid sequence of a portion or all of the region from position 2386558 to position 2391818, the region from position 2386678 to position 2388735, or the region from position 2387395 to position 2387664, in the genomic DNA of PA identified by GenBank Accession No. CP004061;
4) a genomic nucleic acid of *Enterococcus faecalis* (hereinafter referred to as EF) comprising the nucleic acid sequence of a portion or all of the region from position 1837695 to position 1841178, the region from position 1838789 to position 1839704, or the region from position 1839147 to position 1839386, in the genomic DNA of EF identified by GenBank Accession No. HF558530;
5) a genomic nucleic acid of *Escherichia coli* (hereinafter referred to as EC) comprising the nucleic acid sequence of a portion or all of the region from position 1286884 to position 1291840, the region from position 1290625 to position 1291839, or the region from position 1291152 to position 1291460, in the genomic DNA of EC identified by GenBank Accession No. AP012306;
6) a genomic nucleic acid of *Enterobacter cloacae* comprising the nucleic acid sequence of a portion or all of the region from position 1566239 to position 1568859 or the region from position 1566732 to position 1566956 in the genomic DNA of *Enterobacter cloacae* identified by GenBank Accession No. CP001918; or
7) a genomic nucleic acid of *Klebsiella pneumoniae* (hereinafter referred to as KP) comprising the nucleic acid sequence of a portion or all of the region from position 4082686 to position 4083937, the region from position 4082686 to position 4083380, or the region from position 4082799 to position 4083096, in the genomic DNA of KP identified by GenBank Accession No. CP003785.

Embodiment 66

The method of any one of Embodiments 1 to 65, wherein the chromatography that uses the development element is performed in a buffer containing at least one denaturant or chaotropic agent, or containing at least one denaturant or chaotropic agent and at least one inorganic salt.

Embodiment 67

A device for use in the method of any one of Embodiments 24 to 28 and 57 to 66, which comprises:
(i) a development element which comprises at least one detection zone for capturing and then detecting or quantifying the formed nucleic acid hybrid;
(ii) an application zone provided in contact with the development element for applying at least the sample comprising the target nucleic acid N;
(iii) an enclosing zone provided in contact with both the application zone and the development element to enclose a desired oligonucleotide; and
(iv) an absorption zone provided in contact with the development element to absorb a sample that has been developed beyond the detection zone.

Embodiment 68

The device of Embodiment 67, wherein the development element is placed in a case made of a moisture impermeable solid material.

Effects of the Invention

In the present invention, the methods for detecting/quantifying nucleic acids by nucleic acid chromatography or immunoassay using mask oligonucleotides ("oligonucleotide M1'", "oligonucleotide M2'", "oligonucleotide M3'", "oligonucleotide M4'", . . . , "oligonucleotide MX'" in the above-described exemplary embodiments), and the devices and kits for use in these methods will, firstly, yield the following effects by employing the technical feature of "mask oligonucleotides":

1) the region to which the oligonucleotide probe hybridizes in the single-stranded region of the target nucleic acid to be detected is maintained in an open state during the assay;
2) during the assay, the target nucleic acid is stably maintained in the single-stranded state or in the state of retaining the single-stranded region;
3) as a result, the oligonucleotide probe hybridizes to the target nucleic acid at a higher rate;
4) even a target nucleic acid to which an oligonucleotide probe does not hybridize when no mask oligonucleotides are used can be detected by using mask oligonucleotides and also applying the nucleic acid chromatography or immunoassay of the present invention; and
5) since proteins, enzymes, and such are easily deactivated under non-physiological conditions like denaturing conditions used in ordinary nucleic acid hybridization for maintaining a double-stranded nucleic acid in the single-stranded state or in the state of retaining a single-stranded region (high temperature, salt concentration, and presence of a denaturant such as a chaotropic ion or formamide), labeling substances that are used in genetic tests employing the nucleic acid hybridization method are only small compounds such as fluorescent substances or digoxigenin, radioisotopes, or such; on the other hand, the use of mask oligonucleotides allows the denaturation conditions to be milder, enabling the use of protein labels and such or DNA polymerases etc., which could not be used previously.

Moreover, the methods of the present invention for detecting/quantifying nucleic acids by nucleic acid chromatography or immunoassay using mask oligonucleotides, and the devices and kits for use in those methods, further apply the technical feature of "nucleic acid chromatography" to the stable single-stranded nucleic acid or the nucleic acid having a stable single-stranded region in which the oligonucleotide probe-binding region has been opened by the use of mask oligonucleotides, and thereby provide effects that have never been reported before, i.e., enable very simple, quick, and highly sensitive detection and quantification of a target nucleic acid.

Since the methods of the present invention for detecting/quantifying nucleic acids by nucleic acid chromatography or immunoassay using mask oligonucleotides, and devices and kits for use in these methods provide those advantageous effects, it is possible to simply and highly sensitively detect/quantify any nucleic acid (for example, naturally-occurring nucleic acid, genomic DNA, cDNA, RNA, and nucleic acid amplified by PCR and such) derived from various organisms including viruses, bacteria, and microorganisms.

As a result, use of the methods, devices, and/or kits of the present invention will enable simple, quick, and highly precise identification of the presence and degree of bacterial or viral infection of humans and other mammals, host organisms, plants, food or drinks, and such; the causes of various diseases suspected to be caused by viral or bacterial infection or by genetic mutations (infectious diseases, cancer, metabolic diseases, genetic diseases, and such); and various genetic characteristics due to genetic diversity.

(3) shows the principle of the methods exemplified in Embodiments [12] to [19] and [23] described above (which correspond to embodiments (e) to (1) in Table 1 described below, respectively);

(4) shows the principle of the methods exemplified in Embodiments [35] to [39] described above (which correspond to embodiments (m) to (p) in Table 1 described below, respectively); and (5) and (6) show the principle of the methods exemplified in Embodiments [46] and [47] described above (which correspond to embodiments (q) and (r) in Table 1 described below, respectively).

(7) shows the principle of the methods exemplified in Embodiments [48] to [52] described above (which correspond to embodiments (s) to (v) in Table 1 described below, respectively).

Figure 1:
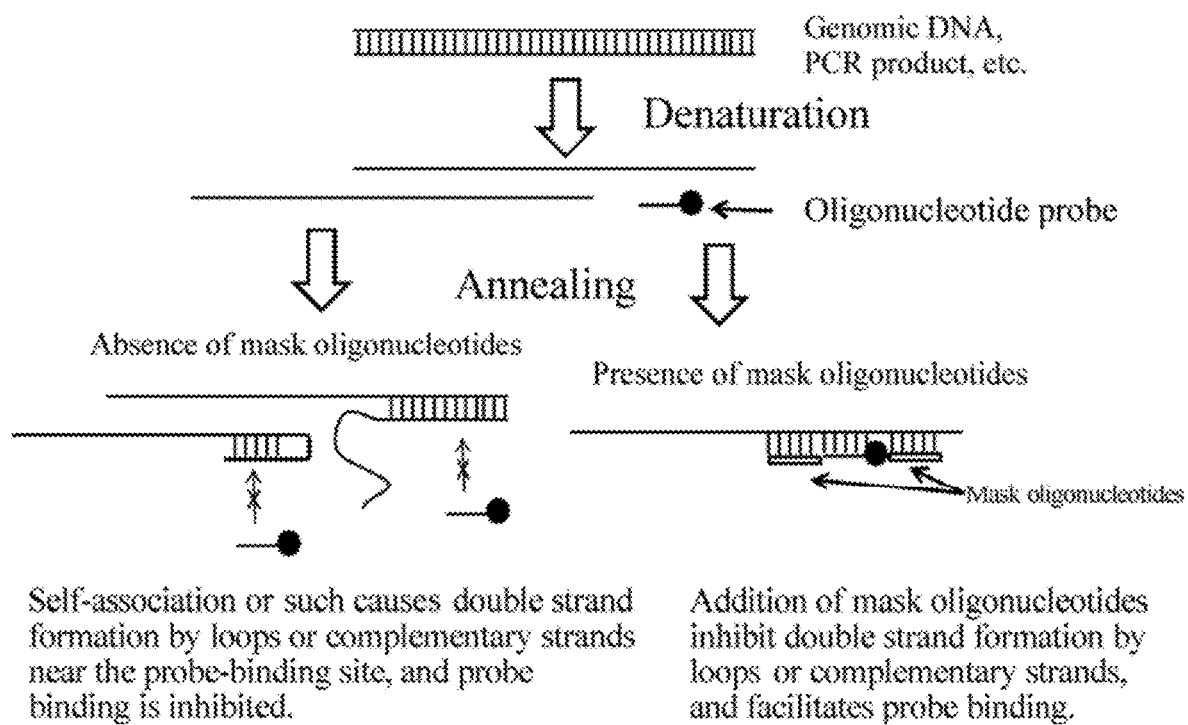
FIG. 1 schematically shows the principle underlying nucleic acid chromatography or immunoassays using mask oligonucleotides in the present invention.
Figures 1, 3:
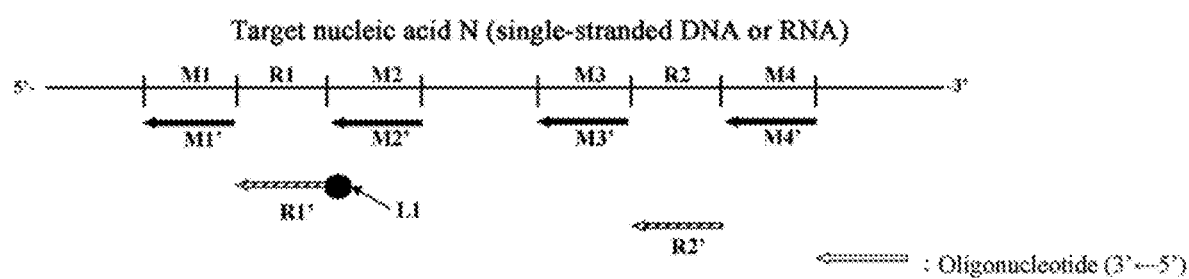
Figures 2, 3:
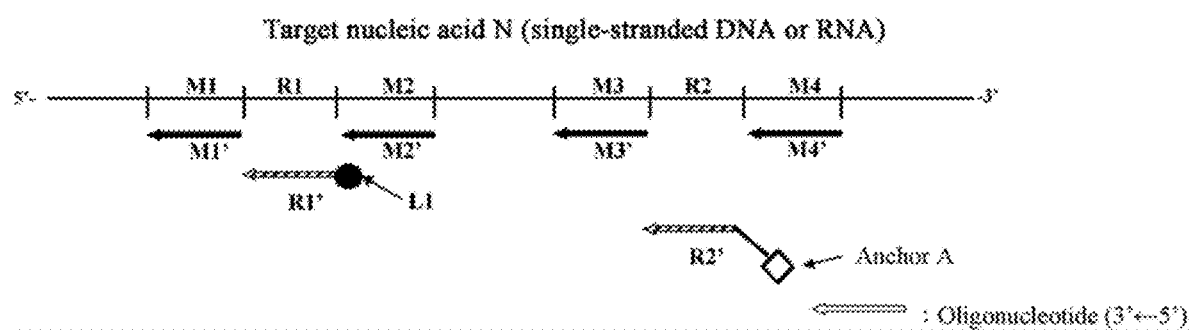
Figure 3:
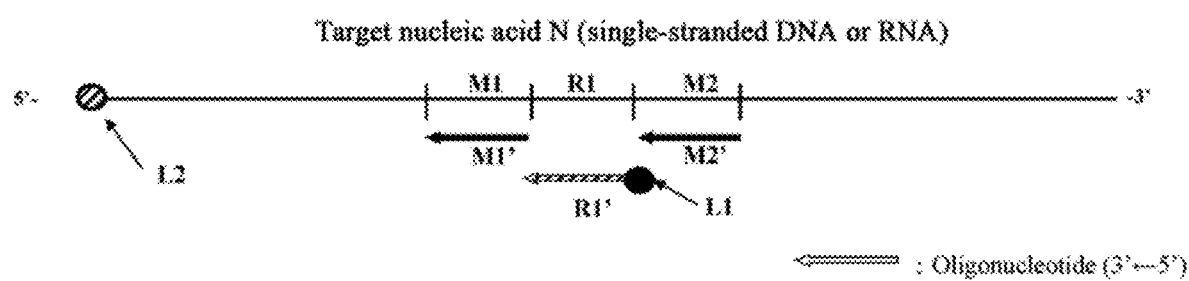

FIG. 3-1 schematically shows the principle of embodiments included in Embodiments [8] to [11] and [23] exemplified above (which correspond to embodiments (a) to (d) in Table 1 described below, respectively).

Figure 2:
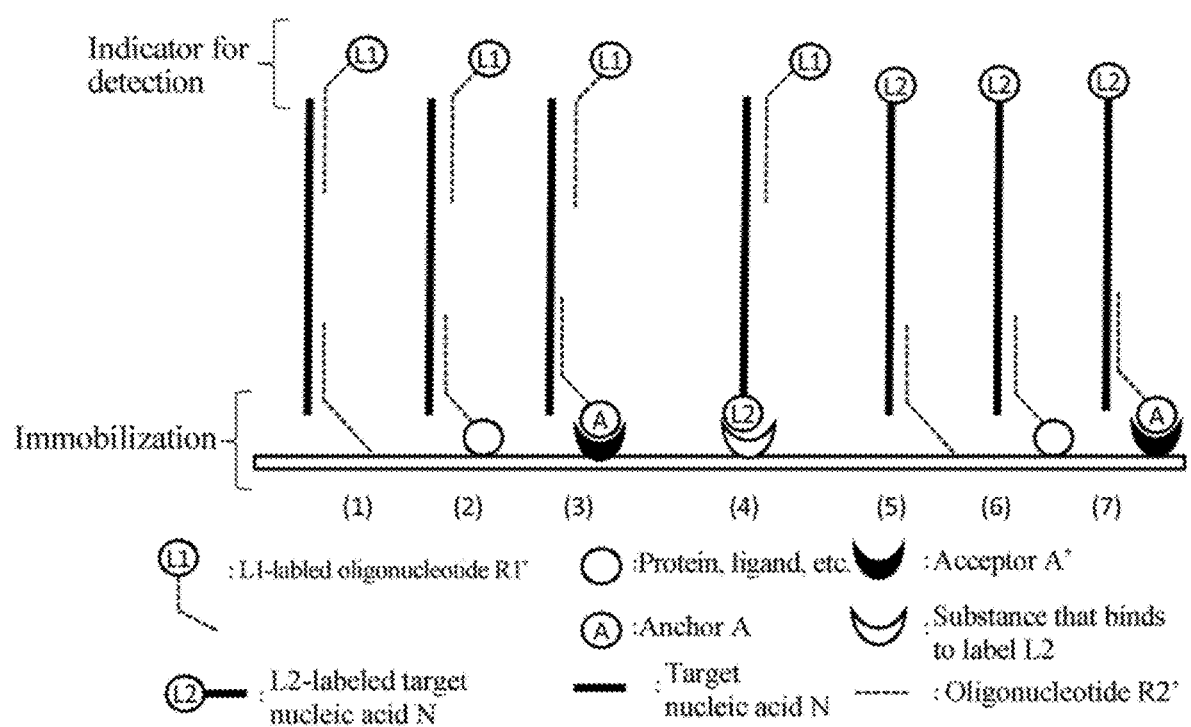
FIG. 2 schematically shows the principle of the method for capturing and detecting the target nucleic acid in each of the embodiments exemplified above. In this figure, (1) and (2) show the principle of the methods exemplified in Embodiments [8] to [11] and [23] described above (which correspond to embodiments (a) to (d) in Table 1 described below, respectively)

FIG. 3-2 schematically shows the principle of embodiments included in Embodiments [12] to [19] and [23] exemplified above (which correspond to embodiments (e) to (1) in Table 1 described below, respectively).

FIG. 3-3 schematically shows the principle of embodiments included in Embodiments [35] to [39] exemplified above (which correspond to embodiments (m) to (p) in Table 1 described below, respectively).

Figures 3, 4:
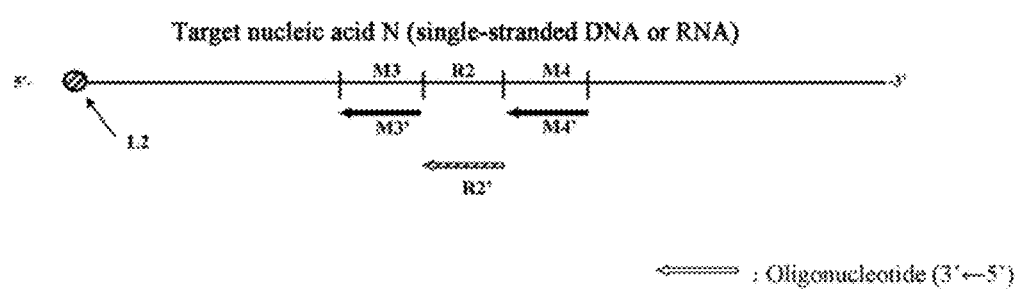

FIG. 3-4 schematically shows the principle of embodiments included in Embodiments [46] and [47] exemplified above (which correspond to embodiments (q) and (r) in Table 1 described below, respectively).

Figures 3, 4, 5:
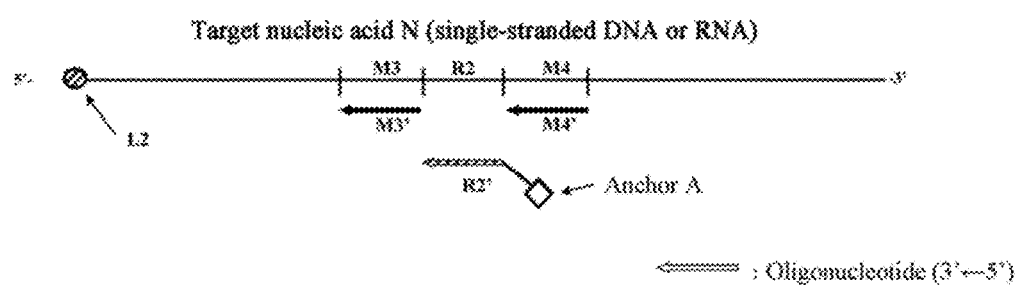

FIG. 3-5 schematically shows the principle of the embodiments included in [48] to [52] exemplified above (which correspond to embodiments (s) to (v) in Table 1 described below, respectively).

FIG. 4-1 schematically shows the principle of embodiments included in Embodiment [11] exemplified above (which corresponds to embodiment (d) in Table 1 described below).

FIG. 4-2 schematically shows the principle of embodiments included in Embodiment [9] exemplified above (which corresponds to embodiment (b) in Table 1 described below).

FIG. 4-3 schematically shows the principle of embodiments included in Embodiment [19] exemplified above (which corresponds to embodiment (1) in Table 1 described below).

FIG. 4-4 schematically shows the principle of embodiments included in Embodiment [18] exemplified above (which corresponds to embodiment (k) in Table 1 described below).

FIG. 4-5 schematically shows the principle of embodiments included in Embodiment [38] exemplified above (which corresponds to embodiment (p) in Table 1 described below).

Figures 1, 4:
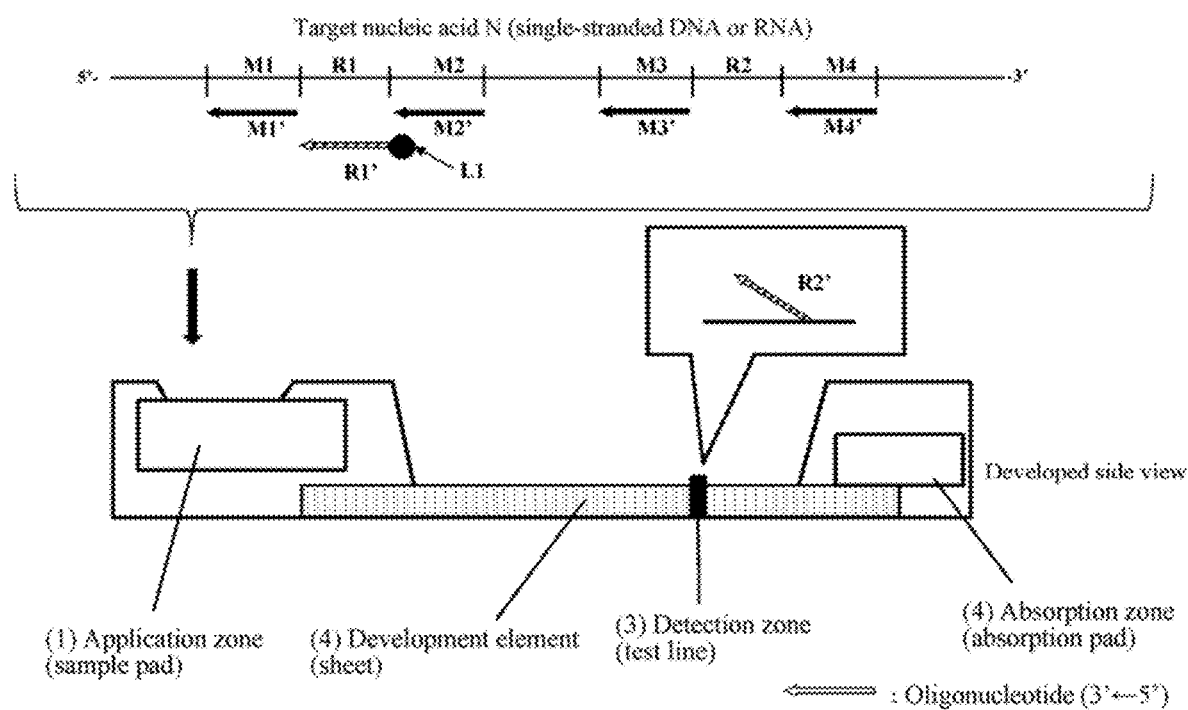
Figures 2, 4:
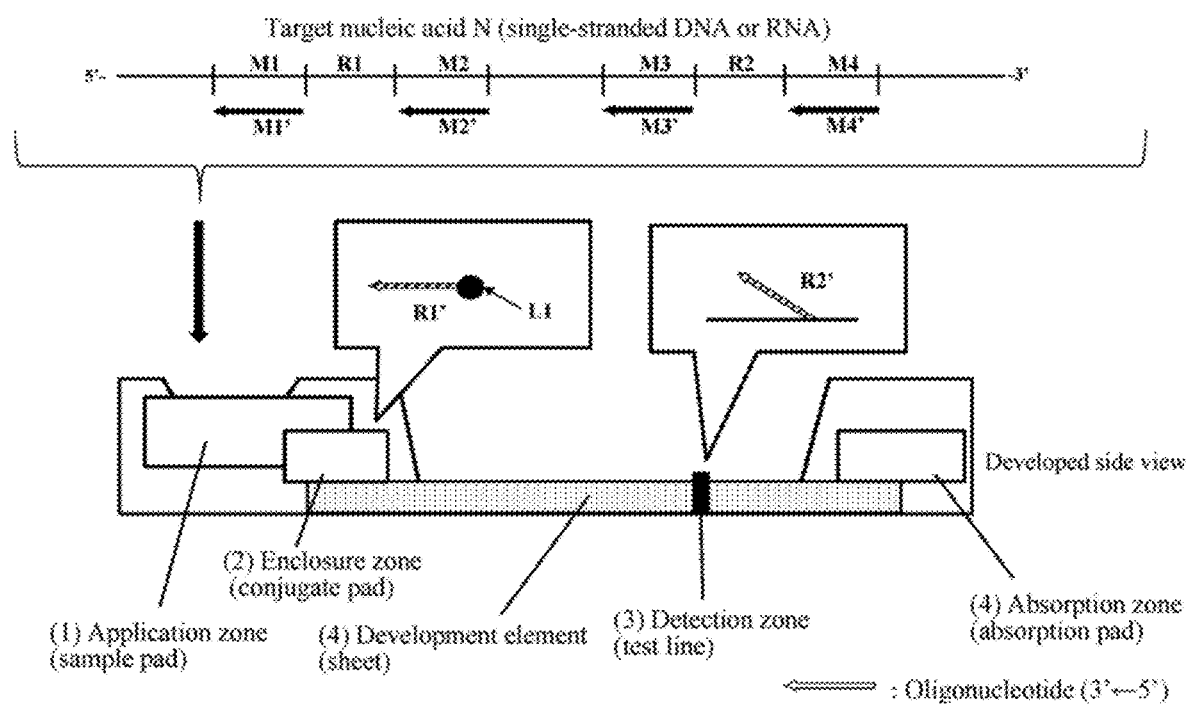
Figures 3, 4:
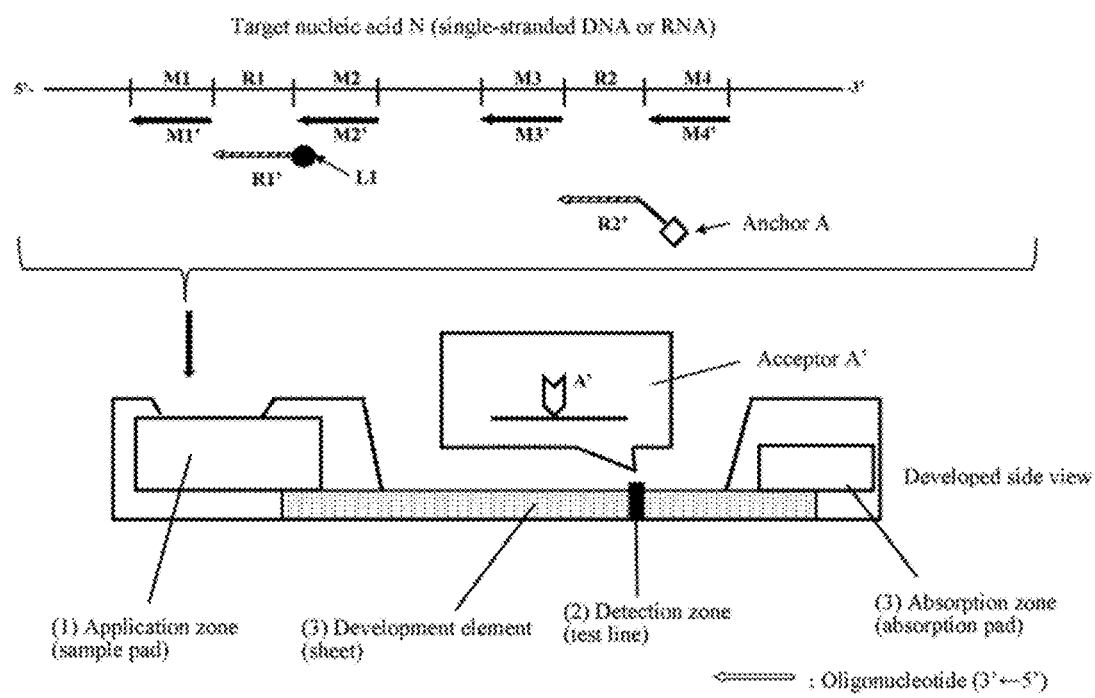
Figure 4:
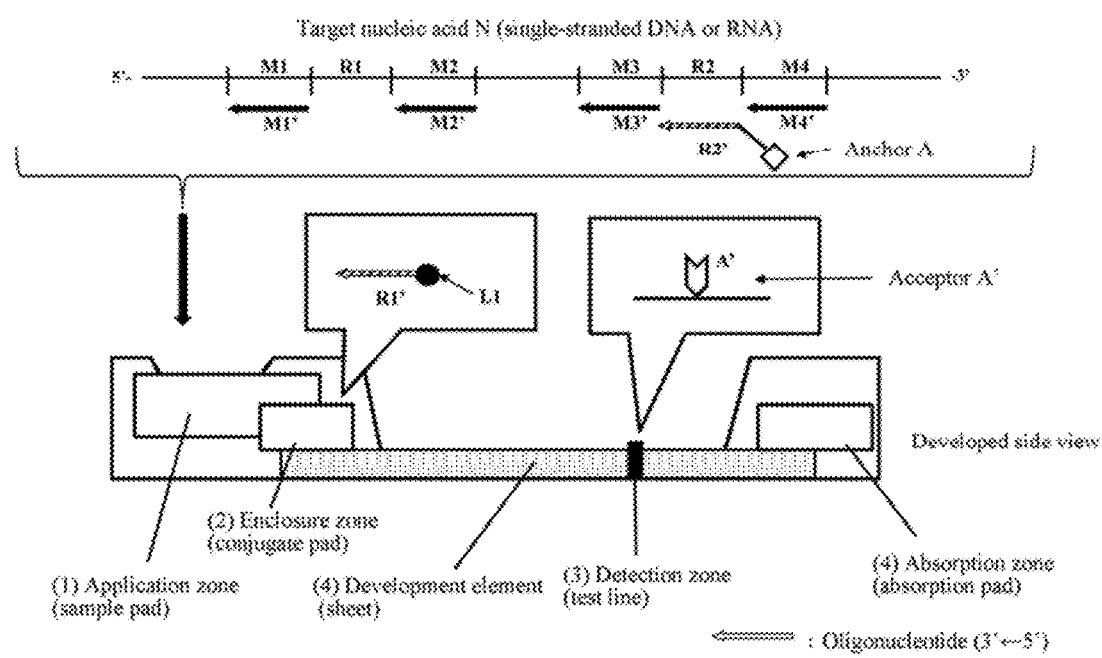
Figures 4, 5:
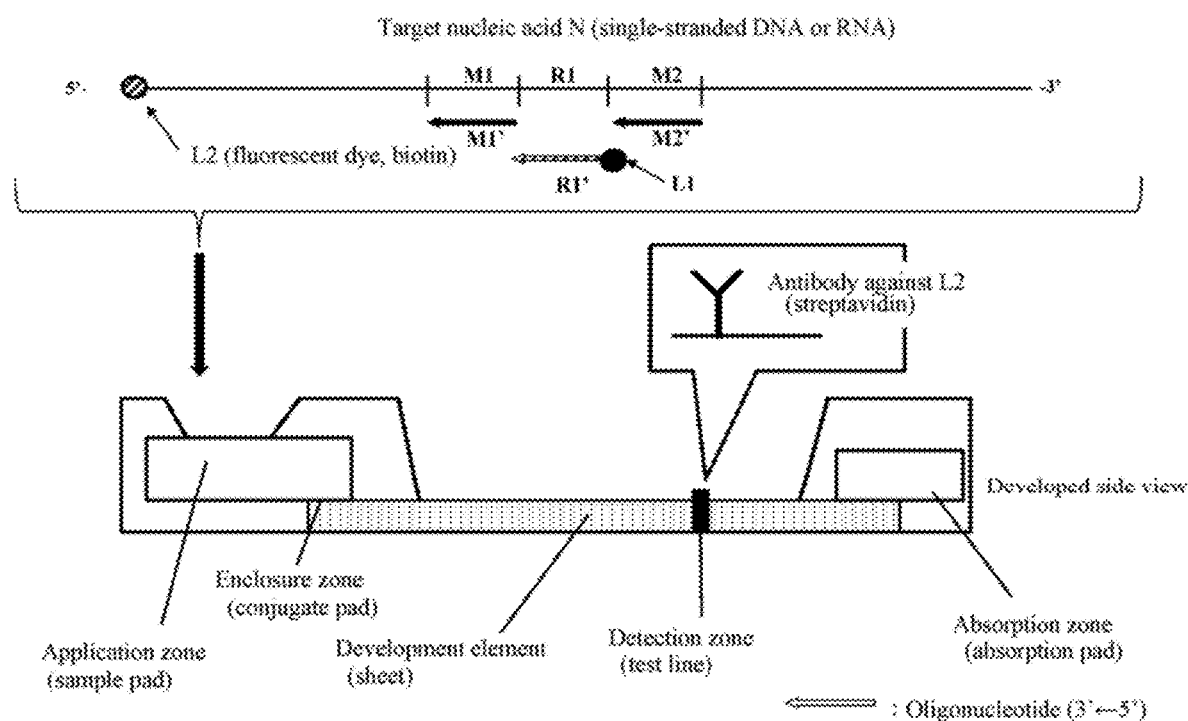
Figures 4, 5, 6:
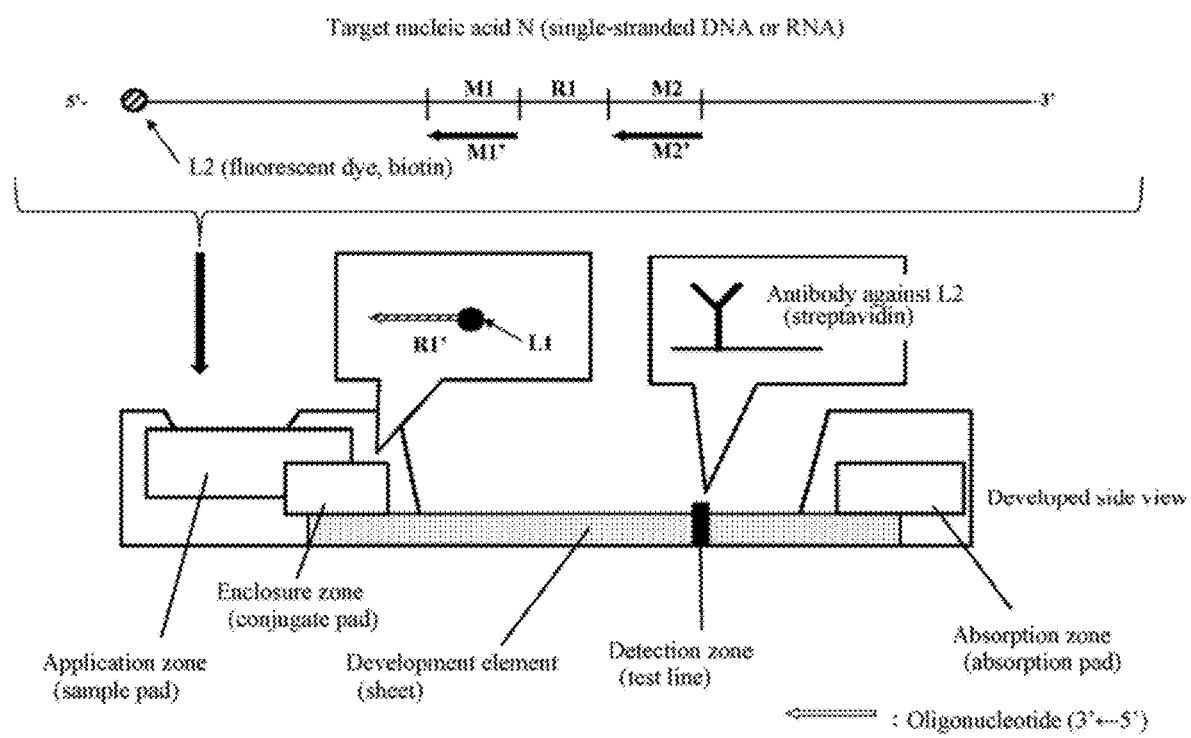

FIG. 4-6 schematically shows the principle of embodiments included in Embodiment [36] exemplified above (which corresponds to embodiment (n) in Table 1 described below).

FIG. 4-7 schematically shows the principle of embodiments included in Embodiment [51] exemplified above (which corresponds to embodiment (v) in Table 1 described below).

FIG. 4-8 schematically shows the principle of embodiments of hybridization-ELISA included in Embodiment [40] exemplified above (which corresponds to embodiment (v) in Table 1 described below).

FIG. 4-9 schematically shows the principle of embodiments included in Embodiment [23] exemplified above (which corresponds to embodiments (e) to (1) in Table 1 described below, where two or more different target nucleic acids are included in the sample).

FIG. 4-10 schematically shows the principle of embodiments included in Embodiment [39] exemplified above (which corresponds to embodiments (m) to (p) in Table 1 described below, where two or more different target nucleic acids are included in the sample).

FIG. 4-11 schematically shows the principle of embodiments included in Embodiment [52] exemplified above (which corresponds to embodiments (s) to (v) in Table 1 described below, where two or more different target nucleic acids are included in the sample).

FIG. 4-12 schematically shows the principle of embodiments included in Embodiment [53] exemplified above (which corresponds to embodiments (s) to (v) in Table 1 described below, where two or more different target nucleic acids are included in the sample).

FIG. 5-1 schematically shows an exemplary embodiment of a device containing the developing element in the form of a sheet, which is used for carrying out nucleic acid chromatography in the present invention, and the case (housing) in which the device is placed.

FIG. 5-2 schematically shows an exemplary embodiment of a device containing the developing element in the form of a sheet, which is used for carrying out nucleic acid chromatography in the present invention (the device is equipped with a detection zone as the test line for detecting the target nucleic acid, and also a detection zone as the control line for detecting the nucleic acid used as an internal control to confirm whether the device functions normally), and the case (housing) in which the device is placed.

FIG. 6 shows the result of detection by agarose gel electrophoresis of PCR products obtained using the respective genomic DNAs of *Staphylococcus aureus* (abbreviated as "SA", strain ATCC12600), *Staphylococcus epidermidis* (abbreviated as "SE", strain ATCC14990), *Pseudomonas aeruginosa* (abbreviated as "PA", strain JCM5962), *Enterococcus faecalis* (abbreviated as "EF", strain JCM5803), *Escherichia coli* (abbreviated as "EC", strain JCM1649), *Enterobacter cloacae* (abbreviated as "ET", strain JCM1232), and *Klebsiella pneumoniae* (abbreviated as "KP", strain JCM 1662) as templates.

In the figure, M indicates the molecular weight marker, and the values on the left indicate the molecular weights (bp).

Figures 4, 5, 6, 7:
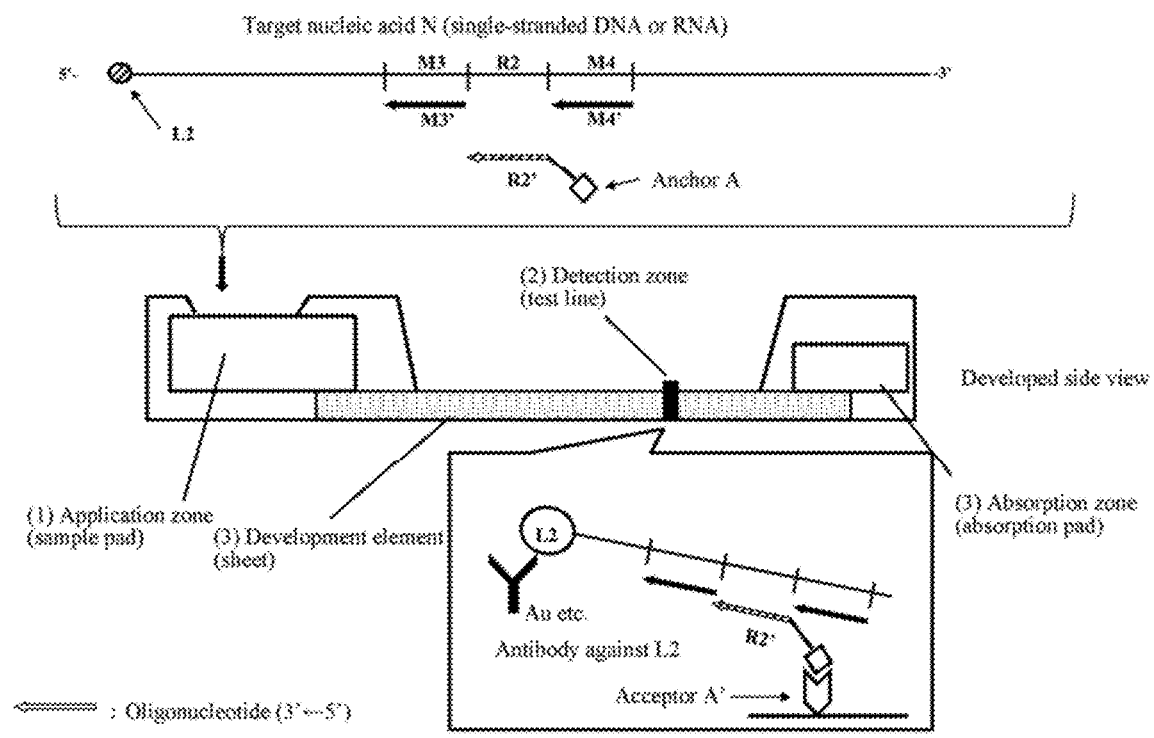

FIG. 7 shows the result of detection of PCR products obtained using the respective genomic DNAs of *Staphylococcus aureus* (abbreviated as "SA", strain ATCC12600), *Staphylococcus epidermidis* (abbreviated as "SE", strain ATCC14990), *Pseudomonas aeruginosa* (abbreviated as "PA", strain JCM5962), *Enterococcus faecalis* (abbreviated as "EF", strain JCM5803), *Escherichia coli* (abbreviated as "EC", strain JCM1649), *Enterobacter cloacae* (abbreviated as "ET", strain JCM1232), and *Klebsiella pneumoniae* (abbreviated as "KP", strain JCM 1662) as templates, where the PCR products were subjected to the nucleic acid chromatography of the present invention using mask oligonucleotides, and nucleic acid chromatography using no mask oligonucleotide.

Figures 4, 5, 6, 7, 8:
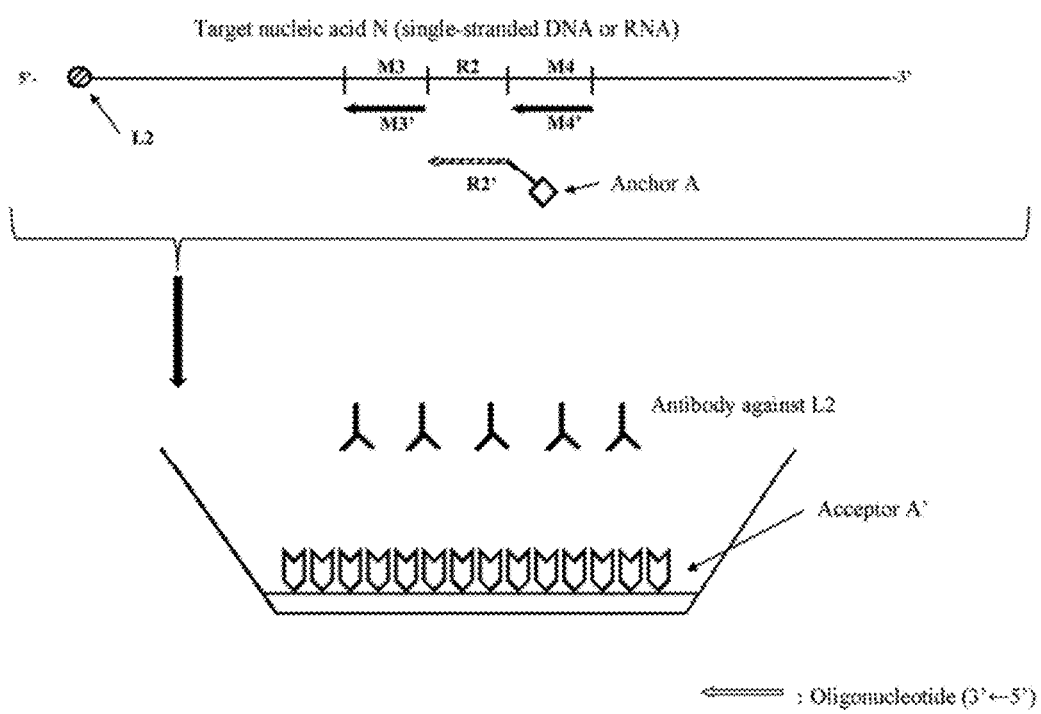

FIG. 8 shows the result of detection of genome fragments produced by restriction enzyme treatment of the genomic DNAs of *Enterobacter cloacae* (abbreviated as "ET", strain JCM1232) and *Escherichia coli* (abbreviated as "EC", strain JCM1649), where the genome fragments were subjected to nucleic acid chromatography using mask oligonucleotides of the present invention designed to hybridize specifically to ET.

Figures 4, 5, 6, 7, 8, 9:
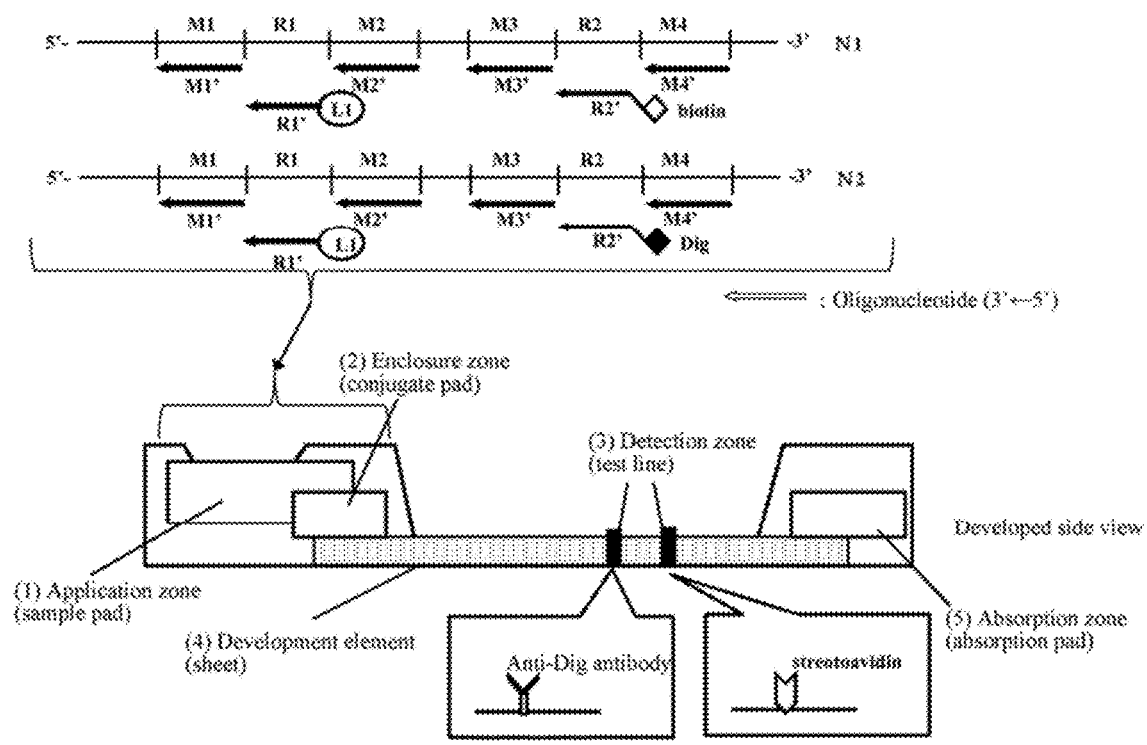

FIG. 9 shows the result of detection by agarose gel electrophoresis of PCR products obtained by multiplex PCR using the respective genomic DNAs of *Campylobacter jejuni* (strain ATCC700819), *Campylobacter jejuni* (strain 81-176), *Campylobacter coli* (strain ATCC33559), *Campylobacter coli* (strain ATCC43478), *Campylobacter fetus* (strain ATCC27374), *Campylobacter fetus* (strain ATCC19438), *Campylobacter hyointestinalis* (strain ATCC35217), *Campylobacter lari* (strain ATCC43675) and *Campylobacter upsaliensis* (strain ATCC43956) as templates.

Figures 4, 5, 6, 7, 8, 9, 10:
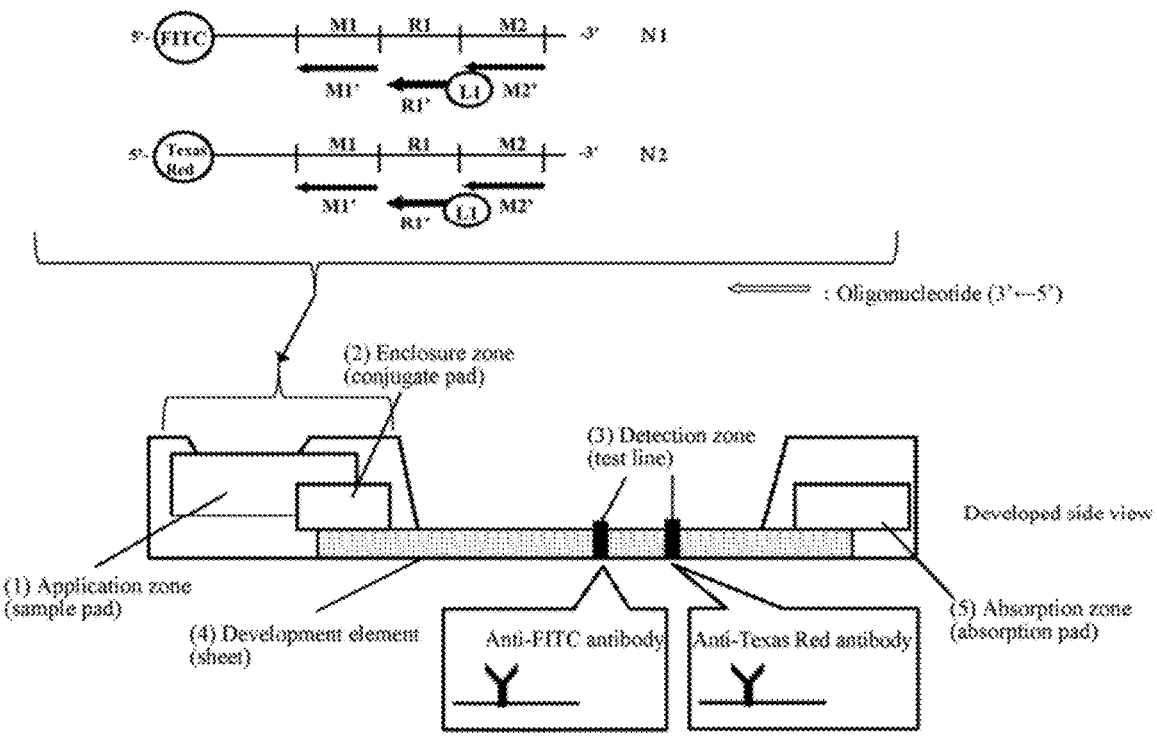

FIG. 10 shows the result of detection of PCR products obtained by multiplex PCR using the respective genomic DNAs of *Campylobacter jejuni* (strain ATCC700819), *Campylobacter jejuni* (strain 81-176), *Campylobacter coli* (strain ATCC33559), *Campylobacter coli* (strain ATCC43478), *Campylobacter fetus* (strain ATCC27374), *Campylobacter fetus* (strain ATCC19438), *Campylobacter hyointestinalis* (strain ATCC35217), *Campylobacter lari* (strain ATCC43675), *Campylobacter upsaliensis* (strain ATCC43956), and *Escherichia coli* (strain C600) as templates, where the PCR products were subjected to the nucleic acid chromatography of the present invention using mask oligonucleotides, and nucleic acid chromatography using no mask oligonucleotide.

Figures 4, 5, 6, 7, 8, 9, 10, 11:
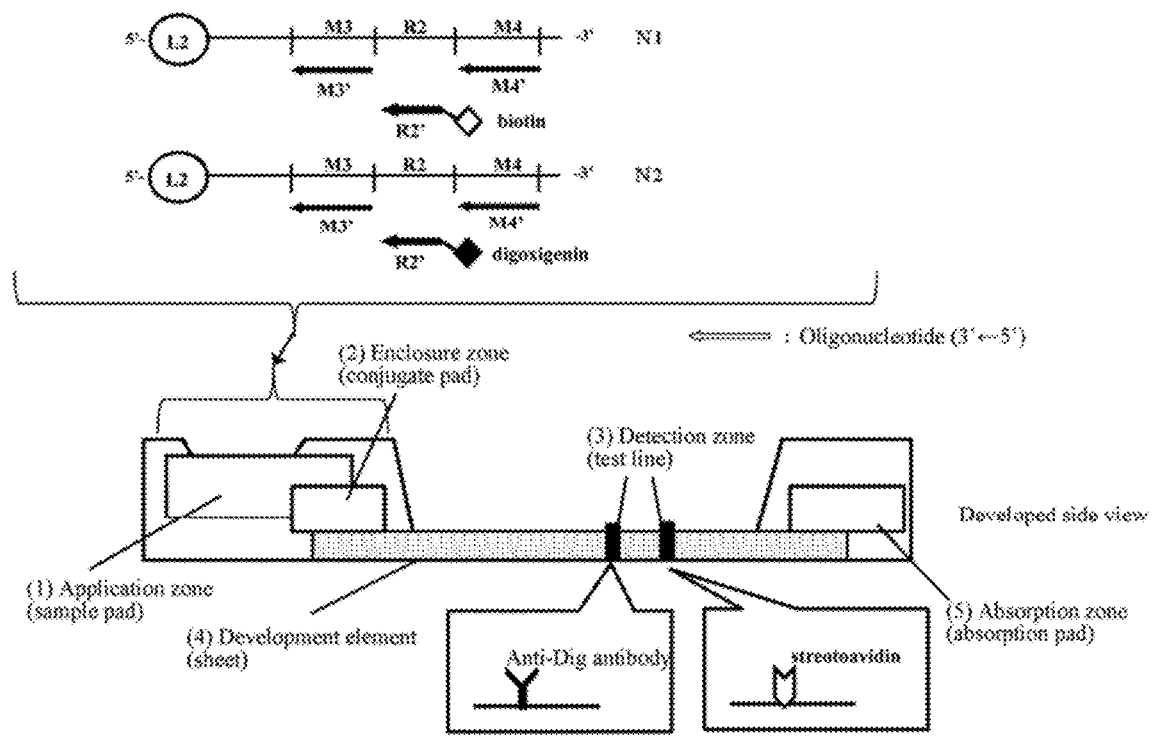

FIG. 11 shows the result of comparing the effect of mask oligonucleotides on detection sensitivity in the nucleic acid chromatography of the present invention using mask oligonucleotides.

Figures 4, 5, 6, 7, 8, 9, 10, 11, 12:
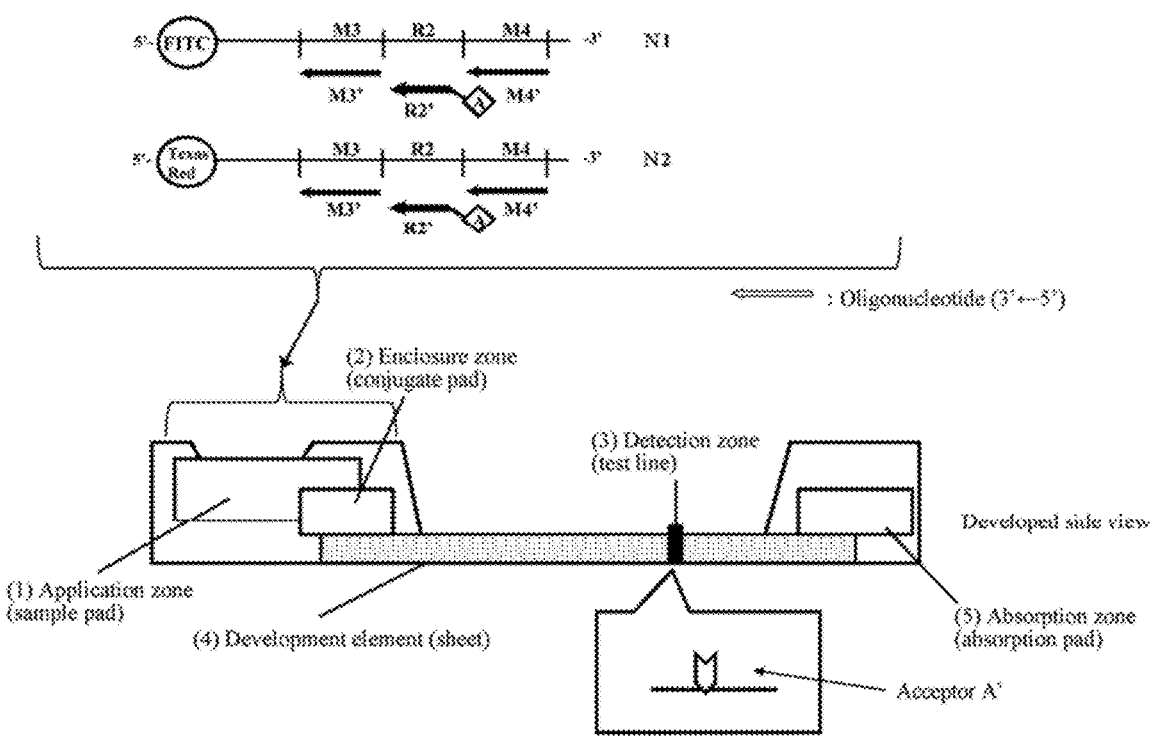
Figures 1, 5:
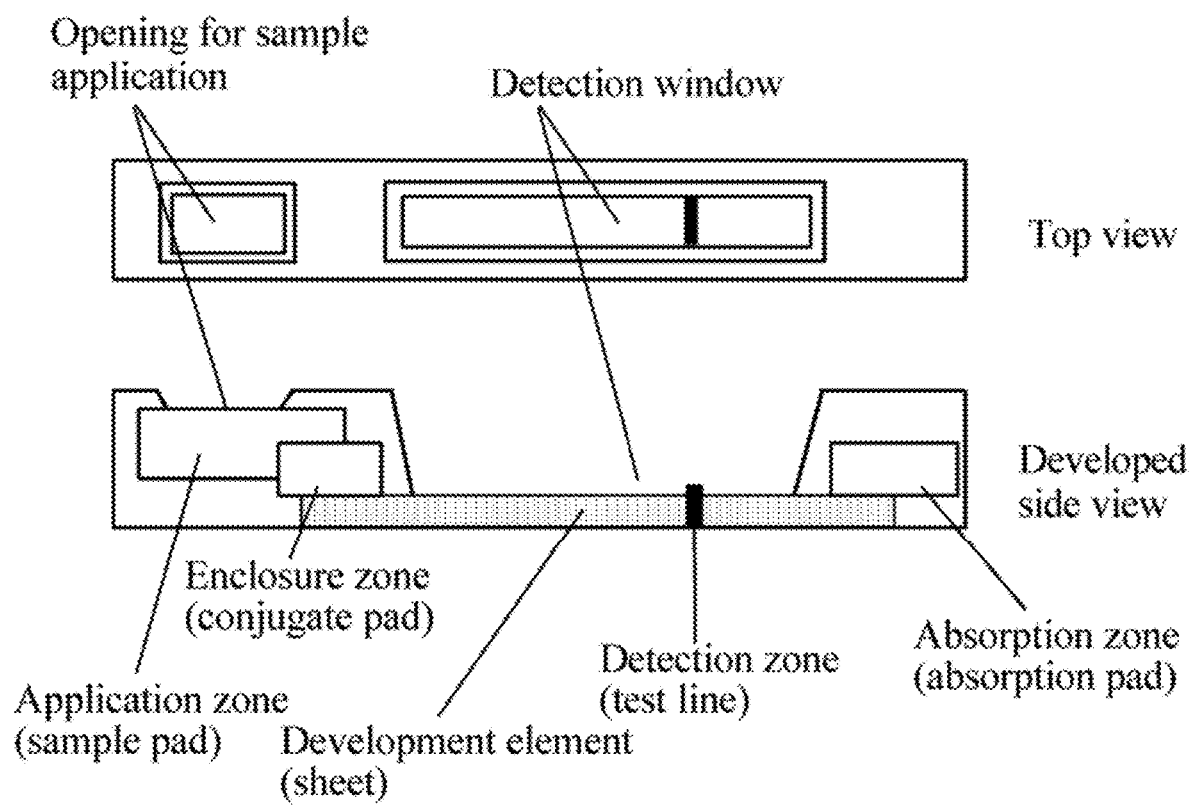
Figures 2, 5:
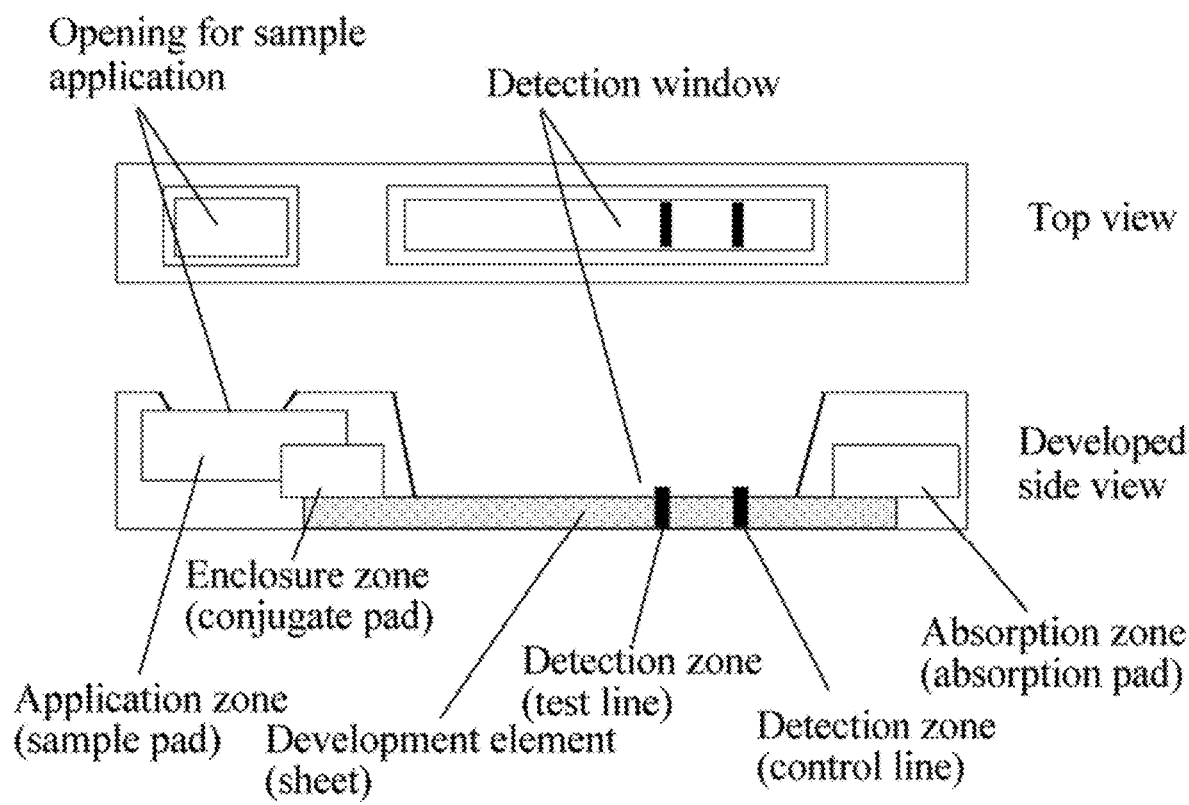
Figure 7:
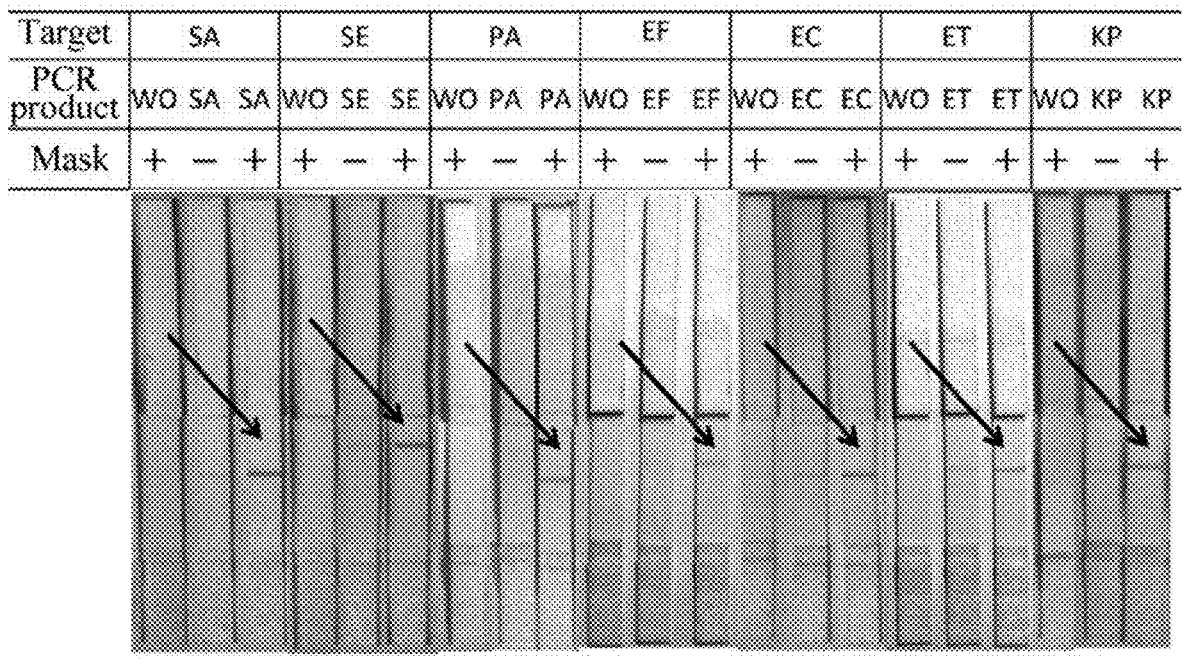
Figure 8:
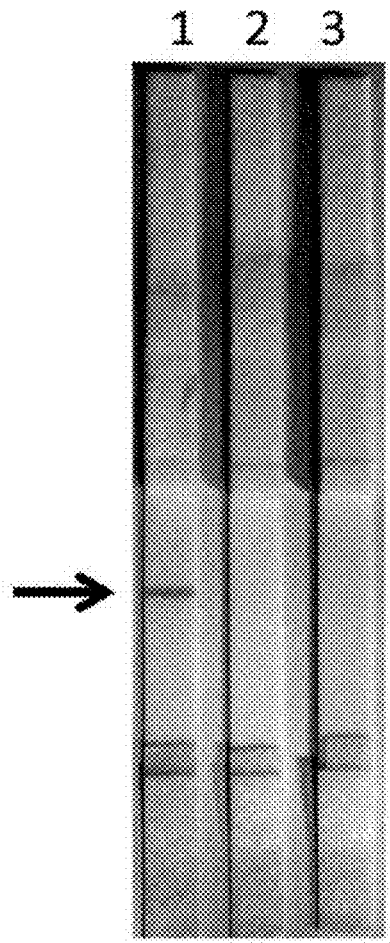
Figure 9:
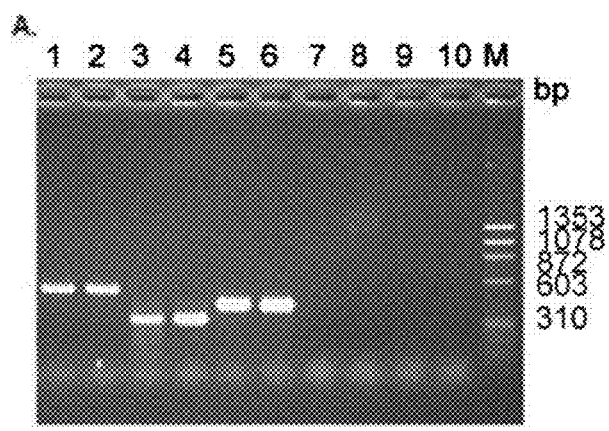
Figure 10:
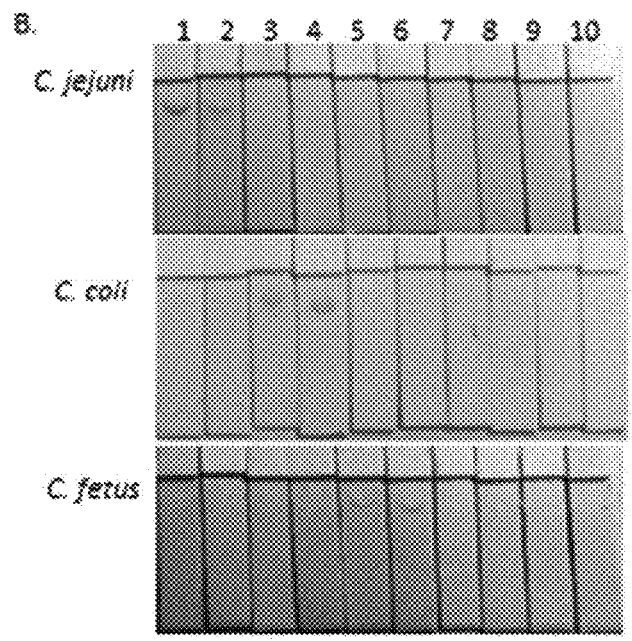
Figure 11:
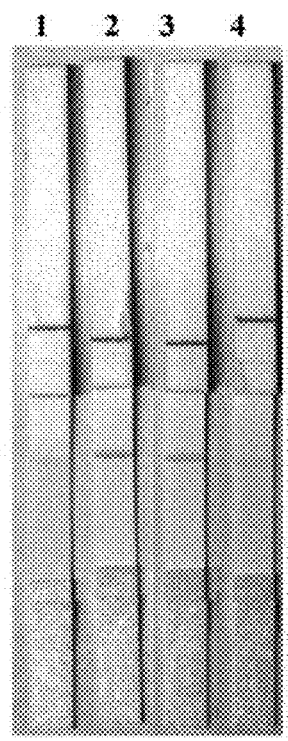
Figure 12:
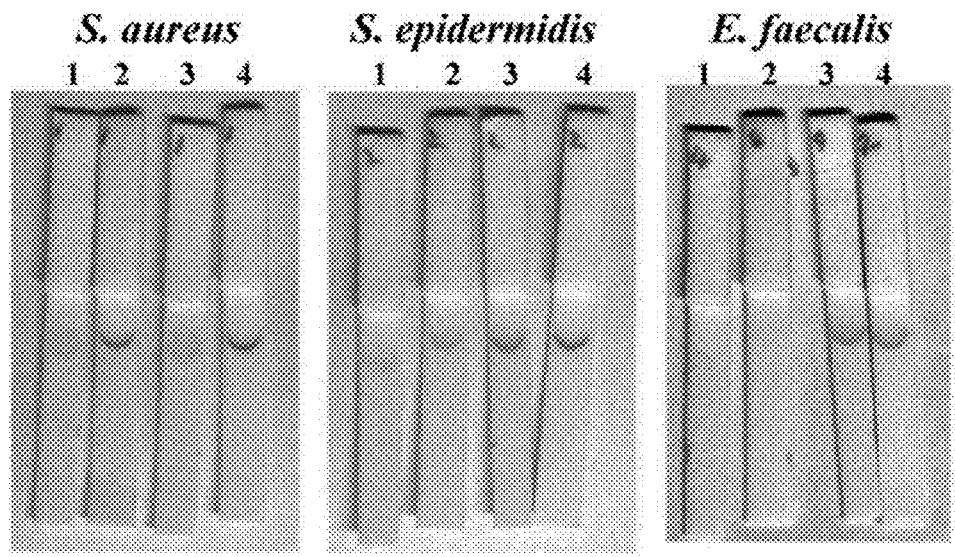

FIG. 12 shows the result of comparing the detection sensitivity in the nucleic acid chromatography of the present invention using mask oligonucleotides depending on the embodiments of the use of mask oligonucleotides.

Figure 13:
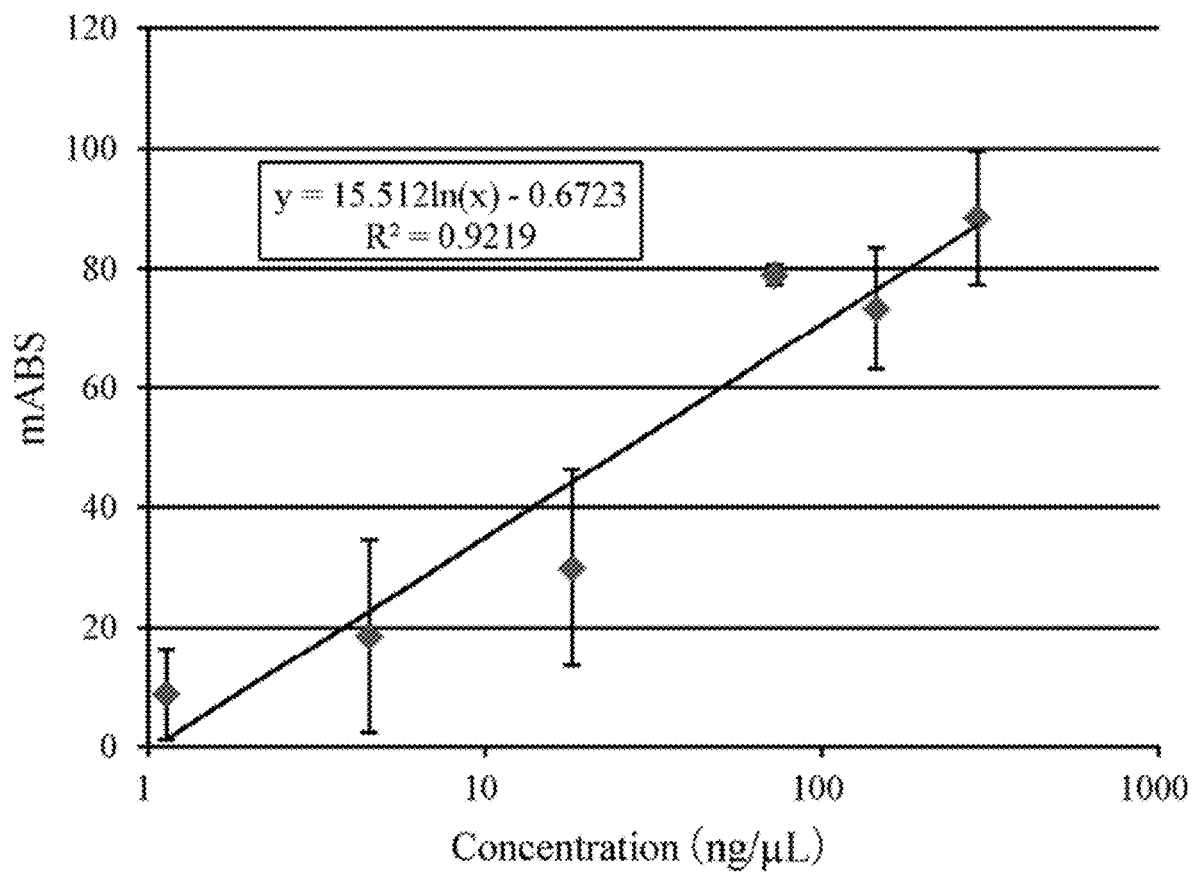

FIG. 13 shows the quantitativeness of the nucleic acid chromatography of the present invention using mask oligonucleotides.

Figure 14:
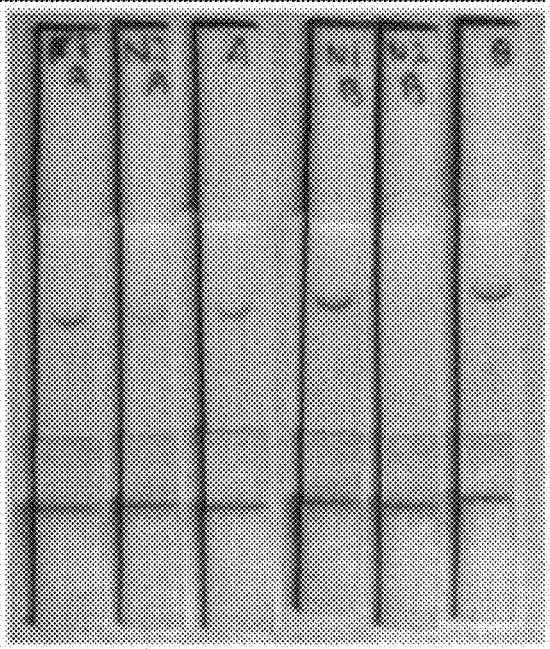

FIG. 14 shows the result of comparing the detection sensitivity in the nucleic acid chromatography using mask oligonucleotides depending on the embodiments of the use of mask oligonucleotides.

Figure 15:
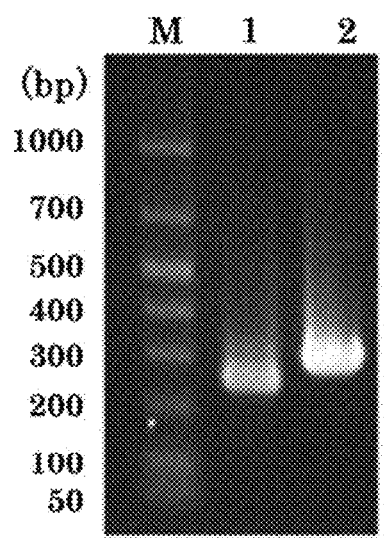

FIG. 15 shows the result of detection by agarose gel electrophoresis of PCR products obtained using the genomic DNAs of human β globin and *Escherichia coli* (abbreviated as "EC", strain JCM1649) as templates.

In the figure, M indicates the molecular weight marker, and the values on the left indicate molecular weights (bp).

FIG. 16 shows the result of detection of PCR products obtained using the 16S rRNAs of the respective bacteria as templates, where the PCR products were subjected to the nucleic acid chromatography of the present invention using mask oligonucleotides.

Figure 17:
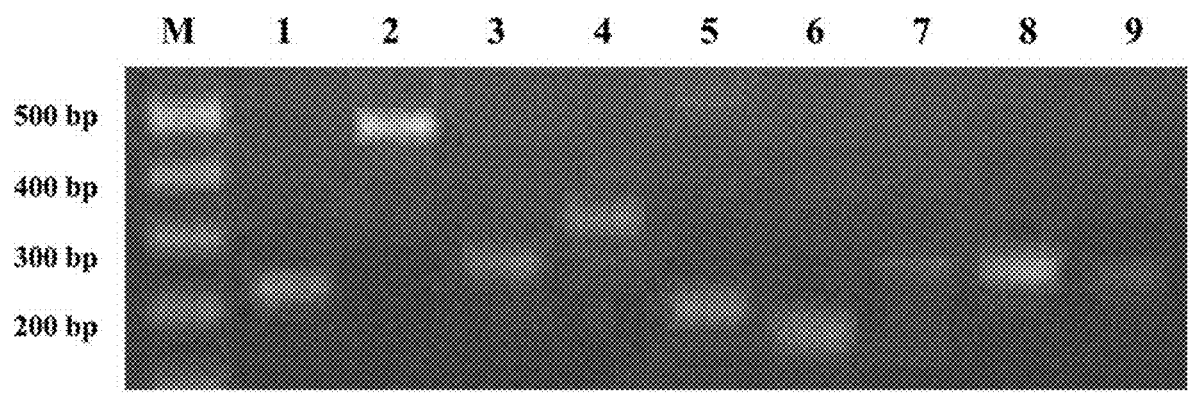

FIG. 17 shows the result of detection by agarose gel electrophoresis of PCR products obtained using the ITS regions of the genomic DNAs of the respective *Candida* bacteria as templates.

Figure 18:
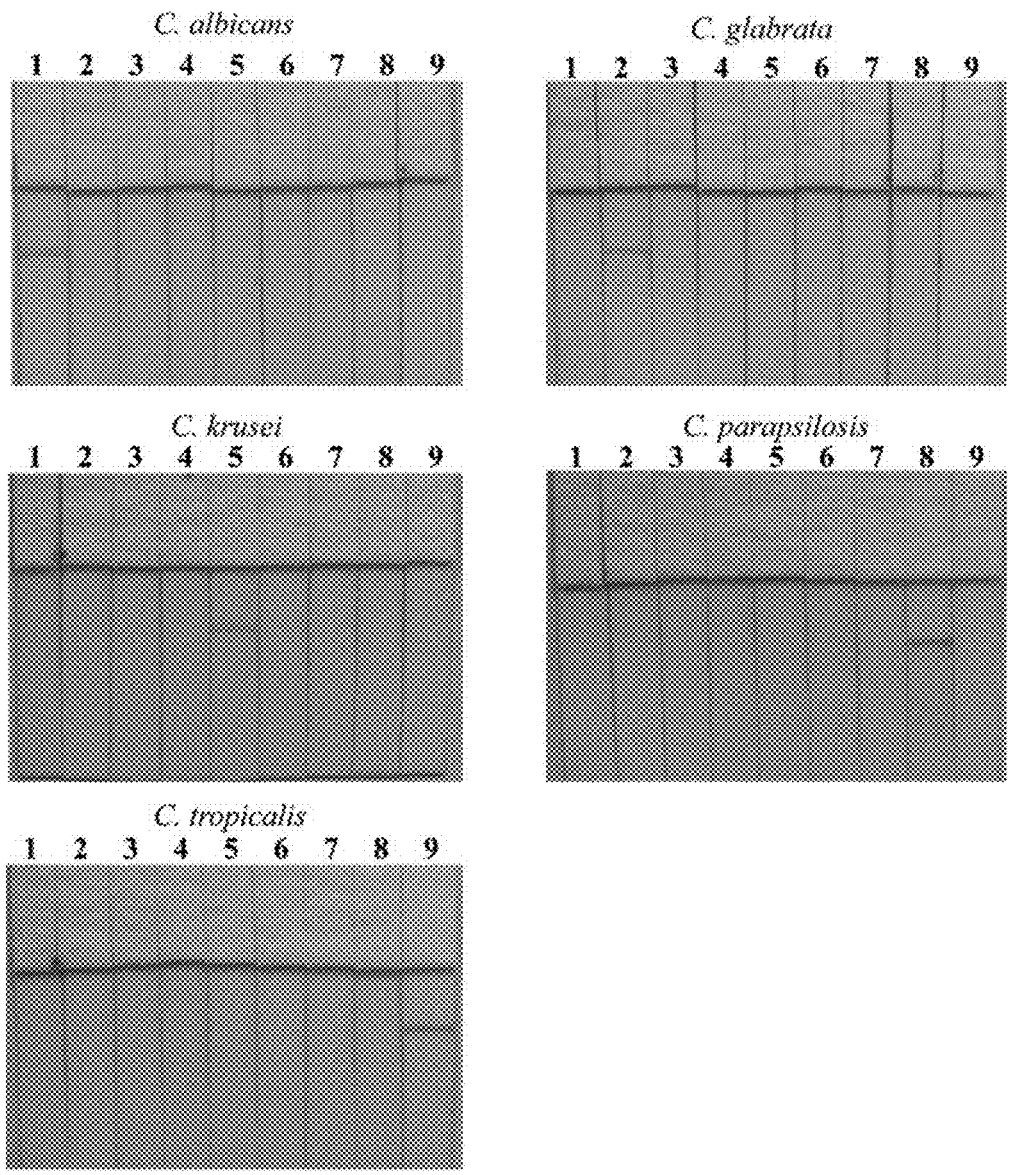

FIG. 18 shows the result of detection of PCR products obtained using the ITS regions of the genomic DNAs of the respective *Candida* bacteria as templates, where the PCR products were subjected to the nucleic acid chromatography of the present invention using mask oligonucleotides.

MODE FOR CARRYING OUT THE INVENTION

The present invention is as exemplified above in [1] to [68], and provides methods for detecting or quantifying nucleic acids by immunoassay or nucleic acid chromatography using mask oligonucleotides of the present invention, and devices and kits for use in these methods.

All prior art documents cited in the present specification are incorporated herein by reference.

The methods of the present invention are characterized in adopting the respective principles (1) to (7) of the method for capturing and detecting target nucleic acids which are schematically shown in FIG. 2 mentioned above. Each of the embodiments includes the embodiments exemplified in Table 1 shown below.

TABLE 1

| FIG. 2 | Embodiment | Applied sample containing target nucleic acid (mixture) | | | | Oligonucleotide enclosed in application zone or enclosing zone | | | Immobilized on detection zone | Indicator for detection |
|---|---|---|---|---|---|---|---|---|---|---|
| (1) | (a) | Target nucleic acid N | | | | Mask oligo M | L1-labeled oligo R1 | | Oligo R2 | L1 |
| (2) | (b) | Target nucleic acid N | Mask oligo M' | | | | L1-labeled oligo R1' | | Oligo R2' | L1 |
| | (c) | Target nucleic acid N | | L1-labeled oligo R1' | | Mask oligo M' | | | Oligo R2' | L1 |
| | (d) | Target nucleic acid N | Mask oligo M' | L1-labeled oligo R1' | | | | | Oligo R2' | L1 |
| (3) | (e) | Target nucleic acid N | | | | Mask oligo M' | L1-labeled oligo R1' | Anchor A oligo R2' | Acceptor A' | L1 |
| | (f) | Target nucleic acid N | Mask oligo M' | | | | L1-labeled oligo R1' | Anchor A oligo R2' | Acceptor A' | L1 |
| | (g) | Target nucleic acid N | Mask oligo M' | L1-labeled oligo R1' | | | | Anchor A oligo R2' | Acceptor A' | L1 |
| | (h) | Target nucleic acid N | | L1-labeled oligo R1' | | Mask oligo M' | | Anchor A oligo R2' | Acceptor A' | L1 |
| | (i) | Target nucleic acid N | | L1-labeled oligo R1' | Anchor A oligo R2' | Mask oligo M' | | | Acceptor A' | L1 |
| | (j) | Target nucleic acid N | | | Anchor A oligo R2' | Mask oligo M' | L1-labeled oligo R1' | | Acceptor A' | L1 |
| | (k) | Target nucleic acid N | Mask oligo M' | | Anchor A oligo R2' | | L1-labeled oligo R1' | | Acceptor A' | L1 |
| | (l) | Target nucleic acid N | Mask oligo M' | L1-labeled oligo R1' | Anchor A oligo R2' | | | | Acceptor A' | L1 |
| (4) | (m) | L2-labeled target nucleic acid N | | | | Mask oligo M' | L1-labeled oligo R1' | | Substance that binds in L2 | L1 |
| | (n) | L2-labeled target nucleic acid N | Mask oligo M' | | | | L1-labeled oligo R1' | | Substance that binds in L2 | L1 |

TABLE 1-continued

| FIG. 2 | Embodiment | Applied sample containing target nucleic acid (mixture) | | | Oligonucleotide enclosed in application zone or enclosing zone | | Immobilized on detection zone | Indicator for detection |
|---|---|---|---|---|---|---|---|---|
| | (o) | L2-labeled target nucleic acid N | | L1-labeled oligo R1' | Mask oligo M' | | Substance that binds in L2 | L1 |
| | (p) | L2-labeled target nucleic acid N | Mask oligo M' | L1-labeled oligo R1' | | | Substance that binds in L2 | L1 |
| (5) (6) | (q) | L2-labeled target nucleic acid N | | | Mask oligo M' | | Oligo R2 | L2 |
| | (r) | L2-labeled target nucleic acid N | Mask oligo M' | | | | Oligo R2 | L2 |
| (7) | (s) | L2-labeled target nucleic acid N | | | Mask oligo M' | Anchor A oligo R2' | Acceptor A' | L2 |
| | (t) | L2-labeled target nucleic acid N | Mask oligo M' | | | Anchor A oligo R2' | Acceptor A' | L2 |
| | (u) | L2-labeled target nucleic acid N | | Anchor A oligo R2' | Mask oligo M' | | Acceptor A' | L2 |
| | (v) | L2-labeled target nucleic acid N | Mask oligo M' | Anchor A oligo R2' | | | Acceptor A' | L2 |

Embodiments (a) to (d) in Table 1 correspond to the above-described Embodiments [8] to [11] (and [23]), respectively.

Embodiments (e) to (1) in Table 1 correspond to the above-described Embodiments [12] to [19] (and [23]), respectively.

Embodiments (m) to (p) in Table 1 correspond to the above-described Embodiments [35] to [38] (and [39]), respectively.

Embodiments (q) and (r) in Table 1 correspond to the above-described Embodiments [46] and [47], respectively.

Embodiments (s) to (v) in Table 1 correspond to the above-described Embodiments [48] to [51] (and [52]), respectively.

"Sample" as used in the present invention means a living body or a portion thereof (organ, tissue, body fluid, organ or component; embryo/fetus, seed, egg, egg cell or sperm; excrement; or a portion thereof, etc.) of any organism (animals, plants, microorganisms, bacteria, etc.) or virus, processed products thereof, or any preparation (solution, suspension, culture medium, culture supernatant, centrifuge supernatant, centrifuge residue, or such) containing the later-described "nucleic acids" (genomic DNA, cDNA, mRNA, tRNA, rRNA, etc.) derived from any of them or fragments thereof.

The organism described above includes eukaryotes (such as animals, plants, fungi (a synonym for mycetes; such as molds, yeasts, and mushrooms), algae, and protists (protozoa)), prokaryotes (such as bacteria, archaebacteria, actinomycetes, and cyanobacteria), and microorganisms.

"Animals" in the present invention include, for example, vertebrates (such as mammals, birds, reptiles, amphibians, fish, and jawless vertebrates) and invertebrates, but are not limited thereto. The animals also include genetically engineered animals.

"Plants" in the present invention include, for example, seed plants, pteridophytes, bryophytes, *Streptophyta*, green plants, *Archaeplastida*, and bikonts, but are not limited thereto. The plants also include genetically engineered plants.

"Microorganisms" in the present invention include, for example, prokaryotes (eubacteria (bacteria), archaebacteria), algae, protists, fungi, slime molds, mycetes, and protozoa, but are not limited thereto. The microorganisms also include genetically engineered microorganisms.

Examples of fungi include, for example, *Candida, Aspergillus, Cryptococcus, Mucor, Pneumocystis, Trichophyton*, and *Trichosporon*, but are not limited thereto.

Examples of protozoa include, for example, *Cryptosporidium, Cyclospora, Kudoa (Sarcosporidia)*, amebic dysentery, *Sarcocystis, Leishmania, Toxoplasma*, and *Trypanosoma*, but are not limited thereto.

"Bacteria" in the present invention include, for example, any bacteria (for example, eubacteria such as gram-positive bacteria and gram-negative bacteria) classified according to the International Code of Nomenclature of Bacteria, but are not limited thereto. The bacteria also include genetically engineered bacteria.

Examples of bacteria include, but are not limited to, for example, *Staphylococcus, Streptococcus, Escherichia, Enterobacter, Haemophilus, Klebsiella, Pseudomonas, Campylobacter, Bacteroides, Serratia, Acinetobacter, Mycoplasma, Mycobacterium, Clostridium, Bacillus, Proteus, Neisseria, Salmonella, Shigella, Vibrio, Aeromonas, Yersinia, Listeria, Cronobacter, Citrobacter, Brucella, Pasteurella, Helicobacter, Moraxella, Legionella, Treponema, Rickettsia, Chlamydia, Enterococcus, Burkholderia, Stenotrophomonas, Edwardsiella, Hafnia, Kluyvera, Morganella, Pantoea, Providencia, Corynebacterium, Micrococcus, Sphingobacterium, Brevundimonas, Achromobacter, Alcaligenes, Chromobacterium, Porphyromonas, Prevotella, Fusobacterium, Lactobacillus, Peptomphilus, Eggerthella, Propionibacterium, Capnocytophaga, Haemophilus*, and *Gardnerella*.

"Viruses" in the present invention include, for example, any viruses classified by the International Committee on Taxonomy of Viruses, and their mutants, but are not limited thereto. For example, any viruses classified as double-stranded DNA viruses, single-stranded DNA viruses, double-stranded RNA viruses, single-stranded RNA (+strand) viruses, single-stranded RNA (−strand) viruses, single-stranded RNA (reverse transcribing) viruses, or double-stranded DNA (reverse transcribing) viruses are included. The viruses also include genetically engineered viruses.

Examples of viruses include, but are not limited to, for example, human immunodeficiency virus, human T-lymphotropic virus, cytomegalovirus, herpesvirus, EB virus, influenza virus, hepatitis virus, norovirus, rotavirus, adenovirus, astrovirus, papillomavirus, RS virus, mumps virus, coronavirus, rubivirus, and SARS virus.

"Nucleic acids" in the present invention means any naturally-occurring or artificially prepared nucleic acids (genomic DNA, cDNA, mitochondrial DNA (mtDNA), mRNA, tRNA, rRNA, short interfering (siRNA), shRNA (short hairpin RNA), miRNA (micro RNA), snRNA (small nuclear RNA), tmRNA (transfer messenger RNA), and such) or fragments thereof.

For example, when the target nucleic acid (that is, target nucleic acid N) is derived from prokaryotic bacteria, the nucleic acid may be the 23S, 16S, or 5S subunit of the bacterial rRNA gene. When the target nucleic acid (that is, target nucleic acid N) is derived from fungi, which are eukaryotes, the nucleic acid may be the 28S, 18S, 5.8S, or 5S subunit of the fungal rRNA gene, or an internal transcribed spacer (ITS) region or intergenic spacer (IGS) region in their vicinity.

The nucleic acid may be either double-stranded or single-stranded. When it is double-stranded, it can be made into single strands by "denaturation" described later.

The nucleic acid also includes those with secondary or tertiary structures such as intramolecular loops by self-association. Such higher-order structures can be eliminated by "denaturation" described later or by other conventional methods.

The naturally-occurring nucleic acids are derived from the above-mentioned organisms, bacteria, viruses, or such, and include, but are not limited to, nucleic acids obtained from the living bodies of those organisms, bacteria, or viruses or portions thereof, and nucleic acids artificially amplified and prepared from such obtained nucleic acids by enzyme reactions (DNA polymerase, RNA polymerase, reverse transcriptase, and such).

The amplification and preparation of nucleic acids by enzyme reactions can be performed by polymerase chain reaction (PCR), loop-mediated isothermal amplification (LAMP), transcription-mediated amplification (TMA), transcription-reverse transcription concerned reaction (TRC), ligase chain reaction (LCR), standard displacement amplification (SDA), nucleic acid sequence-based amplification (NASBA), or such (Rinsho Igaku, Vol. 36, p. 19-24, 2007).

The artificially amplified and prepared nucleic acids also include any nucleic acids prepared using a DNA/RNA synthesizer based on the nucleotide sequences designed according to the purpose.

In this invention, the nucleic acids amplified and prepared by a method such as PCR, LAMP, TMA, TRC, LCR, SDA, or NASBA mentioned above include nucleic acids amplified and prepared under any conditions (concentration of each primer, salt concentration, reaction time, reaction temperature, reaction cycles, and such) in the method. For example, if the concentration of each primer in the nucleic acid amplification by PCR is taken as an example, the concentrations of a pair of or two or more pairs of primers used in PCR (forward primer and reverse primer) may be the same or different (asymmetric PCR).

Nucleic acids in the present invention may have any size and nucleotide length; and may be, for example, approximately 50 bp to approximately 100,000 bp, approximately 50 to approximately 50,000 bp, approximately 50 to approximately 10,000 bp, approximately 50 to approximately 5,000 bp, approximately 100 to approximately 100,000 bp, approximately 100 to approximately 50,000 bp, approximately 100 to approximately 10,000 bp, approximately 100 to approximately 5,000 bp, approximately 200 to approximately 100,000 bp, approximately 200 to approximately 50,000 bp, approximately 200 to approximately 10,000 bp, approximately 200 to approximately 5,000 bp, approximately 300 to approximately 100,000 bp, approximately 300 to approximately 50,000 bp, approximately 300 to approximately 10,000 bp, approximately 300 to approximately 5,000 bp, approximately 400 to approximately 100,000 bp, approximately 400 to approximately 40,000 bp, approximately 400 to approximately 10,000 bp, approximately 400 to approximately 5,000 bp, approximately 500 to approximately 100,000 bp, approximately 500 to approximately 50,000 bp, approximately 500 to approximately 10,000 bp, approximately 500 to approximately 5,000 bp, approximately 600 to approximately 100,000 bp, approximately 600 to approximately 50,000 bp, approximately 600 to approximately 10,000 bp, approximately 600 to approximately 5,000 bp, approximately 700 to approximately 100,000 bp, approximately 700 to approximately 50,000 bp, approximately 700 to approximately 10,000 bp, approximately 700 to approximately 5,000 bp, approximately 800 to approximately 100,000 bp, approximately 800 to approximately 50,000 bp, approximately 800 to approximately 10,000 bp, approximately 800 to approximately 5,000 bp, approximately 900 to approximately 100,000 bp, approximately 900 to approximately 50,000 bp, approximately 900 to approximately 10,000 bp, approximately 900 to approximately 5,000 bp, approximately 1,000 to approximately 100,000 bp, approximately 1,000 to approximately 50,000 bp, approximately 1,000 to approximately 10,000 bp, and approximately 1,000 to approximately 5,000 bp.

The nucleic acid fragments include nucleic acids of any size produced by treating and cleaving naturally-occurring or artificially amplified and prepared nucleic acids as described above with one or more of various commercially available restriction enzymes (for example, type I restriction enzymes, type II restriction enzymes, and such).

For example, when detecting or quantifying nucleic acids derived from the genomes of *Staphylococcus aureus* (abbreviated as "SA"), *Staphylococcus epidermidis* (abbreviated as "SE"), *Pseudomonas aeruginosa* (abbreviated as "PA"), *Enterococcus faecalis* (abbreviated as "EF"), *Escherichia coli* (abbreviated as "EC"), *Enterobacter cloacae* (abbreviated as "ET"), and *Klebsiella pneumoniae* (abbreviated as "KP") using the methods and devices of the present invention, all or part of the following genomic regions may be used as targets:

*Staphylococcus aureus*

The nucleic acid sequence of a portion or all of the region from position 2653499 to position 2662118, the region from position 2656232 to position 2657658, or the region from position 2656470 to position 2656799 in the genomic DNA of *Staphylococcus aureus* (abbreviated as "SA") identified by GenBank Accession No. FR714927 (date of last registration: Nov. 21, 2011).

*Staphylococcus epidermidis* ("SE")

The nucleic acid sequence of a portion or all of the region from position 384731 to position 393399, the region from position 385337 to position 388504, or the region from position 385517 to position 385796 in the genomic DNA of

*Staphylococcus epidermis* (abbreviated as "SE") identified by GenBank Accession No. AE015929 (date of last registration: Mar. 5, 2010).

*Pseudomonas aeruginosa* ("PA")

The nucleic acid sequence of a portion or all of the region from position 2386558 to position 2391818, the region from position 2386678 to position 2388735, or the region from position 2387395 to position 2387664 in the genomic DNA of *Pseudomonas aeruginosa* (abbreviated as "PA") identified by GenBank Accession No. CP004061 (date of last registration: Apr. 9, 2013).

*Enterococcus faecalis* ("EF")

The nucleic acid sequence of a portion or all of the region from position 1837695 to position 1841178, the region from position 1838789 to position 1839704, or the region from position 1839147 to position 1839386 in the genomic DNA of *Enterococcus faecalis* (abbreviated as "EF") identified by GenBank Accession No. HF558530 (date of last registration: Dec. 3, 2012).

*Escherichia coli* ("EC")

The nucleic acid sequence of a portion or all of the region from position 1286884 to position 1291840, the region from position 1290625 to position 1291839, or the region from position 1291152 to position 1291460 in the genomic DNA of *Escherichia coli* (abbreviated as "EC") identified by GenBank Accession No. AP012306 (date of last registration: Mar. 29, 2013).

*Enterobacter cloacae* ("ET")

The nucleic acid sequence of a portion or all of the region from position 1566239 to position 1568859 or the region from position 1566732 to position 1566956 in the genomic DNA of *Enterobacter cloacae* (abbreviated as "ET") identified by GenBank Accession No. CP001918 (date of last registration: Apr. 23, 2010).

*Klebsiella pneumoniae* ("KP")

The nucleic acid sequence of a portion or all of the region from position 4082686 to position 4083937, the region from position 4082686 to position 4083380, or the region from position 4082799 to position 4083096 in the genomic DNA of *Klebsiella pneumoniae* (abbreviated as "KP") identified by GenBank Accession No. CP003785 (date of last registration: Mar. 12, 2013).

The aforementioned double-stranded nucleic acids and nucleic acids having higher-order structures can be made into single strands, or a portion of their higher-order structures can be eliminated, by denaturation (cleavage of hydrogen bonds between complementary nucleotide chains) by heat, acid, alkali, chaotropic agents, or denaturants. For example, the nucleic acid can be denatured into single strands, or some of its higher-order structures can be eliminated, by placing it under conditions such as high temperature (approximately 90° C. or higher), high pH (alkaline; pH of approximately 9 or higher), low salt concentration, presence of denaturants or chaotropic ions, pressurization, stirring, and such.

Examples of chaotropic agents include formamide, urea, thiourea, guanidine, guanidine hydrochloride, guanidine isothiocyanate, iodide ions, and perchlorate ions.

"Target nucleic acids" in the present invention mean nucleic acids contained in or derived from samples, which are to be detected or quantified by the detection/quantification methods of the present invention or by the devices or kits for use in those methods. They are preferably nucleic acids that are originally single-stranded, or single-stranded nucleic acids or nucleic acids having a single-stranded region produced as a result of denaturation.

The target nucleic acids also include those labeled with the later-described various labeling substances, and those after being hybridized with one or more oligonucleotide probes and/or one or more mask oligonucleotides ("oligonucleotide M1'", "oligonucleotide M2'", "oligonucleotide M3'", "oligonucleotide M4'", . . . , "oligonucleotide MX'" as in the above-described exemplary embodiments and as described later).

In the present invention, such nucleic acids formed through hybridization of one or more oligonucleotides to target nucleic acids are called "nucleic acid hybrids".

The single-stranded target nucleic acids may become double-stranded again in the detection and quantification process of the present invention due to annealing with complementary nucleic acids after binding with the oligonucleotide probes and/or the mask oligonucleotides, but such embodiments are also included in an embodiment of the present invention.

In the present invention, hybridization of one or more oligonucleotide probes and/or one or more mask oligonucleotides to the single-stranded region of a target nucleic acid, which is included in the nucleic acid chromatography of the present invention which will be described later, can be adjusted by placing at least one of the above-mentioned denaturants or chaotropic agents in a buffer used to develop the later-described nucleic acid or nucleic acid hybrid through the developing element. Additionally, at least one inorganic salt ordinarily used in nucleic acid hybridization can be placed in the buffer.

More specifically, in this hybridization step, the presence of the aforementioned denaturant or chaotropic agent will reduce non-specific binding between the target nucleic acid and the respective oligonucleotides and promote specific reactions, and thereby increasing resolution and decreasing the lower detection limit. This makes it possible to increase the sensitivity, accuracy and rapidity of detection and quantification of the target nucleic acid.

The buffer may be supplemented with, for example, 10% to 40%, preferably 15% to 30%, and more preferably 20% to 25% formamide; 1 M to 7 M, preferably 1 M to 4 M, and more preferably 2.5 M to 4 M urea or thiourea; and 0.5 M to 5 M, preferably 1 M to 4 M, and more preferably 1.2 M to 3 M guanidine or guanidine isothiocyanate, and/or chaotropic agent such as iodide ion or perchlorate ion. The buffer may be further supplemented with inorganic salts generally used in hybridization.

The sample may contain one or two or more different target nucleic acids. As described later, use of the methods and devices or kits of the present invention will enable simultaneous detection or quantification of the two or more different target nucleic acids contained in the sample.

One embodiment of the detection/quantification of a target nucleic acid in the present invention (represented by, for example, Embodiments [1] to [66] of the present invention exemplified above, but not limited thereto) includes, for example, capturing a single-stranded target nucleic acid (hereinafter referred to as "target nucleic acid N"; the letter N is the initial letter of "nucleic acid") by hybridization of an oligonucleotide probe R1' (hereinafter referred to as "oligonucleotide R1'"; which may be labeled with a label L1 described later) to any region (hereinafter referred to as "region R1") in the target nucleic acid N.

Furthermore, in the present invention, the oligonucleotide R1' (which may be labeled with label L1) may be called "capture oligonucleotide".

The region R1 includes, for example, regions close to the 5' or 3' end of the target nucleic acid N. The length of the region R1 may be, for example, approximately 10-mer to approximately 300-mer, approximately 10-mer to approximately 200-mer, approximately 10-mer to approximately 150-mer, approximately 10-mer to approximately 100-mer, approximately 10-mer to approximately 90-mer, approximately 10-mer to approximately 80-mer, approximately 10-mer to approximately 70-mer, approximately 10-mer to approximately 60-mer, approximately 10-mer to approximately 50-mer, approximately 10-mer to approximately 40-mer, approximately 10-mer to approximately 30-mer, approximately 10-mer to approximately 20-mer, approximately 15-mer to approximately 300-mer, approximately 15-mer to approximately 200-mer, approximately 15-mer to approximately 150-mer, approximately 15-mer to approximately 100-mer, approximately 15-mer to approximately 90-mer, approximately 15-mer to approximately 80-mer, approximately 15-mer to approximately 70-mer, approximately 15-mer to approximately 60-mer, approximately 15-mer to approximately 50-mer, approximately 15-mer to approximately 40-mer, approximately 15-mer to approximately 30-mer, approximately 15-mer to approximately 20-mer, approximately 20-mer to approximately 300-mer, approximately 20-mer to approximately 200-mer, approximately 20-mer to approximately 250-mer, approximately 20-mer to approximately 100-mer, approximately 20-mer to approximately 90-mer, approximately 20-mer to approximately 80-mer, approximately 20-mer to approximately 70-mer, approximately 20-mer to approximately 60-mer, approximately 20-mer to approximately 50-mer, approximately 20-mer to approximately 40-mer, approximately 20-mer to approximately 30-mer, approximately 25-mer to approximately 300-mer, approximately 25-mer to approximately 200-mer, approximately 25-mer to approximately 150-mer, approximately 25-mer to approximately 100-mer, approximately 25-mer to approximately 90-mer, approximately 25-mer to approximately 80-mer, approximately 25-mer to approximately 70-mer, approximately 25-mer to approximately 60-mer, approximately 25-mer to approximately 50-mer, approximately 25-mer to approximately 40-mer, or approximately 25-mer to approximately 30-mer.

The oligonucleotide probe R1' (oligonucleotide R1') which hybridizes to the region R1 is an oligonucleotide containing a nucleotide sequence complementary to the nucleotide sequence of the region R1. The length of the oligonucleotide probe R1' corresponds to the length of the region R1, and may be, for example, approximately 10-mer to approximately 300-mer, approximately 10-mer to approximately 200-mer, approximately 10-mer to approximately 150-mer, approximately 10-mer to approximately 100-mer, approximately 10-mer to approximately 90-mer, approximately 10-mer to approximately 80-mer, approximately 10-mer to approximately 70-mer, approximately 10-mer to approximately 60-mer, approximately 10-mer to approximately 50-mer, approximately 10-mer to approximately 40-mer, approximately 10-mer to approximately 30-mer, approximately 10-mer to approximately 20-mer, approximately 15-mer to approximately 300-mer, approximately 15-mer to approximately 200-mer, approximately 15-mer to approximately 150-mer, approximately 15-mer to approximately 100-mer, approximately 15-mer to approximately 90-mer, approximately 15-mer to approximately 80-mer, approximately 15-mer to approximately 70-mer, approximately 15-mer to approximately 60-mer, approximately 15-mer to approximately 50-mer, approximately 15-mer to approximately 40-mer, approximately 15-mer to approximately 30-mer, approximately 15-mer to approximately 20-mer, approximately 20-mer to approximately 300-mer, approximately 20-mer to approximately 200-mer, approximately 20-mer to approximately 250-mer, approximately 20-mer to approximately 100-mer, approximately 20-mer to approximately 90-mer, approximately 20-mer to approximately 80-mer, approximately 20-mer to approximately 70-mer, approximately 20-mer to approximately 60-mer, approximately 20-mer to approximately 50-mer, approximately 20-mer to approximately 40-mer, approximately 20-mer to approximately 30-mer, approximately 25-mer to approximately 300-mer, approximately 25-mer to approximately 200-mer, approximately 25-mer to approximately 150-mer, approximately 25-mer to approximately 100-mer, approximately 25-mer to approximately 90-mer, approximately 25-mer to approximately 80-mer, approximately 25-mer to approximately 70-mer, approximately 25-mer to approximately 60-mer, approximately 25-mer to approximately 50-mer, approximately 25-mer to approximately 40-mer, or approximately 25-mer to approximately 30-mer.

Furthermore, the oligonucleotide probe R1' (oligonucleotide R1') may also have one or more mismatches or bulges with respect to the nucleotide sequence of the region R1, if desired, as long as it hybridizes to the region R1.

In the present invention, the oligonucleotide probe R1' (oligonucleotide R1') which hybridizes to the region R1 may be labeled with a labeling substance (hereinafter referred to as "label L1"; the letter L comes from the term "label").

Examples of the label L1 include colloidal metal particles (such as colloidal gold particles, colloidal platinum particles, colloidal platinum-gold (Pt—Au) particles, colloidal palladium particles, colloidal silver particles, colloidal copper particles, colloidal nickel particles, colloidal rhodium particles, colloidal ruthenium particles, or colloidal iridium particles), latex particles (such as white latex particles, colored latex particles, fluorescent latex particles, magnetic latex particles, or functional group-modified latex particles), colored liposomes, nonmetallic colloids (such as selenium colloids), various enzymes (such as alkaline phosphatase, peroxidase, glucose oxidase, or β-galactosidase), colored resin particles, colloidal dyes, insoluble granular substances, fluorescent dyes, and radioisotopes.

The detection/quantification of target nucleic acids of the present invention further includes hybridization of an oligonucleotide probe R2' (hereinafter referred to as "oligonucleotide R2'"; which may have the later-described anchor A at its terminus) to any region (hereinafter referred to as "region R2") that is different from the region R1 in the target nucleic acid N.

As described later, the target nucleic acid N bound to the oligonucleotide R1' labeled with the label L1 can be captured by chromatography via this oligonucleotide R2' (for example, the aforementioned Embodiments [1] to [23] of the present invention; embodiments (1) to (3) in FIG. 2; and embodiments (a) to (1) in Table 1).

In the present invention, the oligonucleotide R2' (which may have an anchor A) may be referred to as "detection oligonucleotide".

Examples of the region R2 in the labeled nucleic acid N to which the aforementioned oligonucleotide R2' hybridizes include regions close to the 5' or 3' end of the target nucleic acid N. The length of the region R2 may be, for example, approximately 10-mer to approximately 300-mer, approximately 10-mer to approximately 200-mer, approximately 10-mer to approximately 150-mer, approximately 10-mer to approximately 100-mer, approximately 10-mer to approximately 90-mer, approximately 10-mer to approximately 80-mer, approximately 10-mer to approximately 70-mer, approximately 10-mer to approximately 60-mer, approximately 10-mer to approximately 50-mer, approximately 10-mer to approximately 40-mer, approximately 10-mer to approximately 30-mer, approximately 10-mer to approximately 20-mer, approximately 15-mer to approximately 300-mer, approximately 15-mer to approximately 200-mer, approximately 15-mer to approximately 150-mer, approximately 15-mer to approximately 100-mer, approximately 15-mer to approximately 90-mer, approximately 15-mer to approximately 80-mer, approximately 15-mer to approximately 70-mer, approximately 15-mer to approximately 60-mer, approximately 15-mer to approximately 50-mer, approximately 15-mer to approximately 40-mer, approximately 15-mer to approximately 30-mer, approximately 15-mer to approximately 20-mer, approximately 20-mer to approximately 300-mer, approximately 20-mer to approximately 200-mer, approximately 20-mer to approximately 250-mer, approximately 20-mer to approximately 100-mer, approximately 20-mer to approximately 90-mer, approximately 20-mer to approximately 80-mer, approximately 20-mer to approximately 70-mer, approximately 20-mer to approximately 60-mer, approximately 20-mer to approximately 50-mer, approximately 20-mer to approximately 40-mer, approximately 20-mer to approximately 30-mer, approximately 25-mer to approximately 300-mer, approximately 25-mer to approximately 200-mer, approximately 25-mer to approximately 150-mer, approximately 25-mer to approximately 100-mer, approximately 25-mer to approximately 90-mer, approximately 25-mer to approximately 80-mer, approximately 25-mer to approximately 70-mer, approximately 25-mer to approximately 60-mer, approximately 25-mer to approximately 50-mer, approximately 25-mer to approximately 40-mer, or approximately 25-mer to approximately 30-mer.

The oligonucleotide probe R2' (oligonucleotide R2') which hybridizes to the region R2 is an oligonucleotide containing a nucleotide sequence complementary to the nucleotide sequence of the region R2. The length of the oligonucleotide probe R2' corresponds to the length of the region R2, and may be, for example, approximately 10-mer to approximately 300-mer, approximately 10-mer to approximately 200-mer, approximately 10-mer to approximately 150-mer, approximately 10-mer to approximately 100-mer, approximately 10-mer to approximately 90-mer, approximately 10-mer to approximately 80-mer, approximately 10-mer to approximately 70-mer, approximately 10-mer to approximately 60-mer, approximately 10-mer to approximately 50-mer, approximately 10-mer to approximately 40-mer, approximately 10-mer to approximately 30-mer, approximately 10-mer to approximately 20-mer, approximately 15-mer to approximately 300-mer, approximately 15-mer to approximately 200-mer, approximately 15-mer to approximately 150-mer, approximately 15-mer to approximately 100-mer, approximately 15-mer to approximately 90-mer, approximately 15-mer to approximately 80-mer, approximately 15-mer to approximately 70-mer, approximately 15-mer to approximately 60-mer, approximately 15-mer to approximately 50-mer, approximately 15-mer to approximately 40-mer, approximately 15-mer to approximately 30-mer, approximately 15-mer to approximately 20-mer, approximately 20-mer to approximately 300-mer, approximately 20-mer to approximately 200-mer, approximately 20-mer to approximately 250-mer, approximately 20-mer to approximately 100-mer, approximately 20-mer to approximately 90-mer, approximately 20-mer to approximately 80-mer, approximately 20-mer to approximately 70-mer, approximately 20-mer to approximately 60-mer, approximately 20-mer to approximately 50-mer, approximately 20-mer to approximately 40-mer, approximately 20-mer to approximately 30-mer, approximately 25-mer to approximately 300-mer, approximately 25-mer to approximately 200-mer, approximately 25-mer to approximately 150-mer, approximately 25-mer to approximately 100-mer, approximately 25-mer to approximately 90-mer, approximately 25-mer to approximately 80-mer, approximately 25-mer to approximately 70-mer, approximately 25-mer to approximately 60-mer, approximately 25-mer to approximately 50-mer, approximately 25-mer to approximately 40-mer, or approximately 25-mer to approximately 30-mer.

Furthermore, the oligonucleotide probe R2' (oligonucleotide R2') may also have one or more mismatches or bulges with respect to the nucleotide sequence of the region R2, if desired, as long as it hybridizes to the region R2.

In one embodiment of the detection/quantification of a target nucleic acid in the present invention (represented by, for example, Embodiments [12] to [19], [23], [48] to [52], and such of the present invention exemplified above, but not limited thereto), the aforementioned oligonucleotide R2' may have, for example, an arbitrary anchor (hereinafter referred to as "anchor A") at its terminus. On the other hand, an "acceptor A'" which is different from the anchor A and may bind to the anchor A, can be immobilized in the "detection zone" of a "development element" to be used for the later-described nucleic acid chromatography, so that a nucleic acid hybrid containing the target nucleic acid N (a nucleic acid hybrid formed by hybridization of one or more mask oligonucleotides, the L1-labeled oligonucleotide probe R1' and/or the oligonucleotide probe R2' having the anchor A, to the target nucleic acid N) can be captured via binding between the anchor A and the acceptor A', and the target nucleic acid can be detected or quantified.

The anchor A may be, for example, an oligonucleotide, biotin, antibody, protein, or carbohydrate chain, and the acceptor A' may be, for example, an oligonucleotide, avidin, streptavidin, antibody, or protein.

In a preferred embodiment, the anchor A is biotin and the acceptor A' is avidin or streptavidin.

Furthermore, when a number of different target nucleic acids N are included in a sample, they can be simultaneously detected or quantified by chromatography with different anchors A bound to the respective oligonucleotide probes R2' which correspond to the respective target nucleic acids (for example, FIGS. 4-9, 4-11, 4-12, and such).

Meanwhile, in one embodiment of the detection/quantification of a target nucleic acid in the present invention (represented by, for example, Embodiments [29] to [52] of the present invention; embodiments (4) to (7) in FIG. 2; and embodiments (m) to (v) in Table 1 exemplified above, but not limited thereto), the target nucleic acid N is labeled with a labeling substance (hereinafter referred to as "label L2"; the letter L comes from the term "label") (hereinafter referred to as "L2-labeled target nucleic acid N" in some cases).

Furthermore, the present invention includes capturing of the L2-labeled target nucleic acid N through hybridization of one or more of the later-described mask oligonucleotides to the L2-labeled target nucleic acid N, and hybridization of the oligonucleotide probe R2' (same as the aforementioned "oligonucleotide R2'") to any region (same as the aforementioned "region R2") in the target nucleic acid N or hybridization of the L1-labeled oligonucleotide probe R1' (same as the aforementioned "L1-labeled oligonucleotide R1") to any region (same as the aforementioned "region R1") in the target nucleic acid N.

One embodiment of the detection/quantification of a target nucleic acid in the present invention (represented by, for example, Embodiments [35] to [39] of the present invention; embodiment (4) in FIG. 2; and embodiments (m) to (p) in Table 1 exemplified above, but not limited thereto) includes capturing the target nucleic acid N by hybridization of the L1-labeled oligonucleotide probe R1' ("L1-labeled oligonucleotide R1'") to any region R1 in the target nucleic acid N, similarly to the above-described Embodiments [1] to [23] of the present invention.

Further, in these embodiments, a substance that may bind to the label L2 is immobilized on the "detection zone" of the "development element" to be used for the later-described nucleic acid chromatography, so that a nucleic acid hybrid containing the target nucleic acid N (a nucleic acid hybrid formed by hybridization of one or more mask oligonucleotides and the L1-labeled oligonucleotide probe R1' to the target nucleic acid N) can be captured via binding between the label L2 and the immobilized substance, and thereby the target nucleic acid can be detected or quantified.

Examples of the label L2 include fluorescent dyes (fluorescein isothiocyanate (FITC), 6-carboxyfluorescein (6-FAM), TET, VIC, HEX, NED, PET, ROX, Cy5, Cy3, Texas Red, JOE, TAMRA, etc.), biotin, digoxigenin (DIG), antibodies, and enzymes (for example, the enzyme may be peroxidase, glucose oxidase, alkaline phosphatase, β-galactosidase, or such). The antibody may be labeled with the above-mentioned fluorescent dyes, biotin, digoxigenin (DIG), or such.

When the target nucleic acid is derived from a nucleic acid amplified by PCR and such, for example, the target nucleic acid N can be labeled with the label L2 through the PCR process according to conventional methods.

Examples of the substance that binds to the label L2 include antibodies or enzyme-labeled antibodies that bind to the label L2. When the label L2 is biotin, examples of the substance include avidin or streptavidin.

Furthermore, the enzyme is, for example, alkaline phosphatase, peroxidase, glucose oxidase, or β-galactosidase.

In one embodiment of the detection/quantification of a target nucleic acid in the present invention (represented by, for example, Embodiments [46] and [47] of the present invention; embodiments (5) and (6) in FIG. 2; embodiments (q) and (r) in Table 1 exemplified above, but not limited thereto), the oligonucleotide R2' which may hybridize to the arbitrary region R2 in the target nucleic acid N is immobilized on the "detection zone" of the "development element" to be used for the later-described nucleic acid chromatography, so that the target nucleic acid N can be captured via hybridization between the region R2 and the oligonucleotide R2', and the target nucleic acid can be detected using the label L2 as an indicator.

Detection/quantification of the target nucleic acid N using the label L2 as an indicator can be carried out, for example, through binding of the L2-binding antibody or enzyme-labeled antibody to the label L2.

One embodiment of the detection/quantification of a target nucleic acid in the present invention (represented by, for example, Embodiments [48] to [51] and such of the present invention exemplified above, but not limited thereto) includes hybridization of an oligonucleotide probe R2' ("oligonucleotide R2'") having an arbitrary anchor (hereinafter referred to as "anchor A") at its terminus to the target nucleic acid N. On the other hand, an "acceptor A'" which is different from the anchor A and may bind to the anchor A is immobilized on the "detection zone" of the "development element" to be used for the later-described nucleic acid chromatography, so that a nucleic acid hybrid containing the L2-labeled target nucleic acid N (a nucleic acid hybrid formed by hybridization of one or more mask oligonucleotides and the oligonucleotide probe R2' having the anchor A to the L2-labeled target nucleic acid N) is captured via binding between the anchor A and the acceptor A', and the target nucleic acid can be detected or quantified.

The anchor A is, for example, an oligonucleotide, biotin, small compound such as digoxigenin (DIG), antibody, protein, or carbohydrate chain The acceptor A' is, for example, an oligonucleotide, avidin, streptavidin, antibody, or protein.

In a preferred embodiment, the anchor A is biotin, and the acceptor A' is avidin or streptavidin.

All embodiments of the detection/quantification of a target nucleic acid in the present invention include hybridization of at least one of mask oligonucleotides M1', M2', M3', and M4' to at least one of "region M1" and "region M2" (the letter M is the first letter of the term "mask oligonucleotide", which will be described later) which are positioned so that the region R1 is between them (which are adjacent or close to both ends of the region R1) in the target nucleic acid N (or L2-labeled target nucleic acid N), and "region M3" and "region M4" which are positioned so that the region R2 is between them in the target nucleic acid N (which are adjacent or close to both ends of the region R2).

More specifically, hybridization of the mask oligonucleotides to the target nucleic acid N includes the following embodiments:

mask oligonucleotide M1' is hybridized only to region M1;
mask oligonucleotide M2' is hybridized only to region M2;
mask oligonucleotide M3' is hybridized only to region M3;
mask oligonucleotide M4' is hybridized only to region M4;
mask oligonucleotides M1' and M2' are hybridized to both regions M1 and M2, respectively;
mask oligonucleotides M3' and M4' are hybridized to both regions M3 and M4, respectively;
mask oligonucleotides M1' and M3' are hybridized to both regions M1 and M3, respectively;
mask oligonucleotides M1' and M4' are hybridized to both regions M1 and M4, respectively;
mask oligonucleotides M2' and M3' are hybridized to both regions M2 and M3, respectively;
mask oligonucleotides M2' and M4' are hybridized to both regions M2 and M4, respectively;
mask oligonucleotides M1', M2', and M3' are hybridized to regions M1, M2, and M3, respectively;
mask oligonucleotides M1', M2', and M4' are hybridized to regions M1, M2, and M4, respectively;
mask oligonucleotides M1', M3', and M4' are hybridized to regions M1, M3, and M4, respectively;
mask oligonucleotides M2', M3', and M4' are hybridized to regions M2, M3, and M4, respectively;
mask oligonucleotides M1', M2', M3', and M4' are hybridized to regions M1, M2, M3, and M4, respectively;

When necessary, the present invention further includes embodiments in which mask oligonucleotides which contain nucleic acid sequences complementary to one or more other regions besides regions M1, M2, M3, and M4 in the target nucleic acid N (regions M5, M6, M7, M8, etc.) and may hybridize to those regions, respectively, are hybridized to the corresponding regions.

In preferred embodiments of the present invention, mask oligonucleotides M1' and M2' are hybridized to both regions M1 and M2, respectively, or mask oligonucleotides M3' and M4' are hybridized to both regions M3 and M4, respectively.

The "region M1" and "region M2" which are positioned so that the region R1 is between them (which are adjacent or close to both ends of the region R1) in the target nucleic acid N means that, for example, the respective regions are present in the target nucleic acid N in the order of region M1-region R1-region M2 (or region M2-region R1-region M1) in the 5'-end to 3'-end direction.

It also means that region M1 and region R1 are adjacent to each other with no nucleotide gap in between, or region M1 and region R1 are separated from each other by 1-mer to 30-mer, 1-mer to 29-mer, 1-mer to 28-mer, 1-mer to 27-mer, 1-mer to 26-mer, 1-mer to 25-mer, 1-mer to 24-mer, 1-mer to 23-mer, 1-mer to 22-mer, 1-mer to 21-mer, 1-mer to 20-mer, 1-mer to 19-mer, 1-mer to 18-mer, 1-mer to 17-mer, 1-mer to 16-mer, 1-mer to 15-mer, 1-mer to 14-mer, 1-mer to 13-mer, 1-mer to 12-mer, 1-mer to 11-mer, 1-mer to 10-mer, 1-mer to 9-mer, 1-mer to 8-mer, 1-mer to 7-mer, 1-mer to 6-mer, 1-mer to 5-mer, 1-mer to 4-mer, 1-mer to 3-mer, 2-mer, or 1-mer.

In preferred embodiments, regions M1 and R1 are adjacent to each other with no single nucleotide gap in between, or are separated from each other by 1-mer to 20-mer.

Preferably, regions M1 and R1 are adjacent to each other with no nucleotide gap in between, or are separated from each other by 1-mer to 15-mer.

More preferably, regions M1 and R1 are adjacent to each other with no nucleotide gap in between, or are separated from each other by 1-mer to 10-mer.

Even more preferably, regions M1 and R1 are adjacent to each other with no nucleotide gap in between, or are separated from each other by 1-mer to 5-mer.

The positional relationship between regions M2 and R1, between regions M3 and R2, and between regions R4 and R2 are the same as the above-described positional relationship between regions M1 and R1.

As described above, the mask oligonucleotides of the present invention are oligonucleotides comprising nucleotide sequences complementary to the respective nucleic acid sequences of regions M1, M2, M3, and M4 (if desired, additional regions M5, M6, M7, M8, and such are also included) in a target nucleic acid N or L2-labeled target nucleic acid N.

The lengths of the mask oligonucleotides correspond to the lengths of regions M1, M2, M3, and M4, respectively, and may be, for example, approximately 5-mer to approximately 300-mer, approximately 5-mer to approximately 200-mer, approximately 5-mer to approximately 150-mer, approximately 5-mer to approximately 100-mer, approximately 5-mer to approximately 90-mer, approximately 5-mer to approximately 80-mer, approximately 5-mer to approximately 70-mer, approximately 5-mer to approximately 60-mer, approximately 5-mer to approximately 50-mer, approximately 5-mer to approximately 40-mer, approximately 5-mer to approximately 30-mer, approximately 5-mer to approximately 20-mer approximately 10-mer to approximately 300-mer, approximately 10-mer to approximately 200-mer, approximately 10-mer to approximately 150-mer, approximately 10-mer to approximately 100-mer, approximately 10-mer to approximately 90-mer, approximately 10-mer to approximately 80-mer, approximately 10-mer to approximately 70-mer, approximately 10-mer to approximately 60-mer, approximately 10-mer to approximately 50-mer, approximately 10-mer to approximately 40-mer, approximately 10-mer to approximately 30-mer, approximately 10-mer to approximately 20-mer, approximately 15-mer to approximately 300-mer, approximately 15-mer to approximately 200-mer, approximately 15-mer to approximately 150-mer, approximately 15-mer to approximately 100-mer, approximately 15-mer to approximately 90-mer, approximately 15-mer to approximately 80-mer, approximately 15-mer to approximately 70-mer, approximately 15-mer to approximately 60-mer, approximately 15-mer to approximately 50-mer, approximately 15-mer to approximately 40-mer, approximately 15-mer to approximately 30-mer, approximately 15-mer to approximately 20-mer, approximately 20-mer to approximately 300-mer, approximately 20-mer to approximately 200-mer, approximately 20-mer to approximately 250-mer, approximately 20-mer to approximately 100-mer, approximately 20-mer to approximately 90-mer, approximately 20-mer to approximately 80-mer, approximately 20-mer to approximately 70-mer, approximately 20-mer to approximately 60-mer, approximately 20-mer to approximately 50-mer, approximately 20-mer to approximately 40-mer, approximately 20-mer to approximately 30-mer, approximately 25-mer to approximately 300-mer, approximately 25-mer to approximately 200-mer, approximately 25-mer to approximately 150-mer, approximately 25-mer to approximately 100-mer, approximately 25-mer to approximately 90-mer, approximately 25-mer to approximately 80-mer, approximately 25-mer to approximately 70-mer, approximately 25-mer to approximately 60-mer, approximately 25-mer to approximately 50-mer, approximately 25-mer to approximately 40-mer, or approximately 25-mer to approximately 30-mer.

Each mask oligonucleotide (M1', M2', M3', or M4') may have one or more mismatches or bulges with respect to the nucleotide sequence of each region (M1, M2, M3, or M4) if desired, as long as they hybridize to each region (M1, M, M3, or M4).

The detection/quantification of a nucleic acid in the present invention may also be applied when two or more target nucleic acids are contained in a sample (for example, multiple target nucleic acids derived from different bacteria, multiple target nucleic acids derived from a plurality of mutants of a specific bacterium, multiple target nucleic acids derived from a plurality of mutants of a specific gene, or multiple target nucleic acids derived from multiple PCR products amplified by multiplex PCR). That is, by using the present invention, such multiple target nucleic acids can be simultaneously detected or quantified in a single assay.

In the present invention, in order to detect or quantify one target nucleic acid or simultaneously detect or quantify two or more different target nucleic acids which is/are included or predicted to be included in a sample, one or more of the above-mentioned mask oligonucleotides (M1', M2', M3', and M4'), oligonucleotide probe R1' (oligonucleotide R1'), and when necessary, oligonucleotide probe R2' (oligonucleotide R2'), are designed and prepared for the target nucleic acid or each of the two or more different target nucleic acids; and for example, the later-described lateral-flow or flow-through chromatography (nucleic acid chromatography), or hybridization-ELISA is applied using these oligonucleotides.

Specifically, for example, when there are three target nucleic acids to be detected or quantified (target nucleic acids $N_1$, $N_2$, and $N_3$), one or more mask oligonucleotides (M1', M2', M3', and M4'), oligonucleotide probe R1' (oligonucleotide R1'), and when necessary, oligonucleotide probe R2' (oligonucleotide R2') that are capable of hybridizing to the target nucleic acid $N_1$ and necessary for detecting the target nucleic acid $N_1$, are designed and prepared. In addition, one or more mask oligonucleotides (M1', M2', M3', and M4'), oligonucleotide probe R1' (oligonucleotide R1'), and when necessary, oligonucleotide probe R2' (oligonucleotide R2') that are capable of hybridizing to the target nucleic acid $N_2$ and necessary for detecting the target nucleic acid $N_2$, are designed and prepared. Moreover, one or more mask oligonucleotides (M1', M2', M3', and M4'), oligonucleotide probe R1' (oligonucleotide R1'), and when necessary, oligonucleotide probe R2' (oligonucleotide R2') that are capable of hybridizing to target nucleic acid $N_3$ and are necessary for detecting the target nucleic acid $N_3$, are designed and prepared.

In the present invention, the detection/quantification of a nucleic acid can be performed using, for example, nucleic acid chromatography (lateral flow or flow through), which employs the principle of immunochromatography, or using hybridization-ELISA, which utilizes immunoassay, but it is not limited thereto.

The nucleic acid chromatography can be exemplified by, for example, embodiments that use the devices and principles shown schematically in FIG. 2 (embodiments (1) to (7)), FIGS. 4-1 to 4-7, and FIGS. 4-9 to 4-12, but obviously they are not limited to these embodiments.

In addition, the nucleic acid chromatography of the present invention can be exemplified by embodiments in which the above-mentioned target nucleic acid (which may be labeled with a label L2), oligonucleotide R1' (which may be labeled with a label L1), oligonucleotide R2' (which may have an anchor A), mask oligonucleotides, acceptor A', and/or substance that binds to the label L2, are applied, enclosed, and immobilized to the "application zone", "enclosing zone", and "detection zone" of the later-described device of this invention according to the combinations exemplified in Table 1 above; but obviously it is not limited to these embodiments.

If desired, the nucleic acid chromatography of the present invention can be carried out by embodiments in which a portion of a "development element" (described later) having one or more "detection zones" only is applied to (contacted with) a liquid sample containing target nucleic acids and the aforementioned respective oligonucleotides, which is placed in a solid support having a volume capacity (for example, tubes, vials, plates, or beakers), or embodiments in which the liquid sample is applied to a portion of the solid support.

The hybridization-ELISA can be exemplified by, for example, the embodiments shown schematically in FIG. 2 (embodiments (5) and (6)), and FIG. 4-8, but obviously it is not limited to these embodiments.

These methods will be outlined below; however, it goes without saying that each of the items outlined below may be subjected to desired alterations, changes, additions and such when necessary in carrying out various embodiments included in the present invention.

In the present invention, including all embodiments illustrated below, the hybridization between the above-mentioned target nucleic acid (which may be labeled with a label L2), oligonucleotide R1' (which may be labeled with a label L1), oligonucleotide R2' (which may have an anchor A), mask oligonucleotides, and various nucleic acid hybrids, and the binding between the anchor A and the acceptor A', and the binding between the label L2 and a substance that binds to label L2, encompass all of those that take place throughout the entire period from the beginning to the end of the assay, and does not only mean hybridization or binding taking place only at a certain site, portion, or point of time.

Furthermore, in the present invention, the hybridization between the above-mentioned target nucleic acid (which may be labeled with a label L2), oligonucleotide R1' (which may be labeled with a label L1), oligonucleotide R2' (which may have an anchor A), mask oligonucleotides, and various nucleic acid hybrids, encompasses any embodiments such as those in which one certain hybridization and one or two or more hybridizations that are different from that hybridization are individually completed gradually over time, in which each of them takes place separately, and in which each of them takes place simultaneously.

1. Lateral-Flow Nucleic Acid Chromatography

Examples include the embodiments schematically shown in FIGS. 4-1 to 4-7 and FIGS. 4-9 to 4-12. Only for the purpose of brief understanding of the basic principles employed in these embodiments, these principles are roughly outlined below.

However, in the present invention, including the explanation of the principles outlined below, the hybridization between the target nucleic acid (which may be labeled with a label L2), oligonucleotide R1' (which may be labeled with a label L1), oligonucleotide R2' (which may have an anchor A), mask oligonucleotides, and nucleic acid hybrids, the binding between the anchor A and the acceptor A', and the binding between the label L2 and a substance that binds to the label L2, encompass all of those taking place throughout the entire period from the beginning to the end of the assay, and do not refer only to hybridization or binding taking place only at a certain site, portion, or point of time.

Furthermore, in the present invention, the hybridization between the target nucleic acid (which may be labeled with a label L2), oligonucleotide R1' (which may be labeled with a label L1), oligonucleotide R2' (which may have an anchor A), mask oligonucleotides, and nucleic acid hybrids encompasses any embodiments such as those in which one certain hybridization and one or two or more hybridizations that are different from that hybridization are individually completed gradually over time, in which each of them takes place separately, and in which each of them takes place simultaneously. The same applies to binding between the anchor A and the acceptor A'.

In the lateral-flow nucleic acid chromatography that uses the principles and devices (or kits) schematically shown in FIGS. 4-1 and 4-2, a nucleic acid hybrid (nucleic acid hybrid produced by hybridization of a target nucleic acid N, one or more mask oligonucleotides, and an L1-labeled oligonucleotide R1') that has reached the detection zone by moving through the development element by capillary action and dispersion is captured by an oligonucleotide R2' immobilized on the detection zone, and the presence and amount of the target nucleic acid N contained in the liquid sample can be determined through detection using the label L1 as an indicator.

In the lateral-flow nucleic acid chromatography that uses the principles and devices (or kits) schematically shown in FIGS. 4-3 and 4-4, a nucleic acid hybrid (nucleic acid hybrid produced by hybridization of a target nucleic acid N, one or more mask oligonucleotides, an L1-labeled oligonucleotide R1', and an oligonucleotide R2' having an anchor A at its terminus) that has reached the detection zone by moving through the development element by capillary action and dispersion is captured by an acceptor A' that binds to the anchor A and has been immobilized on the detection zone, and the presence and amount of the target nucleic acid N contained in the liquid sample can be determined through detection using the label L1 as an indicator.

In the lateral-flow nucleic acid chromatography that uses the principles and devices (or kits) schematically shown in FIGS. 4-5 and 4-6, a nucleic acid hybrid (nucleic acid hybrid produced by hybridization of a target nucleic acid N labeled with a label L2, one or more mask oligonucleotides, and an L1-labeled oligonucleotide R1') that has reached the detection zone by moving through the development element by capillary action and dispersion is captured by an L2-binding substance immobilized on the detection zone, and the presence and amount of the target nucleic acid N contained in the liquid sample can be determined through detection using the label L1 as an indicator.

In the lateral-flow nucleic acid chromatography that uses the principle and device (or kit) schematically shown in FIG. 4-7, a nucleic acid hybrid (nucleic acid hybrid produced by hybridization of an L2-labeled target nucleic acid N, one or more mask oligonucleotides, and an oligonucleotide R2' having an anchor A at its terminus) that has reached the detection zone by moving through the development element by capillary action and dispersion is captured by an acceptor A' that binds to the anchor A and has been immobilized on the detection-zone, and the presence and amount of the target nucleic acid N contained in the liquid sample can be determined through detection using the label L2 as an indicator.

The lateral-flow nucleic acid chromatography that uses the principle and device (or kit) schematically shown in FIG. 4-9 is an example of the embodiments for simultaneously detecting/quantifying a plurality of target nucleic acids N (for example, target nucleic acids N1 and N2). In this embodiment, a nucleic acid hybrid 1 (nucleic acid hybrid 1 produced by hybridization of a target nucleic acid N1, one or more mask oligonucleotides prepared for the target nucleic acid N1, an L1-labeled oligonucleotide R1' prepared for the target nucleic acid N1, and an oligonucleotide R2' prepared for the target nucleic acid N1 and having an anchor A1 at its terminus) and a nucleic acid hybrid 2 (nucleic acid hybrid 2 produced by hybridization of a target nucleic acid N2, one or more mask oligonucleotides prepared for the target nucleic acid N2, an L1-labeled oligonucleotide R1' prepared for the target nucleic acid N2, and an oligonucleotide R2' prepared for the target nucleic acid N2 and having an anchor A2 at its terminus) that have reached the detection zone by moving through the development element by capillary action and dispersion are individually captured by an acceptor A1' that binds to the anchor A1 and an acceptor A2' that binds to the anchor A2, respectively, which are individually immobilized on the detection zone, and the presence and amount of the target nucleic acids N1 and N2 contained in the liquid sample can be determined simultaneously through detection using the label L1 as an indicator.

The lateral-flow nucleic acid chromatography that uses the principle and device (or kit) schematically shown in FIG. 4-10 is an example of the embodiments for simultaneously detecting/quantifying a plurality of target nucleic acids N (for example, target nucleic acids N1 and N2). In this embodiment, a nucleic acid hybrid 1 (nucleic acid hybrid 1 produced by hybridization of a target nucleic acid N1 labeled with a label L2a (for example, FITC), one or more mask oligonucleotides prepared for the target nucleic acid N1, and an L1-labeled oligonucleotide R1' prepared for the target nucleic acid N1) and a nucleic acid hybrid 2 (nucleic acid hybrid 2 produced by hybridization of a target nucleic acid N2 labeled with a label L2b (for example, Texas Red), one or more mask oligonucleotides prepared for the target nucleic acid N2, and an L1-labeled oligonucleotide R1' prepared for the target nucleic acid N2) that have reached the detection zone by moving through the development element by capillary action and dispersion are individually captured by substance 1 (for example, an anti-FITC antibody) that binds to the label L2a and substance 2 (for example, an anti-Texas Red antibody) that binds to the label L2b, respectively, and the presence and amount of the target nucleic acids N1 and N2 contained in the liquid sample can be determined simultaneously through detection using the label L1 as an indicator.

The lateral-flow nucleic acid chromatography that uses the principle and device (or kit) schematically shown in FIG. 4-11 is an example of the embodiments for simultaneously detecting/quantifying a plurality of target nucleic acids N (for example, target nucleic acids N1 and N2). In this embodiment, a nucleic acid hybrid 1 (nucleic acid hybrid 1 produced by hybridization of a target nucleic acid N1 labeled with a label L2, one or more mask oligonucleotides prepared for the target nucleic acid N1, and an oligonucleotide R2' prepared for the target nucleic acid N1 and having an anchor A1 at its terminus) and a nucleic acid hybrid 2 (nucleic acid hybrid 2 produced by hybridization of a target nucleic acid N2 labeled with a label L2, one or more mask oligonucleotides prepared for the target nucleic acid N2, and an oligonucleotide R2' produced for the target nucleic acid N2 and having an anchor A2 at its terminus) that have reached the detection zone by moving through the development element by capillary action and dispersion are individually captured by an acceptor A1' that binds to the anchor A1 and an acceptor A2' that binds to the anchor A2, respectively, which are individually immobilized on the detection zone, and the presence and amount of the target nucleic acids N1 and N2 contained in the liquid sample can be determined simultaneously through detection using the label L2 as an indicator.

The lateral-flow nucleic acid chromatography that uses the principle and device (or kit) schematically shown in FIG. 4-12 is an example of the embodiments for simultaneously detecting/quantifying a plurality of target nucleic acids N (for example, target nucleic acids N1 and N2). In this embodiment, a nucleic acid hybrid 1 (nucleic acid hybrid 1 produced by hybridization of a target nucleic acid N1 labeled with a label L2a (for example, FITC), one or more mask oligonucleotides prepared for the target nucleic acid N1, and an oligonucleotide R2' prepared for the target nucleic acid N1 and having an anchor A at its terminus) and a nucleic acid hybrid 2 (nucleic acid hybrid 2 produced by hybridization of a target nucleic acid N2 labeled with a label L2b (for example, Texas Red), one or more mask oligonucleotides prepared for the target nucleic acid N2, and an oligonucleotide R2' prepared for the target nucleic acid N2 having an anchor A at its terminus) that have reached the detection zone by moving through the development element by capillary action and dispersion are individually captured by an acceptor A' that binds to the anchor A, and the presence and amount of the target nucleic acids N1 and N2 contained in the liquid sample can be determined simultaneously through detection using the different labels L2a and L2b as indicators, respectively.

In a preferred embodiment, the "development element" in the present invention is a support (membrane) in the form of a sheet or strip, and has the function of chromatographically developing a liquid sample containing various nucleic acids (for example, target nucleic acid (which may be labeled), oligonucleotide R1' (which may be labeled), oligonucleotide R1', oligonucleotide R2' (which may have an anchor A), mask oligonucleotides, and various nucleic acid hybrids formed through hybridization of one or more of them with one another) by capillary action.

As the development element, for example, a porous insoluble support (membrane) may be used, and examples include plastic porous support (membrane), cellulose porous support (membrane), and inorganic porous support (membrane). More specific examples include support (membrane) prepared from porous cellulose, nitrocellulose, cellulose acetate, nylon, silica, glass fiber, or derivatives thereof. Furthermore, in the present invention, as long as the development element has a function similar to that described above, any commercially available porous insoluble supports (membranes) may be used as the development element.

The "application zone" in the present invention is a support in the form of a sheet or strip, which is made of a material identical to or different from that of the aforementioned development element, and is placed in contact with the development element. Examples of the material include those for the aforementioned development element, but depending on the purpose, materials different from that of the development element may be selected.

This application zone may also be referred to as "sample pad" because of its functions, and for example, it may have the following functions without limitation thereto:
(i) receive a liquid sample;
(ii) evenly distribute the liquid sample in the support;
(iii) may include a reagent for changing the composition of the liquid sample, if desired;
(iv) may play the role of a filter; and
(v) may enclose any substance such as oligonucleotides.

The "enclosing zone" in the present invention is a support in the form of a sheet or strip, which is made of a material identical to or different from that of the aforementioned development element, and is placed on the development element so that it is in contact with the application zone. Examples of the material include those for the aforementioned development element, but depending on the purpose, materials different from that of the development element may be selected.

This enclosing zone may also be referred to as "conjugate pad" because of its functions, and for example, it may have the following functions without limitation thereto:
(i) may enclose any substance such as oligonucleotides; and when the analysis is not being performed, the enclosed oligonucleotides and such are normally present in a dry form;
(ii) quickly, homogeneously, and quantitatively release the respective oligonucleotides;
(iii) evenly move the respective oligonucleotides to the development element.

In the "detection zone" of the present invention, a substance for capturing and detecting a nucleic acid hybrid (nucleic acid hybrid formed by hybridization of one or more oligonucleotides to a target nucleic acid N) contained in a sample which contains various nucleic acids and has moved through the development element by capillary action, can be immobilized (for example, the aforementioned oligonucleotide R2', acceptor A' that binds to anchor A, or a substance that binds to label L2).

In the present invention, an oligonucleotide probe R2' (oligonucleotide R2') may be immobilized on the detection zone via an amino group (amino linker (for example, a linear carbon chain to which a primary amino group is bound)), carboxyl group, thiol group, hydroxyl group, and such, which may be introduced into the oligonucleotide R2'.

For example, the oligonucleotide R2' may be immobilized onto a solid phase by immobilization of the amino linker possessed by the oligonucleotide R2' onto the solid phase via a protein (for example, serum albumin, immunoglobulin, or such).

In the present invention, an acceptor A' that may bind to the anchor A possessed by the oligonucleotide probe R2' (oligonucleotide R2') can be immobilized on the detection zone.

The anchor A includes, for example, oligonucleotides, biotin, small compounds such as digoxigenin (DIG), antibodies, proteins (for example, lectin), or carbohydrate chains, and the acceptor A' includes, for example, oligonucleotides, avidin, streptavidin, antibodies, or proteins (for example, lectin). When the acceptor A' is an oligonucleotide, it may be immobilized onto the detection zone via an amino group (amino linker (for example, a linear carbon chain to which a primary amino group is bound)), carboxyl group, thiol group, hydroxyl groups, and such, as described above.

For example, when the anchor A is biotin, the acceptor A' immobilized on the detection zone may be avidin or streptavidin.

Furthermore, as described above, when different anchors A are bound to oligonucleotide probes R2' corresponding to a plurality of different target nucleic acids contained in a sample in order to detect the respective target nucleic acids N, different substances (antigens, antibodies, etc.) that bind specifically to the respective anchors A may be immobilized as acceptors A' on the respective detection zones to detect the respective target nucleic acids separately.

In the present invention, a substance (for example, antibody, streptavidin, or such) that binds to a target L2 (for example, fluorescent dye, biotin, or such) possessed by the target nucleic acid N can be immobilized on the detection zone.

For example, when the target L2 is a fluorescent dye, an antibody that specifically binds to the fluorescent dye may be immobilized on the detection zone. Furthermore, when the target L2 is biotin, the detection zone may have avidin or streptavidin immobilized thereon.

This detection zone can be referred to as "test line" because in this zone the labeled target nucleic acids N of interest contained in a sample are detected using labels L1 and L2 as indicators.

In the present invention, when the above-mentioned label L1 is, for example, a colloidal metal particle such as colloidal gold particle, a latex particle, or such, capturing of a nucleic acid hybrid containing the target nucleic acid N (nucleic acid hybrid formed by hybridization of the target nucleic acid N with one or more other oligonucleotides) by the substance immobilized on the detection zone (the aforementioned oligonucleotide R2', acceptor A' that binds to anchor A, or a substance that binds to label L2) will lead to appearance of a line of the color the particle has, such as red or blue, in the detection zone. The degree of coloration of this colored line can be used as an indicator to determine the presence and amount of the target nucleic acid N.

Furthermore, when the above-described label L2 is, for example, any of the above-described various fluorescent dyes (FITC, Texas Red, etc.), an antibody that specifically binds to the fluorescent dye and has been treated to be detectable is allowed to bind to the label L2 so that the presence and amount of the target nucleic acid N can be determined.

As described above, in the present invention, two or more different target nucleic acids contained in a sample or predicted to be contained in a sample can be simultaneously detected/quantified by using the above described lateral-flow nucleic acid chromatography (for example, the embodiments of FIGS. 4-9 to 4-12). For example, it can be performed as outlined below.

For each of the two or more different target nucleic acids N (that is, target nucleic acid $N_1$, target nucleic acid $N_2$, target nucleic acid $N_3$, target nucleic acid $N_4$, . . . target nucleic acid $N_X$ (X is an arbitrary number)), an oligonucleotide probe R1' (oligonucleotide R1') labeled with a label L1 and capable of hybridizing to the corresponding target nucleic acid $N_X$ is designed and prepared; that is, an L1-labeled oligonucleotide R1' which may hybridize to target nucleic acid $N_1$, an L1-labeled oligonucleotide R1' which may hybridize to target nucleic acid $N_2$, an L1-labeled oligonucleotide R1' which may hybridize to target nucleic acid $N_3$, an L1-labeled oligonucleotide R1' which may hybridize to target nucleic acid $N_4$, . . . and an L1-labeled oligonucleotide R1' which may hybridize to target nucleic acid $N_X$ are designed and prepared. Here, each of the target nucleic acids may be labeled with the same or different labels L2 if desired. Furthermore, a different labeling substance may be used as the label L1 for each target nucleic acid N, if desired.

For each of the two or more different target nucleic acids N (that is, target nucleic acid $N_1$, target nucleic acid $N_2$, target nucleic acid $N_3$, target nucleic acid $N_4$, . . . target nucleic acid $N_X$ (X is an arbitrary number)), an oligonucleotide probe R2 (oligonucleotide R2') for detection capable of hybridizing to the corresponding target nucleic acid N is designed and prepared; that is, a labeled oligonucleotide R2' which may hybridize to target nucleic acid $N_1$, an oligonucleotide R2' which may hybridize to target nucleic acid $N_2$, an oligonucleotide R2' which may hybridize to target nucleic acid $N_3$, an oligonucleotide R2'-4 which may hybridize to target nucleic acid $N_4$, . . . and an oligonucleotide R2' which may hybridize to target nucleic acid $N_X$ are designed and prepared. Here, the respective target nucleic acids may be labeled with the same or different labels L2 if desired. Furthermore, the oligonucleotides R2' may have the same or different anchors A.

For each of the different target nucleic acids N (that is, target nucleic acid $N_1$, target nucleic acid $N_2$, target nucleic acid $N_3$, target nucleic acid $N_4$, . . . , target nucleic acid $N_X$ (X is an arbitrary number)), at least either or both of mask oligonucleotides capable of hybridizing to regions M1 and M2 that are positioned in the target nucleic acid N so that a region R1 is positioned between them, namely oligonucleotide M1' and oligonucleotide M2', are designed and prepared. That is, at least either or both of oligonucleotides M1' and M2' which may hybridize to regions M1 and M2, respectively, that are positioned in the target nucleic acid $N_1$ so that a region R1 is positioned between them; at least either or both of oligonucleotides M1' and M2' which may hybridize to regions M1 and M2, respectively, that are positioned in the target nucleic acid $N_2$ so that a region R1 is positioned between them; at least either or both of oligonucleotides M1' and M2' which may hybridize to regions M1 and M2, respectively, that are positioned in the target nucleic acid $N_3$ so that a region R1 is positioned between them; at least either or both of oligonucleotides M1' and M2' which may hybridize to regions M1 and M2, respectively, that are positioned in the target nucleic acid $N_4$ so that a region R1 is positioned between them, . . . , and at least either or both of oligonucleotides M1' and M2' which may hybridize to regions M1 and M2, respectively, that are positioned in the target nucleic acid Nx so that a region R1 is positioned between them, are designed and prepared. Here, the respective target nucleic acids may be labeled with the same or different labels L2 if desired.

If desired, for each of the different target nucleic acids N (that is, target nucleic acid $N_1$, target nucleic acid $N_2$, target nucleic acid $N_3$, target nucleic acid $N_4$, . . . , target nucleic acid $N_X$ (X is an arbitrary number)), at least either or both of mask oligonucleotides capable of hybridizing to regions M3 and M4 that are positioned in the target nucleic acid N so that a region R2 is positioned between them, namely oligonucleotide M3' and oligonucleotide M4', are designed and prepared. That is, at least either or both of oligonucleotides M3' and M4' which may hybridize to regions M3 and M4, respectively, that are positioned in the target nucleic acid $N_1$ so that a region R2 is positioned between them; at least either or both of oligonucleotides M3' and M4' which may hybridize to regions M3 and M4, respectively, that are positioned in the target nucleic acid $N_2$ so that a region R2 is positioned between them; at least either or both of oligonucleotides M3' and M4' which may hybridize to regions M3 and M4, respectively, that are positioned in the target nucleic acid $N_3$ so that a region R2 is positioned between them; at least either or both of oligonucleotides M3' and M4' which may hybridize to regions M3 and M4, respectively, that are positioned in the target nucleic acid $N_4$ so that a region R2 is positioned between them, . . . , and at least either or both of oligonucleotides M3' and M4' which may hybridize to regions M3 and M4, respectively, in the target nucleic acid $N_X$ so that a region R2 is positioned between them are designed and prepared. Here, the respective target nucleic acids may be labeled with the same or different labels L2 if desired.

The above-mentioned respective oligonucleotides prepared for each target nucleic acid $N_X$ are hybridized to the multiple target nucleic acids $N_X$ in a sample, respectively, to form nucleic acid hybrids.

The respective nucleic acid hybrids that have moved through the development element of the device by capillary action are captured by substances (the above-mentioned oligonucleotide R2', acceptor A' which binds to anchor A, or substance that binds to label L2) immobilized on the detection zones for the respective target nucleic acids N, which are placed at different positions of the device.

When the label L1 is, for example, a colloidal metal particle such as colloidal gold particle, a latex particle, or such, the presence and amount of each of the target nucleic acids N can be determined using the degree of coloration in each of the detection zones (test lines) as an indicator.

In the lateral-type nucleic acid chromatography of the present invention, as shown schematically in FIG. 5-2, the above-described "development element" may have detection zones as test lines for detecting the above-described target nucleic acids N, and also one or two or more detection zones control lines for detecting nucleic acids that are used as internal controls. The one or two or more detection zones to be used as control lines are preferably positioned between the detection zones to be used as test lines for detecting target nucleic acids N and the later-described "absorption zone".

An internal control is a distinct nucleic acid prepared separately from the target nucleic acids N to be detected. It moves through the development element by capillary action in the same manner as the target nucleic acid N; however, it is not captured in the detection zone used as the test line where the above-described target nucleic acid N is detected, but passes through the test line and is captured and detected in the detection zone used as the control line.

An internal control can be captured and detected in the detection zone used as the control line by using a capture oligonucleotide, mask oligonucleotides, and a detection oligonucleotide that hybridize to the internal control, in a similar manner to the above-described methods for capturing and detecting a target nucleic acid N in the detection zone used as the test line.

The capturing and detection of an internal control in the detection zone as the control line aims to confirm whether the devices for performing the above-described lateral-type nucleic acid chromatography of the present invention have functioned normally or not when examining and detecting the desired target nucleic acid N using those devices, as a nucleic acid as the internal control as well as the target nucleic acid N is moved through the development element and this internal control is captured and detected in the detection zone used as the control line.

As described above, when the target nucleic acid N and internal control are detected at each detection zone using the color of metal colloid particles such as gold colloid particles or latex particles, such as red or blue, appearance of a colored line in the control line confirms that the device has functioned normally, regardless of the presence or absence of the color in the test lines. On the other hand, non-appearance of a colored line in the control line confirms that the device has not functioned normally, regardless of the presence or absence of the color in the test lines.

The "absorption zone" in the present invention can be placed in contact with the development element (for example, at the position opposite to the side where the application zone is placed) in order to absorb the liquid sample that moves through the development element by capillary action. The absorption zone may be a support in the form of a sheet or strip made of the same or different material as the above-mentioned development element.

This absorption zone may be referred to as "absorption pad" because of its functions.

In the present invention, including all embodiments described above, at least one denaturant or chaotropic agent may be present in a buffer for developing a liquid sample containing the above-described respective nucleic acids (target nucleic acids, respective oligonucleotides, nucleic acid hybrids, etc.) through the above-mentioned development element. The buffer may further contain at least one inorganic salt normally used in nucleic acid hybridization. That is, in the nucleic acid chromatography of the present invention, the presence of a denaturant or chaotropic agent promotes adequate formation of single-stranded regions in the target nucleic acid and specific binding between the target nucleic acid and the respective oligonucleotides, and reduces non-specific binding between the target nucleic acid and the respective oligonucleotides. The promotion of specific reactions enhances resolution and lowers the minimum limit of detection, and thereby increases sensitivity, accuracy, and rapidity of detection and quantification of the target nucleic acid.

In the present invention, the devices of any of the aforementioned embodiments can be placed in a case (housing) made of a moisture impermeable solid material.

One embodiment of the device of the present invention placed in this case (housing) can be exemplified by the embodiments shown schematically in FIGS. 5-1 and 5-2.

The embodiment schematically described in FIG. 5-2 is an example of preferred embodiments among the various embodiments included in the embodiment schematically described in FIG. 5-1, wherein the "development element" in the device has the above-described detection zone to be used as the test line for detecting a target nucleic acid, and also the above-described detection zone to be used as the control line for detecting a nucleic acid used as the internal control for confirming whether the device functions normally.

The case (housing) may have an opening for sample application to be used for applying a sample to the application zone of the above-described device (kit) of the present invention, and a detection window for observing the changes caused by capturing of a target nucleic acid in the detection zone (for example, change in color of the label L1).

Placing a device of the present invention into the case (housing) allows the reagents and such included in the device to be kept under dry conditions, and enables long-term storage at room temperature.

For the case (housing) made of a moisture impermeable solid material, any case (housing) employed for known or commercially available products may be used. For example, known technologies and embodiments such as the following may be prepared and used with any modifications if desired (for example, one can refer to Japanese Patent No. 2705768, Japanese Patent No. 2825349, Japanese Patent Application Kokai Publication No. (JP-A) H06-230009 (unexamined, published Japanese patent application), JP-A (Kokai) H09-145712, and JP-A (Kokai) 2000-356638).

In the present invention, the above-mentioned devices can be prepared and provided as devices for detection/quantification of a desired specific target nucleic acid N in a sample (which, in this case, are also referred to as "kits").

More specifically, for example, a device in the embodiments as exemplified above can be prepared as a kit by further providing it with one or more mask oligonucleotides (M1', M2', M3', and/or M4'), oligonucleotide probe R1' (which may be labeled with a label L1), and oligonucleotide probe R2' (which may have an anchor A) that are necessary for detecting and quantifying the specific target nucleic acid N.

In addition, for example, when a target nucleic acid N contained in a sample is detected and quantified after amplification by PCR or such, a kit in which the aforementioned kit is further provided with a pair of amplification primers (for example, PCR primers) necessary for amplifying the target nucleic acid N by PCR and such may be provided.

2. Flow-Through Nucleic Acid Chromatography

The principle of flow-through nucleic acid chromatography is basically the same as the principle of the above-mentioned lateral-flow nucleic acid chromatography. In the lateral-flow nucleic acid chromatography, hybridization of a target nucleic acid N with oligonucleotide R1' and/or oligonucleotide R2' proceeds horizontally (sideways) in the support (membrane). In contrast, in the flow-through nucleic acid chromatography, this hybridization proceeds vertically (from top to bottom).

In the present invention, this flow-through nucleic acid chromatography can be carried out, for example, by the same operations as the above-described lateral-flow nucleic acid chromatography, using a device equipped with the following components positioned in the vertical direction (from top to bottom):

- A sample pad for applying a liquid sample containing at least one or two or more different target nucleic acids N (which may be labeled with a label L2).
- A conjugate pad (also referred to as reagent paper) designed and prepared for each target nucleic acid N, which may contain one or more mask oligonucleotides (M1, M2, M3, and/or M4), one or more oligonucleotides R 1' (which may be labeled with a label L1), and/or one or more oligonucleotides R2' (which may have an anchor A), if desired.
- A detection pad (also referred to as detection paper or testing paper) on which a substance (oligonucleotide R2', acceptor A' which binds to anchor A, or a substance that binds to label L2) that may capture a nucleic acid hybrid (nucleic acid hybrid formed by hybridization of the target nucleic acid N with one or more of the above mentioned respective oligonucleotides) is immobilized to capture and detect the nucleic acid hybrid that has passed through the conjugate pad (also referred to as reagent paper).
- If desired, the device may also be equipped with an absorption pad for absorbing the liquid that has passed through the detection pad (detection paper, testing paper).

In the flow-through nucleic acid chromatography using the above-described device, when the label L1 is, for example, a colloidal metal particle such as colloidal gold particle, a latex particle, or such, capturing of the target nucleic acid N hybridized with the L1-labeled oligonucleotide R1' by a substance (oligonucleotide R2', acceptor A' which binds to anchor A, or a substance that binds to label L2) that is immobilized on the detection pad (also referred to as detection paper or testing paper) and capable of capturing the nucleic acid hybrid results in the detection pad (also referred to as detection paper or testing paper) being colored in the color the particle has, such as red or blue. The degree of this coloration can be used as an indicator to determine the presence and amount of the target nucleic acid N.

The terms used in the description of the devices for the flow-through nucleic acid chromatography and the methods for nucleic acid chromatography that uses these devices as exemplified above have the same meaning as those for the aforementioned lateral-flow nucleic acid chromatography.

3. Hybridization-ELISA

Examples of the nucleic acid detection and quantification methods of the present invention that use this method include embodiments exemplified schematically in FIG. 2 (embodiments (5), (6), and (7)) and FIG. 4-8 as described above.

In these embodiments, a target nucleic acid of interest can be detected/quantified by combining nucleic acid-nucleic acid hybridizations including hybridization of one or more mask oligonucleotides (for example, oligonucleotide M1', oligonucleotide M2', oligonucleotide M3' and/or oligonucleotide M4') and an anchor A-carrying oligonucleotide R2' to the target nucleic acid N, with reaction between a label L2 (for example, fluorescent dye, biotin, DIG, antibody, enzyme, and such) bound to the target nucleic acid N and an antibody (for example, enzyme-labeled antibody) that binds to the label L2 (that is, enzyme-linked immunoassay (ELISA)).

In the present invention, this hybridization-ELISA can be used for detecting and quantifying a target nucleic acid in a sample in the following manner, for example:

In the following, the meaning of the terms "target nucleic acid N", "region R2", "oligonucleotide probe R1'", "label L2", "L2-labeled target nucleic acid N", "region M1", "region M2", "mask oligonucleotide (oligonucleotide M1', oligonucleotide M2')", "nucleic acid hybrid", "anchor A", "acceptor A'", and such, are as defined above.

Furthermore, each of the following operations may be carried out simultaneously or in any order.

- A target nucleic acid N contained in or derived from a sample is labeled with a labeling substance (hereinafter referred to as "label L2"; examples include fluorescent dyes (fluorescein isothiocyanate (FITC), 6-carboxyfluorescein (6-FAM), TET, VIC, HEX, NED, PET, ROX, Cy5, Cy3, Texas Red, JOE, TAMRA, etc.), biotin, digoxigenin (DIG), etc.) to produce an L2-labeled target nucleic acid N. For example, when the target nucleic acid is derived from a nucleic acid amplified by PCR and such, a label L2 can be attached to amplification products during the process of gene amplification by PCR and such according to conventional methods to obtain an L2-labeled target nucleic acid N.
- At least either or both of mask oligonucleotides that hybridize to regions M1 and M2 in the target nucleic acid N, respectively, that are positioned so that a region R1 is positioned between them, namely oligonucleotide M1' and oligonucleotide M2', are designed and prepared, and at least either or both of oligonucleotides M1' and M2' are hybridized to the L2-labeled target nucleic acid N.
- Similarly, an oligonucleotide R2' which has an anchor A is hybridized to the L2-labeled target nucleic acid N.
- By performing the above-mentioned hybridizations simultaneously or in any order, one or more mask oligonucleotides and anchor A-carrying oligonucleotide R2' are hybridized to the L2-labeled nucleic acid, thereby forming a nucleic acid hybrid.
- On the other hand, an acceptor A' which is a substance that may bind to the anchor A (for example, avidin or streptavidin if the anchor A is biotin) is immobilized onto the surface of a solid support having a volume capacity (for example, a tube, vial, plate, beaker, microplate which has one or more wells, or such)
- The aforementioned mixture of the sample containing the target nucleic acid N and the respective oligonucleotides is added to the wells of the microplate, and the nucleic acid hybrid produced through the above-described hybridization is captured via binding between the anchor A and the acceptor A' immobilized on the support.
- Next, a substance that can detect the label L2 (for example, an antibody labeled with an enzyme or such which binds to label L2) is added to the reaction solution, and the color or signal generated by binding of the substance to the label L2 is detected, and the presence and amount of the target nucleic acid N is determined using the degree of the color and signal as an indicator.

Here, for example, when the label L2 is FITC, the aforementioned substance may be an anti-FITC antibody labeled with an enzyme (for example, horseradish peroxidase (HRP)).

EXAMPLES

Example 1

Detection of PCR Products of Genomic DNAs of Various Bacteria by Nucleic Acid Chromatoraphy Using Mask Oligonucleotides 1. Preparation of Template DNAs for PCR Template DNAs for PCR were prepared as genomic DNAs using ISOPLANT (NIPPON GENE).

More specifically, each of *Staphylococcus aureus* (abbreviated as "SA", bacterial strain ATCC 12600), *Staphylococcus epidermidis* (abbreviated as "SE", bacterial strain ATCC 14990), *Pseudomonas aeruginosa* (abbreviated as "PA", bacterial strain JCM5962), *Enterococcus faecalis* (abbreviated as "EF", bacterial strain JCM5803), *Escherichia coli* (abbreviated as "EC", bacterial strain JCM1649), *Enterobacter cloacae* (abbreviated as "ET", bacterial strain JCM1232), and *Klebsiella pneumoniae* (abbreviated as "KP", bacterial strain JCM 1662) was cultured overnight in 3 mL of LB liquid medium (Becton Dickinson). 1 mL of the obtained test bacterial solution was centrifuged at 6,000×g for five minutes, and then the residue was suspended in 300 µL of Extraction Buffer. Subsequently, 150 µL of Lysis Buffer was admixed, and then this was allowed to react at 50° C. for 15 minutes.

Next, 150 µL of sodium acetate (pH5.2) was added to each reaction solution and mixed, and this was left to stand on ice for 15 minutes, and then centrifuged at 12,000×g for 15 minutes at 4° C., and the supernatant was collected. To each supernatant, 2.5 volumes of 100% ethanol was added, and this was mixed, and then centrifuged at 12,000×g for 15 minutes at 4° C. The residue was washed with 70% ethanol and then air-dried. 100 µL of TE buffer [10 mM Tris-HCl (pH 8.0), 1 mM Ethylenediamine tetraacetic acid (EDTA)] was added to the air-dried residue to dissolve it, then 1 µL of RNase A (final concentration of 10 µg/mL) was added thereto, and this was allowed to react at 37° C. for 30 minutes. 100 µL of phenol saturated with TE buffer was added thereto, and this was mixed. This was centrifuged at 12,000×g for 15 minutes, and then the supernatant was collected. 10 µL of 3 M sodium acetate buffer (pH6.0) and 2.5 volumes of 100% ethanol were added thereto, and this was mixed. Then, this was centrifuged at 12,000×g for ten minutes, and then the supernatant was discarded. 100 µL of ice-cold 70% ethanol was added thereto, and this was centrifuged at 12,000×g for ten minutes. The residue was air-dried, and then dissolved in 50 µL of TE buffer to prepare the template DNA.

2. Nucleic Acid Amplification by PCR

PrimeSTAR HS DNA Polymerase from TAKARA was used for the PCR. First, 0.2 µL of PrimeSTAR HS DNA Polymerase (2.5 U/µL), 4 µL of 5× PrimeSTAR Buffer (Mg²⁺ plus), 1.6 µL of dNTP mixture (2.5 mM each), 1 µL of template DNA, and 0.4 µL each of a pair of oligonucleotide primers (10 pmol/µL) that are specific to the corresponding bacteria-derived template genomic DNA were combined and, the volume was adjusted to 20 µL using sterilized water.

SA1F and SA1R shown below were used as the PCR primers for SA.

```
SA1F:
                                        [SEQ ID NO: 1]
5'-GGATTCAATGTCACATGAGCGTGATAAAAT-3'

SA1R:
                                        [SEQ ID NO: 2]
5'-AAAGCTCAAGGATATGCGATTACTGAAGCAG-3'
```

SE1F and SE1R shown below were used as the PCR primers for SE.

```
SE1F:
                                        [SEQ ID NO: 3]
5'-TCAGAGGTCATGGAAAATCTTCACGAAC-3'

SE1R:
                                        [SEQ ID NO: 4]
5'-ATTGCCTCAGATTTATTAAAGCCTGCTAATTCTTC-3'
```

PA1F and PA1R shown below were used as the PCR primers for PA.

```
PA1F:
                                        [SEQ ID NO: 5]
5'-AAGATCGGCGTATTCATCGGCGTC-3'

PA1R:
                                        [SEQ ID NO: 6]
5'-CCCAGGTCCTGATAGACCAGTTGATACCC-3'
```

EF1F and EF1R shown below were used as the PCR primers for EF.

```
EF1F:
                                        [SEQ ID NO: 7]
5'-GAAGACAACGATTTATGTTTACGCTTTGGCA-3'

EF1R:
                                        [SEQ ID NO: 8]
5'-AATTCGGCGTATCAGCCATTTTCATTT-3'
```

EC1F and EC1R shown below were used as the PCR primers for EC.

```
EC1F:
                                        [SEQ ID NO: 9]
5'-GTCAGGTAAGGCTAATTTCATTACCAGCAAAGG-3'
(the same sequence as oligonucleotide EFA1 of SEQ
ID NO: 41)

EC1R:
                                        [SEQ ID NO: 10]
5'-CGGTCAGCCATAGGGTAAATGACCAC-3'
```

ET1F and ET1R shown below were used as the PCR primers for ET.

```
ET1F:
                                        [SEQ ID NO: 11]
5'-GTTTCTGGCACGGCGTCAGC-3'

ET1R:
                                        [SEQ ID NO: 12]
5'-TGTGTGTCTAATCAGTTCCGCAGGG-3'
```

KP1F and KP1R shown below were used as the PCR primers for KP.

```
KP1F:
                                      [SEQ ID NO: 13]
5'-CAGCCATCAGGTTGAGCATCATTAATCTT-3'

KP1R:
                                      [SEQ ID NO: 14]
5'-CAGCCGGAGAAATAGAGAAATCTTATGAATCAT-3'
```

PCR was performed on the Veriti Thermal Cycler (Applied Biosystems) under the following conditions: maintaining at 94° C. for 3 minutes; then repeating 40 cycles of reaction at 98° C. for 10 seconds and 68° C. for 1 minute; and then maintaining at 68° C. for 5 minutes.

3. Evaluation of PCR Products by Agarose Gel Electrophoresis

The amplified PCR products were separated by agarose gel electrophoresis using Mupid (Advance) with the use of 2% agarose (Agarose I, AMRESCO) and 1×TAE buffer [40 mM Tris-HCl (pH 8.0), 40 mM acetic acid, 1.0 mM EDTA]. Electrophoresis was followed by staining using a solution of 1 μg/mL ethidium bromide, and the stained DNA was photographed under ultraviolet light (260 nm) using a gel documentation analysis system ChemiDoc XRS (Bio-Rad Laboratories, Inc.).

4. Preparation of Capture Oligonucleotides Labeled with Colloidal Gold Particles A capture oligonucleotide labeled with colloidal gold particles to be used for detection of EC-derived nucleic acids by nucleic acid chromatography, was prepared as follows.

The synthesized, biotinylated oligonucleotide (biotin-CGGTCAACGAGATGTGGTCT-3') [SEQ ID NO: 15] was weighed, and 1 mM EDTA was added thereto, and this was diluted with 0.1 M 3-Morpholinopropanesulfonic acid (MOPS) buffer (pH7.8), to prepare a solution of 0.15 nmol biotinylated oligonucleotide.

To the biotinylated oligonucleotide solution, streptavidin-bound colloidal gold particles (manufactured by BBI) were added at an equal amount, and this was mixed well, and then incubated at 37° C. for one hour. Next, a biotin solution was added to this solution at a final concentration of 0.1%, and this was incubated further at 37° C. for 15 minutes. The obtained mixed solution was centrifuged at 15,000×g for five minutes, then the supernatant was discarded, and 1 mM EDTA and 5 mL of 0.5% BSA-supplemented 20 mM Tris-HCl (8.0) were added thereto. This was centrifuged at 15,000×g for five minutes, and the supernatant was removed. 1 mM EDTA and 0.5% BSA-supplemented 20 mM Tris-HCl (8.0) were added thereto and stirred. This was used as the solution of capture oligonucleotide labeled with colloidal gold particles to be used in detecting the EC-derived nucleic acids.

Capture oligonucleotides labeled with colloidal gold particles to be used in the detection of nucleic acids derived from various bacteria (SA, SE, PA, EF, ET, and KP) by nucleic acid chromatography, were prepared by a method similar to that described above.

The sequences of the above capture oligonucleotides were the following.

```
For SA nucleic acid detection (SAB):
                                      [SEQ ID NO: 16]
5'-GGCTCATCTTCTAGTGGTGC-3'

For SE nucleic acid detection (SEB):
                                      [SEQ ID NO: 17]
5'-GGCCAAAAGTGAAGACATTG-3'

For PA nucleic acid detection (PAB):
                                      [SEQ ID NO: 18]
5'-CCATCTTTTCCAGGCGATGC-3'

For EF nucleic acid detection (EFB):
                                      [SEQ ID NO: 19]
5'-ACAAATGGGGCTGGAGGTTC-3'

For ET nucleic acid detection (ETB):
                                      [SEQ ID NO: 20]
5'-CAACCCTCAGGACACCACTT-3'

For KP nucleic acid detection (KPB):
                                      [SEQ ID NO: 21]
5'-CAACTCGGGATCGGCAAACA-3'
```

5. Preparation of BSA-Bound Detection Oligonucleotides

A BSA-bound detection oligonucleotide to be immobilized onto a membrane for use in detecting EC-derived nucleic acids by nucleic acid chromatography, was prepared as follows. 150 mg of bovine serum albumin (BSA) manufactured by Sigma was dissolved in 2 mL of 0.1 M phosphate buffer (pH6.7) supplemented with 5 mM EDTA.

Next, N-succinimidyl-S-acetylthioacetate (SATA) manufactured by Thermo Scientific was prepared at 4-times the molar amount of BSA, and this was incubated at 37° C. for 90 minutes. Thereafter, a hydroxyamine solution was added to the mixed solution at a final concentration of 0.5 M, and this was incubated further at 37° C. for 60 minutes. 2 M phosphate buffer was added to these mixed solutions, and pH was adjusted to 6.0 to produce maleimide-modified BSA solutions.

The synthesized oligonucleotide (5'-CGACAGTACGCAGCCACGAT-3') [SEQ ID NO: 22] was weighed, and then diluted using 0.1 M phosphate buffer (pH6.0) supplemented with 5 mM EDTA, to produce an oligonucleotide solution at 650 nmol/mL. N-[6-Maleimidocaproyloxy]succinimide (EMCS) manufactured by Dojindo was prepared at 50-times the molar amount of the oligonucleotide, and this was mixed with the oligonucleotide solution, and then incubated at 37° C. for 30 minutes. Thereafter, ethanol precipitation was carried out according to an ordinary method.

0.1 M phosphate buffer (pH6.0) supplemented with 5 mM EDTA was added to the precipitate to dissolve it, and the same amount of a maleimide-modified BSA solution was added thereto, and this was incubated at 37° C. for 60 minutes. Thereafter, N-ethylmaleimide was added at a final concentration of 0.1%. The total amount of the mixture containing maleimide-modified BSA and the oligonucleotide was purified using an ACA44-packed column (internal diameter of 1.5 cm×60 cm) manufactured by Bio Sepra by elution using 0.1 M phosphate buffer (pH6.0) supplemented with 5 mM EDTA.

BSA-bound detection oligonucleotides to be immobilized onto the membrane in the detection of nucleic acids derived from various bacteria (SA, SE, PA, EF, ET, and KP) by nucleic acid chromatography, were prepared by a method similar to that described above.

The sequences of the detection oligonucleotides bound to BSA were the following.

```
For SA nucleic acid detection (SAA):
                                            [SEQ ID NO: 23]
5'-GCCGTGCTCAATACAGCTCC-3'

For SE nucleic acid detection (SEA):
                                            [SEQ ID NO: 24]
5'-GGACATGATATGGGGGGCAT-3'

For PA nucleic acid detection (PAA):
                                            [SEQ ID NO: 25]
5'-CGAGACGGCCCCAGACCTAT-3'

For EF nucleic acid detection (EFA):
                                            [SEQ ID NO: 26]
5'-AAGCAGGCTATCGGATTCTC-3'

For ET nucleic acid detection (ETA):
                                            [SEQ ID NO: 27]
5'-GTGGCTGACCTTAATGAACC-3'

For KP nucleic acid detection (KPA):
                                            [SEQ ID NO: 28]
5'-ATCACTGGCTGGCAAGGCAC-3'
```

6. Preparation of Test Strip to be Used for Nucleic Acid Chromatography

Using XYXZ300 Dispense Platform manufactured by BioDot, a BSA-bound detection oligonucleotide was applied at 1.1 µg/test ("one test" means a line having a width of 1 mm×5 mm) onto a nitrocellulose membrane manufactured by Advanced Microdevice. This was dried overnight at room temperature, and thus the detection oligonucleotide was immobilized on the test line on the membrane via BSA.

Next, the membrane immobilized with the detection oligonucleotide was soaked in 0.1 M phosphate buffer (pH 6.0) supplemented with 2% BSA at 4° C. overnight for blocking. Then, the membrane was sufficiently dried at room temperature. To the dried membrane carrying the immobilized detection oligonucleotide, a sample pad manufactured by Advanced Microdevice, a water absorbing pad, and a conjugate pad manufactured by Nihon Pall Ltd. were pasted together. The pasted sheets were cut into 5-mm-wide strips using a BioDot guillotine cutter to produce test strips for use in nucleic acid chromatography (FIG. 5-1).

Using the BSA-bound detection oligonucleotides prepared for each bacterium as described above, test strips were prepared for each of the bacteria.

7. Preparation of Mask Oligonucleotides

A pair of mask oligonucleotides that hybridize to the 5'-side and 3'-side regions, respectively, of the site on a bacterial genomic nucleic acid to which the capture oligonucleotide prepared as mentioned above hybridizes, and which is positioned between the above regions, were prepared for each type of bacteria.

Similarly, a pair of mask oligonucleotides that hybridize to the 5'-side and 3'-side regions, respectively, of the site on a bacterial genomic nucleic acid to which the detection oligonucleotide prepared as mentioned above hybridizes, and which is positioned between the above regions, were prepared for each type of bacteria.

The sequences of the prepared mask oligonucleotides were the following.

```
For SA nucleic acid detection (SAA1):
                                            [SEQ ID NO: 29]
5'-CAGTAATATAATAGTCTTTATCTACACTTTCTAAT-3'

For SA nucleic acid detection (SAA2):
                                            [SEQ ID NO: 30]
5'-ACTTGTAGAGACACCCGTTAATACT-3'

For SA nucleic acid detection (SAB1):
                                            [SEQ ID NO: 31]
5'-TAAAGCGTCGCTTAGAAATAATC-3'

For SA nucleic acid detection (SAB2):
                                            [SEQ ID NO: 32]
5'-TAAATCTTCAAGTATTCGTGTAGATG-3'

For SE nucleic acid detection (SEA1):
                                            [SEQ ID NO: 33]
5'-TAAATATCGATTCTGCACATATTTTA-3'

For SE nucleic acid detection (SEA2):
                                            [SEQ ID NO: 34]
5'-CATTGCGAGTGAATTTACTG-3'

For SE nucleic acid detection (SEB1):
                                            [SEQ ID NO: 35]
5'-GTGATTACATTGACAATTGTTTC-3'

For SE nucleic acid detection (SEB2):
                                            [SEQ ID NO: 36]
5'-CAAATGGTTTCAACAAATTAATG-3'

For PA nucleic acid detection (PAA1):
                                            [SEQ ID NO: 37]
5'-AGCCTAGTCCAGCGGG-3'

For PA nucleic acid detection (PAA2):
                                            [SEQ ID NO: 38]
5'-TTGTCATTACGGGGCGT-3'

For PA nucleic acid detection (PAB1):
                                            [SEQ ID NO: 39]
5'-GACCTCAGGCCGTTAACAT-3'

For PA nucleic acid detection (PAB2):
                                            [SEQ ID NO: 40]
5'-CGTGCATCGGGCTGTG-3'

For EF nucleic acid detection (EFA1):
                                            [SEQ ID NO: 41]
5'-GAAGACAACGATTTATGTTTACGCTTTGGCA-3'
(the same as the sequence for oligonucleotide EC1F
of SEQ ID NO: 9)

For EF nucleic acid detection (EFA2):
                                            [SEQ ID NO: 42]
5'-TATACGCCTTTTGAAACGGT-3'

For EF nucleic acid detection (EFB1):
                                            [SEQ ID NO: 43]
5'-AATCAATGGGGAAATTTTTTA-3'

For EF nucleic acid detection (EFB2):
                                            [SEQ ID NO: 44]
5'-TTTTAATGAGTCAAAGATTAGCGG-3'

For EC nucleic acid detection (ECC1):
                                            [SEQ ID NO: 45]
5'-TAACAGTAAGCTGGTCATGG-3'

For EC nucleic acid detection (ECC2):
                                            [SEQ ID NO: 46]
5'-CAGTACAACACGACGATTTATG-3'

For EC nucleic acid detection (ECD1):
                                            [SEQ ID NO: 47]
5'-GATCGCTATCGAGGGGTATT-3'

For EC nucleic acid detection (ECD2):
                                            [SEQ ID NO: 48]
5'-TTATGAGTGCTAAACAAGCTAAA-3'
```

-continued

```
For ET nucleic acid detection (ETA1):
                                        [SEQ ID NO: 49]
5'-GGTCAACACCCCACAGGA-3'

For ET nucleic acid detection (ETA2):
                                        [SEQ ID NO: 50]
5'-AAATCATTCAAAAGAATGCTGAAC-3'

For ET nucleic acid detection (ETB1):
                                        [SEQ ID NO: 51]
5'-TGGCGGTATGGATGGG-3'

For ET nucleic acid detection (ETB2):
                                        [SEQ ID NO: 52]
5'-TGCTGCATACGCTCTCTGA-3'

For KP nucleic acid detection (KPA1):
                                        [SEQ ID NO: 53]
5'-CGCGGCCCTTTTTT-3'

For KP nucleic acid detection (KPA2):
                                        [SEQ ID NO: 54]
5'-ATATTGCCATTGTTTATTTTTC-3'

For KP nucleic acid detection (KPB1):
                                        [SEQ ID NO: 55]
5'-CTATTTTTAGCAGCTTGTTCAA-3'

For KP nucleic acid detection (KPB2):
                                        [SEQ ID NO: 56]
5'-CTCATTTACCAGGAATAATCTTAC-3'
```

8. Detection of Nucleic Acids by Nucleic Acid Chromatography

The test strips prepared for each of the bacteria as described above were used for nucleic acid chromatography (FIG. 5-1). The detection oligonucleotides prepared as described above were immobilized via BSA to the test line.

To 10 μL of a solution of PCR products from a genomic nucleic acid derived from each of the bacteria, which was prepared as described above, 1 μL of the oligonucleotides for masking (4 μM each) was added. 49 μL of development buffer (28.6% formamide, 1.43×SSC, 0.143% BSA, 1.43 mM EDTA, 0.143% dextran sulfate) for nucleic acid chromatography was added thereto, and this was treated at 95° C. for five minutes, and then rapidly cooled at 4° C. Subsequently, 10 μL of the capture oligonucleotide labeled with colloidal gold particles, which was produced as described above, was added to the solution, and the whole amount was added dropwise to the sample pad (FIG. 5-1) of a membrane (test strip).

As a control experiment, nucleic acid chromatography was performed similarly without the use of the mask oligonucleotides.

9. Results

FIG. 6 shows the results of detection by agarose gel electrophoresis of PCR products obtained using the respective genomic DNAs of the bacteria as templates.

The results show that the genomic DNA of interest for each of the bacteria was amplified by PCR.

The results of performing nucleic acid chromatography on PCR-amplified genomic DNA of each of the bacteria are shown in FIG. 7.

As a result, the use of mask oligonucleotides remarkably increased the coloring sensitivity.

Example 2

Detection of Restriction Enzyme-Treated Fragments of Bacterial Genomic DNAs by Nucleic Acid Chromatography Using Mask Oligonucleotides 1. Preparation of Bacterial Genomic DNAs

*Escherichia coli* (abbreviated as "EC" below; bacterial strain JCM1649) and *Enterobacter cloacae* (abbreviated as "ET" below; bacterial strain JCM1232) were cultured overnight in 5 mL of BHI liquid medium (Becton Dickinson). The test bacterial solution was centrifuged at 1,870×g (Allegra 6KR Centrifuge, Becton Dickinson) for ten minutes, and the supernatant was discarded. The remainder was washed with TE buffer [10 mM Tris-HCl (pH 8.0), 1 mM Ethylenediamine tetraacetic acid (EDTA)], and centrifuged again at 1,870×g for ten minutes, and the supernatant was discarded. The remainder was suspended in 900 L of TE buffer. Next, 300 μL of 5 mg/mL lysozyme (SEIKAGAKU CORPORATION) was added to the suspension solution, and the treatment was carried out at 37° C. for 30 minutes. Subsequently, 150 μL of 10 mg/mL Protease K (Roche Diagnostics) was added thereto, and the treatment was carried out at 37° C. for 30 minutes, and then, 150 L of 10% SDS was added thereto.

To this solution, an equivalent amount of phenol saturated with TE was added, and this was mixed. Then, the mixture was centrifuged at 1,870×g for ten minutes, and the supernatant was collected. The above operation was repeated and the supernatant was collected. Next, to the collected supernatant solution, 4 mL of cold ethanol was added, and this was mixed to precipitate genomic DNA. Genomic DNA was collected by winding it to a platinum loop, and then this was washed with cold 70% ethanol, and air-dried, and subsequently dissolved in 500 μL of TE. Next, 20 μL of 0.5 mg/mL RNase A (Roche Diagnostics) was added to the solution, and the treatment was carried out at 37° C. for two hours. Subsequently, 20 μL of 10 mg/mL Protease K (Roche Diagnostics) was added thereto, and the treatment was carried out at 55° C. for one hour.

To this solution, an equivalent amount of TE-saturated phenol/chloroform solution was added, and this was mixed. Then, this mixture was centrifuged at 1,870×g for ten minutes, and the supernatant was collected. The above operation was repeated two more times to obtain a supernatant solution. Subsequently, 1 mL of ether was added to the obtained supernatant solution, and this was mixed. This was centrifuged at 1,870×g for ten minutes, then the supernatant was discarded. The same operation was repeated, and then ether was evaporated by air drying. 2 mL of cold ethanol was added thereto and this was mixed to precipitate the genomic DNA. Genomic DNA was collected by winding it to a platinum loop, and then this was washed with cold 70% ethanol, and air-dried. Subsequently, this was dissolved in 200 μL of TE to obtain a bacterial genomic DNA solution.

2. Treatment of Bacterial Genomic DNA with a Restriction Enzyme

Bgl II (TAKARA BIO) was used for the restriction enzyme. 150 μg of the bacterial genome obtained as described above, 250 μL of H buffer, and 100 μL of Bgl II (10 U/μL) were combined, and the volume was adjusted to 2.5 mL using sterilized water, and this was allowed to react at 37° C. for 16 hours. Next, 5 mL of cold ethanol was added to the reaction solution, and this was mixed. DNA was precipitated by centrifugation at 20,000×g for ten minutes. After discarding the supernatant, the remainder was washed with cold 70% ethanol. This was air-dried and then dissolved in 50 L of TE to obtain the restriction-enzyme-treated bacterial genomic DNA fragments.

3. Preparation of a Capture Oligonucleotide Labeled with Colloidal Gold Particles A 5'-end thiol-modified oligonucleotide was dissolved in sterilized distilled water to produce a 200 µM solution. To 200 µL of this solution, 200 µL of 0.08 M dithiothreitol (DTT) was added, and this was left to stand at room temperature for 16 hours. Thereafter, solvent displacement was performed using sterilized distilled water. 200 µL of 10 µM 5'-end thiol-modified oligonucleotide was mixed with 200 µL of a colloidal gold particle solution (Wine Red Chemical Co., or British BioCell International), and then this was left to stand at 50° C. for 22 hours. Next, 200 µL of 200 µM dATP was added thereto and this was allowed to stand for 6 hours. The final concentrations were adjusted to 0.1 M NaCl and 10 mM phosphate buffer (pH7.0), and this was left to stand for another 12 hours. This was followed by centrifugation at 5,000×g for 15 minutes. Then, the same buffer was used for washing and re-dispersion, to obtain a capture oligonucleotide labeled with colloidal gold particles to be used for nucleic acid chromatography. As necessary, the same buffer containing 0.1% polyethylene glycol (PEG; molecular weight of 20,000) was used.

The sequence of the above-mentioned capture oligonucleotide was the following:

```
For ET nucleic acid detection (ETB2-2):
                                  (SEQ ID NO: 57)
  5'-GTGCCGCTCACCACACCATT-3'
```

4. Preparation of a BSA-Bound Detection Oligonucleotide

The preparation was carried out by a method similar to that of Example 1.

The sequence of the detection oligonucleotide was the following:

```
For ET nucleic acid detection (ETA2-2):
                                  (SEQ ID NO: 58)
  5'-TCACGACGACGAACGTACGC-3'
```

5. Preparation of Test Strips to be Used for Nucleic Acid Chromatography

Using XYXZ300 Dispense Platform manufactured by BioDot, a BSA-bound detection oligonucleotide was applied at 1.1 µg/test ("one test" means a line having a width of 1 mm×5 mm) onto a nitrocellulose membrane manufactured by Advanced Microdevice. By drying this overnight at room temperature, the detection oligonucleotide was immobilized to the test line on the membrane via BSA.

Next, the membrane immobilized with the detection oligonucleotide was soaked in 0.1 M phosphate buffer (pH6.0) supplemented with 2% BSA at 4° C. overnight for blocking. Then, the membrane was sufficiently dried at room temperature. To the dried membrane immobilized with the detection oligonucleotide, a sample pad manufactured by Advanced Microdevice, a water absorbing pad, and a conjugate pad manufactured by Nihon Pall Ltd. were pasted together. The pasted sheets were cut into 5-mm-wide strips using a BioDot guillotine cutter to produce test strips for use in nucleic acid chromatography (FIG. 1).

6. Preparation of Mask Oligonucleotides

A pair of mask oligonucleotides that hybridize to the 5'-side and 3'-side regions, respectively, of the site on a bacterial genomic DNA nucleic acid to which the capture oligonucleotide prepared as described above hybridizes, and which is positioned between the above regions, was prepared for each type of bacteria.

Similarly, a pair of mask oligonucleotides that hybridize to the 5'-side and 3'-side regions, respectively, of the site on a bacterial genomic nucleic acid to which the detection oligonucleotide prepared as described above hybridizes, and which is positioned between the above regions, was prepared for each type of bacteria.

The sequences of the prepared mask oligonucleotides were the following:

```
For ET nucleic acid detection (ETA3):
                                  [SEQ ID NO: 59]
  5'-ACCAGTGGGGAGATCACG-3'

For ET nucleic acid detection (ETA4):
                                  [SEQ ID NO: 60]
  5'-GATAAACTCGTTACCGGTCA-3'

For ET nucleic acid detection (ETB3):
                                  [SEQ ID NO: 61]
  5'-AGAACAGCCTGCAGGAGA-3'

For ET nucleic acid detection (ETB4):
                                  [SEQ ID NO: 62]
  5'-AACTACGTATGGCTGAGCC-3'
```

7. Detection of Nucleic Acids by Nucleic Acid Chromatography

The test strips prepared as described above were used for nucleic acid chromatography (FIG. 5-1). The detection oligonucleotides prepared as described above were immobilized via BSA to the test line.

To 10 µL of a solution of bacterial (ET or EC) genomic DNA fragments prepared as described above by restriction enzyme treatment, 1 µL of the oligonucleotides for masking (4 µM each) was added. 49 µL of development buffer (28.6% formamide, 1.43×SSC, 0.143% BSA, 1.43 mM EDTA, 0.143% dextran sulfate) for nucleic acid chromatography was added thereto. After treatment at 95° C. for five minutes, the mixture was rapidly cooled at 4° C. Subsequently, 10 µL of the capture oligonucleotide labeled with colloidal gold particles, which was prepared as described above, was added to the solution, and the whole amount was added dropwise to the sample pad (FIG. 5-1) of the membrane (test strip).

As a control experiment, nucleic acid chromatography was performed similarly without the use of the mask oligonucleotides.

8. Results

FIG. 8 shows the results of nucleic acid chromatography on bacterial genomic DNA fragments obtained by restriction enzyme treatment.

As a result, the use of oligonucleotides for masking enabled highly sensitive detection of target nucleic acids, even when the nucleic acid to be detected was bacterial genomic DNA and not PCR products.

Example 3

Specific Detection of Target Nucleic Acids in PCR Products Obtained by Multiplex PCR on Bacterial Genomic DNAs Using Nucleic Acid Chromatography with Mask Oligonucleotides 1. Preparation of Template Genomic DNAs for Multiplex PCR

*Campylobacter jejuni* (bacterial strain ATCC700819), *Campylobacter jejuni* (bacterial strain 81-176), *Campylobacter coli* (bacterial strain ATCC33559), *Campylobacter* coli (bacterial strain ATCC43478), *Campylobacter fetus* (bacterial strain ATCC27374), *Campylobacter fetus* (bacterial strain ATCC 19438), *Campylobacter hyointestinalis* (bacterial strain ATCC35217), *Campylobacter lari* (bacterial strain ATCC43675) and *Campylobacter upsaliensis* (bacterial strain ATCC43956) were cultured on a blood agar medium at 37° C. for 3 days under microaerophilic conditions. Colonies obtained from each of the bacterial strains were suspended in TE, and template genomic DNAs were prepared by a boiling method. More specifically, the suspension solutions were boiled for ten minutes in a boiling water bath, and rapidly cooled on ice-water, then centrifuged at 12,000×g for ten minutes. Then, the supernatant was collected to obtain the template genomic DNAs.

Furthermore, *E. coli* (bacterial strain C600) was cultured overnight in a BHI liquid medium (Becton Dickinson), then subjected to ten-fold dilution using TE, and the template genomic DNAs were prepared in a similar manner from the obtained diluted solution using the boiling method.

2. Nucleic Acid Amplification by Multiplex PCR

Ex Taq DNA Polymerase from TAKARA was used for the PCR. First, 0.2 μL of Ex Taq DNA Polymerase (2.5 U/μL), 4 μL of 10× Ex Taq Buffer, 3.2 μL of dNTP Mixture (2.5 mM each), 1 μL of template genomic DNA, and the following pairs of oligonucleotide primers respectively specific to the cdtC genes in the template genomic DNAs of the three bacterial species, *Campylobacter jejuni*, *Campylobacter coli*, and *Campylobacter fetus* (2 μL each, 10 pmol/μL, 12 μL in total), were combined and the volume was adjusted to 40 μL using sterilized water to perform multiplex PCR. PCR was performed on Veriti Thermal Cycler (Applied Biosystems) under the following conditions: maintaining the reaction system at 94° C. for three minutes; then repeating 30 cycles of the reactions at 94° C. for 30 seconds, 55° C. for 30 seconds, and 72° C. for 30 seconds; and then maintaining at 72° C. for three minutes.

CjcdtCU1 and CjcdtCR2 shown below were used as the PCR primers for *Campylobacter jejuni*.

```
CjcdtCU1:
                                     [SEQ ID NO: 63]
5'-TTTAGCCTTTGCAACTCCTA-3'

CjcdtCR2:
                                     [SEQ ID NO: 64]
5'-AAGGGGTAGCAGCTGTTAA-3'
```

CccdtCU1 and CccdtCR1 shown below were used as the primers for *Campylobacter coli*.

```
CccdtCU1:
                                     [SEQ ID NO: 65]
5'-TAGGGATATGCACGCAAAAG-3'

CccdtCR1:
                                     [SEQ ID NO: 66]
5'-GCTTAATACAGTTACGATAG-3'
```

CfcdtCU2 and CfcdtCR1 shown below were used as the primers for *Campylobacter fetus*.

```
CfcdtCU2:
                                     [SEQ ID NO: 67]
5'-AAGCATAAGTTTTGCAAACG-3'

CfcdtCR1:
                                     [SEQ ID NO: 68]
5'-GTTTGGATTTTCAAATGTTCC-3'
```

4. Evaluation of PCR Products by Agarose Gel Electrophoresis

The PCR products amplified by multiplex PCR were separated by agarose gel electrophoresis with Mupid (Advance) using 2% agarose (Agarose I, AMRESCO) and 1×TAE buffer [40 mM Tris-HCl (pH 8.0), 40 mM Acetic acid, 1.0 mM EDTA]. After electrophoresis, the gel was stained using an ethidium bromide solution at 1 μg/mL, and the stained DNA was photographed under ultraviolet light (260 nm) using a gel documentation analysis system Chemi-Doc XRS (Bio-Rad Laboratories, Inc.).

5. Preparation of Capture Oligonucleotides Labeled with Colloidal Gold Particles Oligonucleotides labeled with colloidal gold particles to be used in the detection of genomic DNAs from the bacteria by nucleic acid chromatography, were prepared by a method similar to that of Example 2.

The sequences of the capture oligonucleotides for detecting each of the bacteria were the following.

```
For Cj nucleic acid detection (Cj-SH):
                                     [SEQ ID NO: 69]
5'-CCTTGCACCCTAGATCCTAT-3'

For Cc nucleic acid detection (Cc-SH):
                                     [SEQ ID NO: 70]
5'-TCCTGACTCTAGTATCGCCA-3'

For Cf nucleic acid detection (Cf-SH):
                                     [SEQ ID NO: 71]
5'-TCAGATCGCTCCTAGCGGAT-3'
```

6. Preparation of BSA-Bound Detection Oligonucleotides

To 400 μL of 0.1 M 3-Morpholinopropanesulfonic acid (MOPS) buffer containing 100 nmol of 5'-end aminated oligonucleotide, 3.5 mg/50 μL of N-[6-Maleimidocaproyloxy]succinimide (EMCS) was added, and this was allowed to react at 37° C. for 30 minutes. After the reaction, ethanol precipitation was carried out for purification, and the purified product was dissolved in 5 mM ethylenediaminetetraacetic acid (EDTA) and 0.1 mM phosphate buffer (pH6.0). The amount of oligonucleotides introduced with maleimide group was determined by the absorbance at 260 nm.

N-succinimidyl-S-acetylthioacetate (SATA) was introduced to Bovine Serum Albumin (BSA) using a Sulfhydryl Addition Kit (Thermo scientific). More specifically, 16 μL of 17.3 mM SATA solution was added to 1 mL of phosphate buffered saline (PBS) with 2 mg of dissolved BSA, and this was allowed to react at room temperature for 30 minutes. Next, 100 μL of Conjugation Buffer Stock (10×) with 5 mg of dissolved hydroxylamine-HCl was added thereto, and this was allowed to react at room temperature for two hours. This was followed by solvent exchange with Maleimide Conjugation Buffer. The amount of SH-group-introduced BSA was determined from the absorbance of the collected eluate at 280 nm, and this was used in the subsequent reaction.

The maleimide-group-introduced oligonucleotide and the SH-group-introduced BSA, which were prepared as described above, were mixed and allowed to react at 37° C. for one hour to prepare a BSA-bound detection oligonucleotide. After the reaction, the BSA-bound detection oligonucleotide was concentrated using Amicon Ultra 30K (Millipore), and the amount was measured using Quick Start Bradford 1× Dye Reagent (Bio-Rad).

The sequences of the detection oligonucleotides for detecting each of the bacteria were the following.

```
For Cj nucleic acid detection (Cj-NH):
                                [SEQ ID NO: 72]
5'-AGCGCCTTTAGGGATACCTC-3'

For Cc nucleic acid detection (Cc-NH):
                                [SEQ ID NO: 73]
5'-TAAGCCCTAGGGGCGATGAT-3'

For Cf nucleic acid detection (Cf-NH):
                                [SEQ ID NO: 74]
5'-ACGCAATGCAAACACCGGAA-3'
```

6. Preparation of Mask Oligonucleotides

A pair of mask oligonucleotides that hybridize to the 5'-side and 3'-side regions, respectively, of the site on a bacterial genomic DNA nucleic acid to which the capture oligonucleotide prepared as described above hybridizes, and which is positioned between the above regions, was prepared for each type of bacteria.

Similarly, a pair of mask oligonucleotides that hybridize to the 5'-side and 3'-side regions, respectively, of the site on a bacterial genomic nucleic acid to which the detection oligonucleotide prepared as described above hybridizes, and which is positioned between the above regions, was prepared for each type of bacteria.

The sequences of the prepared mask oligonucleotides were the following.

```
For Cj nucleic acid detection (Cjf1):
                                [SEQ ID NO: 75]
5'-GCTTAGAAACGGGAATTTTTTA-3'

For Cj nucleic acid detection (Cjf2):
                                [SEQ ID NO: 76]
5'-AAAAGATCCTATTGATCAAAATTGG-3'

For Cj nucleic acid detection (Cjg1):
                                [SEQ ID NO: 77]
5'-AAAACGCTTTGGAATAGCC-3'

For Cj nucleic acid detection (Cjg2):
                                [SEQ ID NO: 78]
5'-TTTTTTTGCTGAAGTAAATGAAC-3'

For Cc nucleic acid detection (Ccf1):
                                [SEQ ID NO: 79]
5'-GCCTTTTGGCTATGTTCAGTTTA-3'

For Cc nucleic acid detection (Ccf2):
                                [SEQ ID NO: 80]
5'-ATATGCCTAGCTGTTTTAAGTGAA-3'

For Cc nucleic acid detection (Ccg1):
                                [SEQ ID NO: 81]
5'-CAATCAATGCATGAGCACTTT-3'

For Cc nucleic acid detection (Ccg2):
                                [SEQ ID NO: 82]
5'-TAGAAAATCGCTTTGGTTTAGG-3'

For Cf nucleic acid detection (Cff1):
                                [SEQ ID NO: 83]
5'-CATAACCGACGCTTTTCAAAT-3'

For Cf nucleic acid detection (Cff2):
                                [SEQ ID NO: 84]
5'-TTCCTATAAATATAAAGCGATTTTCAG-3'

For Cf nucleic acid detection (Cfg1):
                                [SEQ ID NO: 85]
5'-CCGACGTAAAAATGTGCCT-3'

For Cf nucleic acid detection (Cfg2):
                                [SEQ ID NO: 86]
5'-TTTTAGCACTAAAAAACTGCAAG-3'
```

7. Preparation of Test Strips to be Used for Nucleic Acid Chromatography

Hi Flow Plus 180 Membrane Card (Millipore) which is a nitrocellulose membrane, equipped with Cellulose Fiber Sample Pad (Millipore) as the absorption pad was cut into strips having a width of approximately 5 mm. To a portion of the nitrocellulose (test line), 1 μL of a BSA-bound detection oligonucleotide at 1 mg/mL prepared as described above, was spotted and then air-dried. Thus, the detection oligonucleotide was immobilized via BSA, and a membrane (test strip) to be used for nucleic acid chromatography was prepared for each of the bacteria (FIG. 5-1).

8. Detection of Nucleic Acids by Nucleic Acid Chromatography

The membranes (test strips) for each of the bacteria prepared as described above were used for nucleic acid chromatography. The detection oligonucleotides prepared as described above were immobilized via BSA to the test line.

To 10 μL of a solution of PCR products from a genomic nucleic acid derived from each of the bacteria, which was prepared as described above by multiplex PCR, 1 μL of the oligonucleotides for masking (4 μM each) was added. 49 μL of development buffer (28.6% formamide, 1.43×SSC, 0.143% BSA, 1.43 mM EDTA, 0.143% dextran sulfate) for nucleic acid chromatography was added thereto. After treatment at 95° C. for five minutes, the mixture was rapidly cooled at 4° C. Subsequently, 10 μL of the capture oligonucleotide labeled with colloidal gold particles, which was produced as described above, was added to the solution, and the whole amount was added dropwise to the sample pad (FIG. 5-1) of the membrane (test strips).

9. Results

FIG. 9 shows the results of detection by agarose gel electrophoresis of multiplex PCR products obtained using the cdtC genes of *C. jejuni*, *C. coli*, and *C. fetus* as templates.

The results show that, the cdtC genes of interest from the three types of bacteria were each amplified by multiplex PCR.

On the other hand, amplified bands were not detected for related species, which are other bacteria belonging to the genus *Campylobacter* and *E. coli*.

When the PCR products of each of the bacteria were subjected to nucleic acid chromatography for *C. jejuni*, nucleic acid chromatography for *C. coli*, and nucleic acid chromatography for *C. fetus*, respectively, which were prepared as described above, each of the PCR products was clearly detected (FIG. 10).

Example 4

Effects of Mask Oligonucleotides on Nucleic Acid Chromatography

1. Preparation of Template DNAs for PCR

Template DNAs for PCR on EC were prepared by a method similar to that of Example 1.

2. Nucleic Acid Amplification by PCR

Takara LA Taq from TAKARA was used for the PCR. First, 0.2 μL of Takara LA Taq (5 U/μL), 2 μL of 10× LA PCR Buffer II ($Mg^{2+}$ free), 2 μL of 25 mM $MgCl_2$, 1.6 μL of dNTP mixture (2.5 Mm each), 1 μL of template DNA, and a pair of oligonucleotide primers (10 pmol/μL) at 0.4 μL each, were combined, and the volume was adjusted to 20 μL using sterilized water.

EC2F and EC2R shown below were used as PCR primers for EC.

```
EC2F:
                                      [SEQ ID NO: 87]
5'-CGCATTTTTATTAATGCTTTCG-3'

EC2R:
                                      [SEQ ID NO: 88]
5'-GGGCTGGCAGAGAGAGTG-3'
```

PCR was performed on Veriti 96 well Thermal Cycler (Applied Biosystems) under the following conditions: maintaining at 94° C. for three minutes; then repeating 40 cycles of reactions at 94° C. for 30 seconds, 60° C. for one minute, and 72° C. for one minute; and then maintaining at 72° C. for five minutes.

3. Preparation of a Capture Oligonucleotide Labeled with Colloidal Gold Particles The preparation was carried out by a method similar to that of Example 1.

The sequence of the capture oligonucleotide was the following.

```
For EC nucleic acid detection (ECB2):
                                      [SEQ ID NO: 89]
5'-TCGTGGGAACACAACCAGTC-3'
```

4. Preparation of a BSA-Bound Detection Oligonucleotide

The preparation was carried out by a method similar to that of Example 1.

The sequence of the detection oligonucleotide was the following.

```
For EC nucleic acid detection (ECA2):
                                      [SEQ ID NO: 90]
5'-GCCTGATAAACTTCCGCCTC-3'
```

5. Preparation of Mask Oligonucleotides

A pair of mask oligonucleotides (ECC3 and ECC4) that hybridize to the 5'-side and 3'-side regions, respectively, of the site on a bacteria-derived PCR product to which the detection oligonucleotide prepared as described above hybridizes, and which is positioned between the above regions, was prepared.

Furthermore, two control oligonucleotides (CT7 and CT8) having nucleic acid sequences which are not included in the nucleic acid sequences of PCR products amplified using a pair of oligonucleotide primers (EC2F and EC2R) for amplification of the EC gene produced as described above, were prepared for the control experiment.

The sequences of the prepared mask oligonucleotides for detection oligonucleotides were the following.

```
ECC3:
                                      [SEQ ID NO: 91]
5'-CAACCAGTTGATGATGGATC-3'

ECC4:
                                      [SEQ ID NO: 92]
5'-GCCACTCTCTCTGCCAGC-3'

CT7:
                                      [SEQ ID NO: 93]
5'-CGTGAAGATTTTCCATGACC-3'

CT8:
                                      [SEQ ID NO: 94]
5'-CATAAACCCGAGGAATAACG-3'
```

6. Preparation of Test Strips to be Used for Nucleic Acid Chromatography

The preparation was carried out by a method similar to that of Example 1.

7. Detection of Nucleic Acids by Nucleic Acid Chromatography

The test strips prepared for each of the bacteria as described above were used for nucleic acid chromatography (FIG. 5-1). The detection oligonucleotides prepared as described above were immobilized via BSA to the test line.

To 10 μL of the solution of PCR products from a genomic nucleic acid derived from each of the bacteria, which was prepared as described above, 1 μL of the oligonucleotides for masking (4 μM each) was added. Then, 90 μL of development buffer (20% formamide, 1×SSC, 0.1% BSA, 1 mM EDTA) for nucleic acid chromatography was added thereto. After treatment at 95° C. for five minutes, the mixture was rapidly cooled at 4° C. Subsequently, 10 μL of the capture oligonucleotide labeled with colloidal gold particles, which was produced as described above, was added to the solution, and the whole amount was added dropwise to the sample pad (FIG. 5-1) of the membrane (test strips).

As a control experiment, nucleic acid chromatography was performed without the use of the mask oligonucleotides.

8. Results

FIG. 11 shows the results of nucleic acid chromatography when the mask oligonucleotides were combined and then added.

Addition of only one type (ECC4) or two types (ECC3+ECC4) of mask oligonucleotides caused an increase in coloring sensitivity of nucleic acid chromatography.

Example 5

Examination of Optimal Mask Oligonucleotides for Nucleic Acid Chromatography

1. Preparation of Template DNAs for PCR

Template DNAs for PCR on SA, SE, and EF were prepared by a method similar to that of Example 1.

2. Nucleic Acid Amplification by PCR

PCR products for SA, SE, and EF were prepared by a method similar to that of Example 1.

3. Preparation of Capture Oligonucleotides Labeled with Colloidal Gold Particles The preparation was carried out by a method similar to that of Example 2.

The sequences of the capture oligonucleotides were the following.

```
For SA nucleic acid detection (SAB):
                                      [SEQ ID NO: 16]
5'-GGCTCATCTTCTAGTGGTGC-3'

For SE nucleic acid detection (SEB):
                                      [SEQ ID NO: 17]
5'-GGCCAAAAGTGAAGACATTG-3'

For EF nucleic acid detection (EFB):
                                      [SEQ ID NO: 19]
5'-ACAAATGGGGCTGGAGGTTC-3'
```

4. Preparation of BSA-Bound Detection Oligonucleotides

The preparation was carried out by a method similar to that of Example 3.

The sequences of the detection oligonucleotides were the following.

```
For SA nucleic acid detection (SAA):
                                        [SEQ ID NO: 23]
5'-GCCGTGCTCAATACAGCTCC-3'

For SE nucleic acid detection (SEA):
                                        [SEQ ID NO: 24]
5'-GGACATGATATGGGGGGCAT-3'

For EF nucleic acid detection (EFA):
                                        [SEQ ID NO: 26]
5'-AAGCAGGCTATCGGATTCTC-3'
```

5. Preparation of Mask Oligonucleotides

A pair of mask oligonucleotides that hybridize to the 5'-side and 3'-side regions, respectively, of the site on a bacteria-derived PCR product to which the capture oligonucleotide prepared as described above hybridizes, and which is positioned between the above regions, was prepared for each type of bacteria.

The sequences of the prepared mask oligonucleotides for the capture oligonucleotides were the following.

```
For SA nucleic acid detection (SAB1):
                                        [SEQ ID NO: 31]
5'-TAAAGCGTCGCTTAGAAATAATC-3'

For SA nucleic acid detection (SAB2):
                                        [SEQ ID NO: 32]
5'-TAAATCTTCAAGTATTCGTGTAGATG-3'

For SE nucleic acid detection (SEB1):
                                        [SEQ ID NO: 35]
5'-GTGATTACATTGACAATTGTTTC-3'

For SE nucleic acid detection (SEB2):
                                        [SEQ ID NO: 36]
5'-CAAATGGTTTCAACAAATTAATG-3'

For EF nucleic acid detection (EFB1):
                                        [SEQ ID NO: 43]
5'-AATCAATGGGGAAATTTTTTA-3'

For EF nucleic acid detection (EFB2):
                                        [SEQ ID NO: 44]
5'-TTTTAATGAGTCAAAGATTAGCGG-3'
```

Similarly, a pair of mask oligonucleotides that hybridize to the 5'-side and 3'-side regions, respectively, of the site on a bacteria-derived PCR product to which the detection oligonucleotides prepared as described above hybridize, and which is positioned between the above regions, was prepared for each type of bacteria.

The sequences of the prepared mask oligonucleotides for the detection oligonucleotides were the following.

```
For SA nucleic acid detection (SAA1):
                                        [SEQ ID NO: 29]
5'-CAGTAATATAATAGTCTTTATCTACACTTTCTAAT-3'

For SA nucleic acid detection (SAA2):
                                        [SEQ ID NO: 30]
5'-ACTTGTAGAGACACCCGTTAATACT-3'

For SE nucleic acid detection (SEA1):
                                        [SEQ ID NO: 33]
5'-TAAATATCGATTCTGCACATATTTTA-3'

For SE nucleic acid detection (SEA2):
                                        [SEQ ID NO: 34]
5'-CATTGCGAGTGAATTTACTG-3'

For EF nucleic acid detection (EFA1):
                                        [SEQ ID NO: 41]
5'-GAAGACAACGATTTATGTTTACGCTTTGGCA-3'

For EF nucleic acid detection (EFA2):
                                        [SEQ ID NO: 42]
5'-TATACGCCTTTTGAAACGGT-3'
```

6. Preparation of Test Strips to be Used for Nucleic Acid Chromatography

The preparation was carried out by a method similar to that of Example 3.

7. Detection of Nucleic Acids by Nucleic Acid Chromatography

The preparation was carried out by a method similar to that of Example 3.

8. Results

FIG. 12 shows the results of nucleic acid chromatography of PCR-amplified genomic DNA of each of the bacteria.

From the results, which of the mask oligonucleotides for capture oligonucleotides and the mask oligonucleotides for detection oligonucleotides are more effective depends on the sequence of the PCR product; however, highest coloring sensitivity was achieved for all bacteria when both mask oligonucleotides were added.

Example 6

Examination of Optimal Mask Oligonucleotides for Nucleic Acid Chromatography (Examination of Quantification of Target Nucleic Acids by Nucleic Acid Chromatography of the Present Invention and Examination of Conditions for Mask Oligonucleotides)

1. Preparation of Template DNA for PCR

Template DNA for SA was prepared by a method similar to that of Example 1.

2. Nucleic Acid Amplification by PCR

PCR products for SA were prepared by a method similar to that of Example 1.

3. Preparation of a Capture Oligonucleotide Labeled with Colloidal Gold Particles The preparation was carried out by a method similar to that of Example 2.

The sequence of the capture oligonucleotide was the following.

```
For SA nucleic acid detection (SAB):
                                        [SEQ ID NO: 16]
5'-GGCTCATCTTCTAGTGGTGC-3'
```

4. Preparation of a BSA-Bound Detection Oligonucleotide

The preparation was carried out by a method similar to that of Example 1.

The sequence of the detection oligonucleotide was the following.

```
For SA nucleic acid detection (SAA):
                                        [SEQ ID NO: 23]
5'-GCCGTGCTCAATACAGCTCC-3'
```

5. Preparation of Mask Oligonucleotides

Three pairs of mask oligonucleotides shown below that hybridize to the 5'-side and 3'-side regions, respectively, of the site on a bacteria-derived PCR product to which the capture oligonucleotide prepared as described above hybridizes, and which is positioned between the above regions, were prepared.

The sequences of the mask oligonucleotides that are adjacent to the prepared capture oligonucleotide without even a single-nucleotide gap were the following.

```
SAB1:
                                       [SEQ ID NO: 31]
5'-TAAAGCGTCGCTTAGAAATAATC-3'

SAB2:
                                       [SEQ ID NO: 32]
5'-TAAATCTTCAAGTATTCGTGTAGATG-3'
```

The sequences of the mask oligonucleotides with a 5-mer gap from the prepared capture oligonucleotide were the following.

```
SAB3:
                                       [SEQ ID NO: 95]
5'-CTAAAGCGTCGCTTAGAAA-3'

SAB4:
                                       [SEQ ID NO: 96]
5'-CTTCAAGTATTCGTGTAGATGC-3'
```

The sequences of the mask oligonucleotides with a 10-mer gap from the prepared capture oligonucleotide were the following.

```
SAB5:
                                       [SEQ ID NO: 97]
5'-CGCTAAAGCGTCGCTT-3'

SAB6:
                                       [SEQ ID NO: 98]
5'-AGTATTCGTGTAGATGCAT-3'
```

Similarly, three pairs of mask oligonucleotides that hybridize to the 5'-side and 3'-side regions, respectively, of the site on a bacteria-derived PCR product to which the detection oligonucleotide prepared as described above hybridizes, and which is positioned between the above regions, were prepared for each of the bacteria.

The sequences of the mask oligonucleotides that are adjacent to the prepared detection oligonucleotide without even a single-nucleotide gap were the following.

```
SAA1:
                                       [SEQ ID NO: 29]
5'-CAGTAATATAATAGTCTTTATCTACACTTTCTAAT-3'

SAA2:
                                       [SEQ ID NO: 30]
5'-ACTTGTAGAGACACCCGTTAATACT-3'
```

The sequences of the mask oligonucleotides with a 5-mer gap from the prepared detection oligonucleotide were the following.

```
SAA3:
                                       [SEQ ID NO: 99]
5'-AAACAGTAATATAATAGTCTTTATCTACACTTT-3'

SAA4:
                                       [SEQ ID NO: 100]
5'-TAGAGACACCCGTTAATACTAAATG-3'
```

The sequences of the mask oligonucleotide with a 10-mer gap from the prepared detection oligonucleotide were the following.

```
SAA5:
                                       [SEQ ID NO: 101]
5'-TCTTCTAAAACAGTAATATAATAGTCTTTATCTAC-3'

SAA6:
                                       [SEQ ID NO: 102]
5'-ACACCCGTTAATACTAAATGATT-3'
```

6. Preparation of Test Strips to be Used for Nucleic Acid Chromatography

The preparation was carried out by a method similar to that of Example 1.

7. Detection of Nucleic Acids by Nucleic Acid Chromatography

The preparation was carried out by a method similar to that of Example 1.

Detection was carried out by measuring the coloring intensity using the C10066-10 Immunochromato-Reader (Hamamatsu Photonics). Under conditions in which adjacent mask oligonucleotides were added, a calibration curve was plotted where the PCR product concentration was taken on the X axis and the coloring intensity was taken on the Y axis. For comparison of coloring intensities, a defined concentration of PCR product was used, and the coloring intensities were measured by nucleic acid chromatography for the groups to which the mask oligonucleotides with the 5-mer or 10-mer gap were added, and for the group without mask oligonucleotides for a control experiment. Using the above-described calibration curve, the results were converted to the amounts of PCR products by addition of adjacent mask oligonucleotides. The coloring sensitivity was calculated from the amount of PCR product that corresponds to the coloring intensity at the time of addition of each mask oligonucleotide, by defining the amount of PCR product that corresponds to the coloring intensity in the control experiment as 1.

8. Results

FIG. 13 shows the calibration curve drawn when the adjacent mask oligonucleotides were added.

As shown in the figure, a concentration-dependent increase in coloring intensity was observed, and this suggested that quantification is possible.

Furthermore, a comparison of coloring intensities by addition of each of the mask oligonucleotides is shown in Table 2.

TABLE 2

Comparison of coloring intensities in nucleic acid chromatography when each of the mask oligonucleotides was added

| Mask oligonucleotides | Converted concentration | Coloring sensitivity (-fold) |
|---|---|---|
| None | 4.24 ± 1.20 | 1 |
| Adjacent (no gap) | 145 | 34.22 |
| 5-mer gap | 140.38 ± 179.58 | 33.13 |
| 10-mer gap | 28.28 ± 31.90 | 6.67 |

As shown in the Table, while the coloring intensity was the highest for the adjacent mask oligonucleotides, addition of the mask oligonucleotides with the 5-mer gap from the capture and detection oligonucleotides gave a similar coloring intensity. When adding the mask oligonucleotides with the 10-mer gap from the capture and detection oligonucleotides, although the coloring intensities decreased in comparison to when the adjacent mask oligonucleotides were added, the coloring intensities were higher than when no mask oligonucleotides were added.

Example 7

Examination of Optimal Mask Oligonucleotides for Nucleic Acid Chromatography (Examination of the Timing of Contact of Mask Oligonucleotides to a Target Nucleic Acid)

1. Preparation of Template DNAs for PCR

Template DNAs for SA and SE were prepared by a method similar to that of Example 1.

2. Nucleic Acid Amplification by PCR

PCR products for SA and SE were prepared by a method similar to that of Example 1.

3. Preparation of Capture Oligonucleotides Labeled with Colloidal Gold Particles The preparation was carried out by a method similar to that of Example 2.

The sequences of the capture oligonucleotides were the following.

```
For SA nucleic acid detection (SAB):
                                   [SEQ ID NO: 16]
5'-GGCTCATCTTCTAGTGGTGC-3'

For SE nucleic acid detection (SEB):
                                   [SEQ ID NO: 17]
5'-GGCCAAAAGTGAAGACATTG-3'
```

4. Preparation of BSA-Bound Detection Oligonucleotides

The preparation was carried out by a method similar to that of Example 3.

The sequences of the detection oligonucleotides were the following.

```
For SA nucleic acid detection (SAA):
                                   [SEQ ID NO: 23]
5'-GCCGTGCTCAATACAGCTCC-3'

For SE nucleic acid detection (SEA):
                                   [SEQ ID NO: 24]
5'-GGACATGATATGGGGGGCAT-3'
```

5. Preparation of Conjugate Pads

Using 2 mM phosphate buffer (pH7.2) containing 5.0% sucrose, mask oligonucleotides were diluted to 4 µM. This solution was applied to a piece of glass fiber (Millipore) cut into the size of 10 mm×150 mm, and after drying, it was used as a conjugate pad. For a control, a conjugate pad was prepared by applying 2 mM phosphate buffer (pH7.2) containing 5.0% sucrose but without mask oligonucleotides, and then drying it.

The sequences of the prepared mask oligonucleotides were the following.

```
For SA nucleic acid detection (SAA1):
                                   [SEQ ID NO: 29]
5'-CAGTAATATAATAGTCTTTATCTACACTTTCTAAT-3'

For SA nucleic acid detection (SAA2):
                                   [SEQ ID NO: 30]
5'-ACTTGTAGAGACACCCGTTAATACT-3'

For SA nucleic acid detection (SAB1):
                                   [SEQ ID NO: 31]
5'-TAAAGCGTCGCTTAGAAATAATC-3'

For SA nucleic acid detection (SAB2):
                                   [SEQ ID NO: 32]
5'-TAAATCTTCAAGTATTCGTGTAGATG-3'

For SE nucleic acid detection (SEA1):
                                   [SEQ ID NO: 33]
5'-TAAATATCGATTCTGCACATATTTTA-3'

For SE nucleic acid detection (SEA2):
                                   [SEQ ID NO: 34]
5'-CATTGCGAGTGAATTTACTG-3'

For SE nucleic acid detection (SEB1):
                                   [SEQ ID NO: 35]
5'-GTGATTACATTGACAATTGTTTC-3'

For SE nucleic acid detection (SEB2):
                                   [SEQ ID NO: 36]
5'-CAAATGGTTTCAACAAATTAATG-3'
```

6. Preparation of Test Strips to be Used for Nucleic Acid Chromatography

The conjugate pad prepared as described above and Cellulose Fiber Sample Pad (Millipore) were pasted onto Hi Flow Plus 180 Membrane Card (Millipore) which is a nitrocellulose membrane, equipped with Cellulose Fiber Sample Pad (Millipore) as the absorption pad, and this was cut into strips having a width of approximately 5 mm. Membranes (test strips) for nucleic acid chromatography were produced by spotting 1 µL of 1 mg/mL BSA-bound detection oligonucleotide prepared as described above onto the strips, and then air-drying them to immobilize the detection oligonucleotide via BSA.

7. Detection of Nucleic Acids by Nucleic Acid Chromatography

To 10 µL of a solution of PCR products prepared as described above or TE, 1 µL of the oligonucleotides for masking at 4 µM or TE were added. 49 µL of development buffer (28.6% formamide, 1.43×SSC, 0.143% BSA, 1.43 mM EDTA) for nucleic acid chromatography was added thereto. After treatment at 95° C. for five minutes, the mixture was rapidly cooled at 4° C. Subsequently, 10 µL of the capture oligonucleotide labeled with colloidal gold particles, which was produced as described above, was added to the solution, and the whole amount was added dropwise to the sample pad of the membranes (test strips).

8. Results

As shown in FIG. 14, the effect of mask oligonucleotides was also exhibited and strong color development was observed in cases where a target PCR product and a colloidal-gold-labeled probe were applied and the mask oligonucleotides were reacted on the conjugate pad.

Example 8

Examination of Promoting Effects of Mask Oligonucleotides on Hybridization of an Oligonucleotide Probe to a Target Nucleic Acid by Hybridization-ELISA 1. Preparation of Template DNAs for PCR Genomic DNA containing the human β-globin gene was prepared from human blood using a QIAamp DNA Blood Midi Kit (QIAGEN).

Furthermore, by using the boiling method, template genomic DNA was prepared from *Escherichia coli* (hereinafter, denoted as EC).

More specifically, *Escherichia coli* (hereinafter, abbreviated as "EC"; bacterial strain JCM 1649) was cultured overnight in 3 mL of LB liquid medium (Becton Dickinson), then 50 µL of the test bacterial solution was added to 450 µL of a TE buffer [10 mM Tris-HCl (pH 8.0), 1 mM Ethylenediamine tetraacetic acid (EDTA)], and this was treated at 100° C. for ten minutes. After the treatment at 100° C., this was centrifuged at 12,000×g (MX-160, TOMY) for ten minutes, and the supernatant was collected, and the template DNA was obtained.

2. Nucleic Acid Amplification by PCR

First, for PCR on the human β-globin gene, 0.25 µL of Takara Taq (5 U/µL), 5 µL of 10×PCR Buffer ($Mg^{2+}$ plus), 4 µL of dNTP Mixture (2.5 mM each), 1 µL of template DNA, and the pair of oligonucleotide primers for amplification of the human β-globin gene indicated below (GM1F and GM1R; 10 pmol/µL each) at 5 µL each were combined, and the volume was adjusted to 50 µL using sterilized water.

The GM1R primer was labeled at the 5' end with fluorescein isothiocyanate (FITC).

```
GM1F:
                                      [SEQ ID NO: 103]
5'-GGTTGGCCAATCTACTCCCAGG-3'

GM1R:
                                      [SEQ ID NO: 104]
5'-FITC-TGGTCTCCTTAAACCTGTCTTG-3'
```

PCR was performed on Veriti Thermal Cycler (Applied Biosystems) under the following reaction conditions: maintaining at 94° C. for three minutes; then repeating 35 cycles of reactions at 94° C. for 30 seconds, 55° C. for one minute, and 72° C. for one minute; and then maintaining at 72° C. for five minutes.

Next, for PCR on the genomic DNA of EC, 0.5 µL of Takara LA Taq (5 U/µL), 5 µL of 10×LA PCR Buffer II ($Mg^{2+}$ free), 5 µL of 25 mM $MgCl_2$ solution, 4 µL of dNTP mixture (2.5 mM each), 1 µL of template DNA, and the pair of oligonucleotide primers for amplification of the EC genomic DNA shown below (EC2R and EC2F; 10 pmol/µL each) at 5 µL each were combined, and the volume was adjusted to 50 µL using sterilized water.

The EC2F primer was labeled at the 5' end with fluorescein isothiocyanate (FITC).

```
EC2F:
                                      [SEQ ID NO: 105]
5'-FITC-GTCAGGTAAGGCTAATTTCATTACCAGCAAAGG-3'

EC2R:
                                      [SEQ ID NO: 106]
5'-CGGTCAGCCATAGGGTAAATGACCAC-3'
```

PCR was performed on Veriti Thermal Cycler (Applied Biosystems) under the following reaction conditions: maintaining at 94° C. for three minutes; then repeating 40 cycles of reactions at 98° C. for 10 seconds, and 68° C. for one minute and 30 seconds; and then maintaining at 68° C. for five minutes.

3. Evaluation of PCR Products by Agarose Gel Electrophoresis

The amplified PCR products were purified using a QIAquick PCR Purification Kit (QIAGEN), and then separated by agarose gel electrophoresis with Mupid (Advance) using 2% agarose (Agarose I, AMRESCO) and 1×TAE buffer.

After electrophoresis, the gel was stained using an ethidium bromide solution at 1 µg/mL, and the stained DNA was photographed under ultraviolet light (260 nm) using a gel documentation analysis system ChemiDoc XRS (Bio-Rad Laboratories, Inc.).

4. Production of a Microplate to be Used for Hybridization-ELISA

A biotin-labeled capture oligonucleotide (GMA) that hybridizes to the nucleic acid of the human β-globin gene was prepared.

```
GMA:
                                      [SEQ ID NO: 107]
5'-Biotin-ATGGTGCACCTGACTCCTGA-3'
```

As schematically shown in FIG. 4-8, the biotin-labeled capture oligonucleotide (GMA) was added to a streptavidin-coated microplate (NUNC IMMOBILIZER STREPTAVIDIN F96, NUNC), and immobilized to the plate.

5. Preparation of Mask Oligonucleotides

A pair of mask oligonucleotides (GMA1 and GMA2) that hybridize to the 5'-side and 3'-side regions, respectively, of the site on the nucleic acid of the human f-globin gene to which the capture oligonucleotide (GMA) prepared as described above hybridizes, and which is positioned between the above regions, was prepared.

Furthermore, two control oligonucleotides (CT5 and CT6) having nucleic acid sequences which are not included in the nucleic acid sequences of the PCR products amplified by PCR using the pair of oligonucleotide primers (GM1F and GM1R) for amplification of the human β-globin gene prepared as described above, were prepared for the control experiment.

```
GMA1:
                                      [SEQ ID NO: 108]
5'-AGCAACCTCAAACAGACACC-3'

GMA2:
                                      [SEQ ID NO: 109]
5'-GGAGAAGTCTGCCGTTACTG-3'

CT5:
                                      [SEQ ID NO: 110]
5'-GGTCAGCCATAGGGTAAATGAC-3'

CT6:
                                      [SEQ ID NO: 111]
5'-TTATGATGTCAGAGGTCATGG-3'
```

6. Detection of Nucleic Acids by Hybridization-ELISA

First, to 2.5 µL (0.4 µM) of PCR products purified by a QIAquick PCR Purification Kit or TE buffer, 5 µM of the pair of mask oligonucleotides or 5 µM of the control oligonucleotides at 1 µL each was added, or 2 µL of TE buffer was added as a control. 10 µL of 125 mM NaOH was added thereto, and denaturation was carried out for five minutes.

Next, 100 µL of 50 mM phosphate buffer (pH7.0) was added and mixed, then the total amount was added to a microplate, and this was allowed to react at 37° C. for one hour. This was followed by washing three times with 300 µL of 2×SSCT (300 mM NaCl, 30 mM sodium citrate, 0.05% Tween20) warmed to 37° C., and adding 100 µL of HRP-labeled anti-FITC antibody (Rockland) diluted 50,000-fold with PBST (PBS containing 0.05% Tween20), and then reacting at room temperature for 30 minutes. After the reaction, washing with 300 µL of PBST was repeated three times, and 100 µL of TMB solution (KPL) was added, and this was reacted at room temperature for ten minutes. Then, the reaction was stopped using 100 µL of 1 M phosphoric acid, and the absorbance at 450 nm was measured using a plate reader 680XR (Bio-Rad).

7. Results

FIG. 15 shows the results of detecting each of the PCR products by agarose gel electrophoresis.

By PCR using the primers for amplifying the human β-globin gene, the 262-bp PCR product of interest was detected. Furthermore, by PCR using the primers for amplifying the EC genomic DNA, the 309-bp PCR product of interest was detected.

Detection results from hybridization-ELISA performed on each of the PCR products are shown below in Table 3.

While the absorbance of the PCR product of the human β-globin gene was 0.473±0.036 when no mask oligonucleotides were used, the absorbance was increased by approximately 1.5 times to 0.739±0.037 by addition of the mask oligonucleotides upon denaturation of the PCR product.

Furthermore, the values for the absorbance were low in both of the assay performed using only the mask oligonucleotides and the assay performed by adding the mask oligonucleotides to the PCR product of E. coli-derived genomic DNA instead of the PCR product of the human β-globin gene.

Furthermore, the absorbance in the assay performed by adding the control oligonucleotides (CT5 and CT6) which have nucleic acid sequences not included in the nucleic acid sequence of the PCR product of the human β-globin gene, showed a low value as with the absorbance in the assay performed without addition of the mask oligonucleotides.

As a result, the use of the mask oligonucleotides was found to increase the detection sensitivity for target nucleic acids in hybridization-ELISA.

TABLE 3

Effects of mask oligonucleotides in hybridization-ELISA

| PCR product[1] | β-glo | β-glo | β-glo | EC | None |
|---|---|---|---|---|---|
| Added oligo | None | GMA1 & GMA2 | CT5 & CT6 | GMA1 & GMA2 | GMA1 & GMA2 |
| OD 450 nm (Mean ± SD) | 0.473 ± 0.036 | 0.739 ± 0.037 | 0.508 ± 0.011 | 0.104 ± 0.010 | 0.110 ± 0.021 |

[1]β-glo: human β-globin-derived PCR product; EC: E. coli-derived PCR product

Example 9

Detection of PCR Products by Nucleic Acid Chromatography Using Mask Oligonucleotides that Target the 16S Subunit of the rRNA Genes of Various Bacteria 1. Preparation of Template DNAs for PCR Template DNAs for PCR for various bacteria were prepared by a method similar to that of Example 1 by producing bacterial sediments. Furthermore, for negative control experiments, template DNAs for PCR were prepared in a similar manner for various fungi.

The microbial strains used are indicated below with the culturing methods.

(1) Culturing in BHI liquid medium under ordinary atmosphere at 37° C.

Staphylococcus aureus (bacterial strain ATCC 12600);
Staphylococcus epidermidis (bacterial strain ATCC 14990);
Pseudomonas aeruginosa (bacterial strain ATCC 10145);
Enterococcus faecalis (bacterial strain ATCC 19433);
Escherichia coli (bacterial strain ATCC 11775);
Enterobacter cloacae (bacterial strain JCM 1232);
Klebsiella pneumoniae (bacterial strain JCM 1662);
Burkholderia cepacia (bacterial strain JCM 5507);
Stenotrophomonas maltophilia (bacterial strain JCM 1975);
Acinetobacter baumannii (bacterial strain ATCC 17978);
Pseudomonas fluorescens (bacterial strain JCM 5963);
Pseudomonas putida (bacterial strain JCM 6157);
Pseudomonas stutzeri (bacterial strain JCM 5965);
Citrobacter freundii (bacterial strain JCM 1657);
Citrobacter koseri (bacterial strain JCM 1659);
Edwardsiella tarda (bacterial strain JCM 1656);
Enterobacter aerogenes (bacterial strain JCM 1235);
Enterobacter amnigenus (bacterial strain JCM 1237);
Hafnia alvei (bacterial strain JCM 1666);
Klebsiella oxytoca (bacterial strain JCM 1665);
Kluyvera intermedia (bacterial strain JCM 1238);
Morganella morganii (bacterial strain JCM 1672);
Pantoea agglomerans (bacterial strain JCM 1236);
Proteus mirabilis (bacterial strain JCM 1669);
Proteus vulgaris (bacterial strain JCM 20339);
Providencia rettgeri (bacterial strain JCM 1675);
Serratia liquefaciens (bacterial strain JCM 1245);
Serratia marcescens (bacterial strain ATCC 274);
Staphylococcus haemolyticus (bacterial strain JCM 2416);
Staphylococcus hominis (bacterial strain ATCC 27844);
Staphylococcus saprophyticus (bacterial strain JCM 2427);
Enterococcus avium (bacterial strain JCM 8722);
Enterococcus durans (bacterial strain IFO 13131);
Enterococcus faecium (bacterial strain JCM 5804);
Corynebacterium diphtheriae (bacterial strain JCM 1310); and
Micrococcus luteus (bacterial strain JCM 1464).

(2) Culturing in BHI liquid medium under ordinary atmosphere at 30° C.

Sphingobacterium multivorum (bacterial strain IFO 14947);
Brevundimonas diminuta (bacterial strain IFO 14213);
Achromobacter xylosoxidans (bacterial strain IFO 15126);
Alcaligenes faecalis (bacterial strain JCM 20522);
Chromobacterium violaceum (bacterial strain IFO 12614);
Acinetobacter calcoaceticus (bacterial strain JCM 6842);
Vibrio vulnificus (bacterial strain JCM 3725);
Aeromonas hydrophila (bacterial strain JCM 1027);
Aeromonas sobria (bacterial strain JCM 2139);
Salmonella enterica (bacterial strain IFO 3313);
Bacillus cereus (bacterial strain IFO 15305); and
Bacillus subtilis (bacterial strain JCM 1465).

(3) Culturing on BHI agar medium under anaerobic conditions at 37° C.

Bacteroides fragilis (bacterial strain JCM 11019);
Bacteroides thetaiotaomicron (bacterial strain JCM 5827);
Bacteroides vulgatus (bacterial strain JCM 5826);
Porphyromonas asaccharolytica (bacterial strain JCM 6326);
Porphyromonas gingivalis (bacterial strain JCM 8525);
Prevotella intermedia (bacterial strain JCM 12248);
Fusobacterium necrophorum subspfunduhliforme (bacterial strain JCM 3724);
Lactobacillus acidophilus (bacterial strain JCM 1132);
Lactobacillus fermentum (bacterial strain JCM 1173);
Clostridium dificile (bacterial strain JCM 1296);
Clostridium perfringens (bacterial strain JCM 1290);
Peptoniphilus asaccharolyticus (bacterial strain JCM 1765);

*Eggerthella lenta* (bacterial strain JCM 9979); and
*Propionibacterium acnes* (bacterial strain JCM 6425).
(4) Culturing on blood agar medium under 5% $CO_2$ at 37° C.
*Capnocytophaga canimorsus* (bacterial strain ATCC 35979);
*Streptococcus agalactiae* (bacterial strain JCM 5671);
*Streptococcus pneumoniae* (bacterial strain ATCC 33400);
*Streptococcus pyogenes* (bacterial strain JCM 5674); and
*Streptococcus sanguinis* (bacterial strain JCM 5708).
(5) Culturing on chocolate agar medium under 5% $CO_2$ at 37° C.
*Neisseria lactamica* (bacterial strain ATCC 23970);
*Neisseria meningitidis* (bacterial strain ATCC 13077); and
*Haemophilus influenzae* (bacterial strain ATCC 33391).
(6) Culturing on BCYE agar medium under 5% $CO_2$ at 37° C.
*Legionella pneumophila* (bacterial strain JCM 7571)
(7) Culturing on blood agar medium under microaerophilic conditions at 37° C.
*Campylobacter jejuni* (bacterial strain ATCC700819)
(8) Culturing on blood agar medium under ordinary atmosphere at 37° C.
*Corynebacterium jeikeium* (bacterial strain JCM 9384)
(9) Culturing on BHI agar medium under 5% $CO_2$ at 37° C.
*Gardnerella vaginalis* (bacterial strain JCM 11026)
(10) Culturing in YPD liquid medium under ordinary atmosphere at 30° C. (fungi for use in negative control experiments)
*Candida albicans* (microbial strain IFO 1385);
*Candida glabrata* (microbial strain NBRC 0622);
*Candida krusei* (microbial strain IFO 1395);
*Candida parapsilosis* (microbial strain IFO 1396);
*Candida tropicalis* (microbial strain IFO 1400);
*Aspergillus fumigatus* (microbial strain TIMM 0063); and
*Cryptococcus neoformans* (microbial strain TIMM 0354).
(11) Culturing on BHI agar medium under ordinary atmosphere at 30° C. (fungi for use in negative control experiments)
*Tichosporon cutaneum* (microbial strain JCM 1462)

2. Nucleic Acid Amplification by PCR

PrimeSTAR HS DNA Polymerase from TAKARA was used for PCR. First, 0.2 µL of PrimeSTAR HS DNA Polymerase (2.5 U/µL), 4 µL of 5× PrimeSTAR Buffer ($Mg^{2+}$ plus), 1.6 µL of dNTP mixture (2.5 mM each), 0.1 ng of template DNA, and a pair of oligonucleotide primers (10 pmol/µL) at 0.4 µL each were combined, and the volume was adjusted to 20 µL using sterilized water.

The following PCR primers were prepared and used.

```
16S-10F:
                                 [SEQ ID NO: 112]
5'-GTTTGATCCTGGCTCA-3'

16S-800R:
                                 [SEQ ID NO: 113]
5'-TACCAGGGTATCTAATCC-3'
```

PCR reactions were carried out according to "Rapid Identification of Microorganisms Using Genetic Analyses" (Japanese Pharmacopeia reference information).

PCR was performed on Veriti Thermal Cycler (Applied Biosystems) under the following reaction conditions: maintaining at 94° C. for one minute; then repeating 30 cycles of reactions at 94° C. for 30 seconds, 55° C. for one minute, and 72° C. for one minute; and then maintaining at 72° C. for five minutes.

3. Evaluation of PCR Products by Agarose Gel Electrophoresis

The evaluation was carried out by a method similar to that of Example 1.

4. Preparation of a Capture Oligonucleotide Labeled with Colloidal Gold Particles The preparation was carried out by a method similar to that of Example 2.

The sequence of the prepared capture oligonucleotide was the following.

```
For 16S rDNA detection:
                                 [SEQ ID NO: 114]
5'-GCAGCAGTAGGGAATCTTCG-3'
```

5. Preparation of a BSA-Bound Detection Oligonucleotide

The preparation was carried out by a method similar to that of Example 3.

The sequence of the detection oligonucleotide to be bound to BSA was the following.

```
For 16S rDNA detection:
                                 [SEQ ID NO: 115]
5'-CACACTGGAACTGAGACACG-3'
```

6. Preparation of Test Strips to be Used for Nucleic Acid Chromatography

The preparation was carried out by a method similar to that of Example 3.

As described above, the BSA-bound detection oligonucleotide was immobilized onto a membrane, and this was cut into strips having a width of 5 mm to produce test strips to be used for nucleic acid chromatography (FIG. 5-1).

7. Preparation of Mask Oligonucleotides

A pair of mask oligonucleotides that hybridize to the 5'-side and 3'-side regions, respectively, of the site on a bacterial genomic nucleic acid to which the capture oligonucleotide prepared as described above hybridizes, and which is positioned between the above regions, was prepared.

Similarly, a pair of mask oligonucleotides that hybridize to the 5'-side and 3'-side regions, respectively, of the site on a bacterial genomic nucleic acid to which the detection oligonucleotide prepared as described above hybridizes, and which is positioned between the above regions, was prepared.

The sequences of the prepared mask oligonucleotides were the following.

Mask oligonucleotide (M1') for detection oligonucleotide

```
For 16S rDNA detection:
                                 [SEQ ID NO: 116]
5'-TGGTCTGAGAGGATGATCAGT-3'
```

Mask oligonucleotide (M2' and M3') for detection oligonucleotide and for capture oligonucleotide

```
For 16S rDNA detection:
                                 [SEQ ID NO: 117]
5'-GTCCAGACTCCTACGGGAG-3'
```

Mask oligonucleotide (M4') for capture oligonucleotide

```
For 16S rDNA detection:
                                [SEQ ID NO: 118]
5'-ACAATGGGCGAAAGCCT-3'
```

8. Detection of Nucleic Acids by Nucleic Acid Chromatography

The test strips prepared for each of the bacteria and fungi as described above were used for nucleic acid chromatography. The detection oligonucleotides prepared as described above were immobilized via BSA to the test line.

To 1.25 µL of a solution of PCR products from a genomic nucleic acid derived from each of the bacteria and fungi, which were prepared as described above, 1 µL of the oligonucleotides for masking (4 µM each) was added. 30 µL of development buffer (24% formamide, 1×SSC, 0.1% BSA, 1 mM EDTA, 0.5 M guanidine hydrochloride) for nucleic acid chromatography was added thereto, and the total amount was adjusted to 70 µL by adding TE. After treatment at 95° C. for five minutes, the mixture was rapidly cooled at 4° C. Subsequently, 5 µL of the capture oligonucleotide labeled with colloidal gold particles, which was produced as described above, was added to the solution. Test strips were soaked in this solution, and nucleic acid chromatography was performed.

9. Results

Table 4 and FIG. 16 (some of the various microbial species shown in Table 4) show the results of detection of PCR products obtained using the genomic DNAs of each of the bacteria and fungi as templates, by nucleic acid chromatography.

As a result, target nucleic acids to be detected (16S subunit of the rRNA gene) were detected with high sensitivity for all of the bacteria examined by nucleic acid chromatography using the mask oligonucleotides. On the other hand, the experiment results for all of the fungi, which were examined for negative control experiments, were negative.

TABLE 4

Detection of bacteria by nucleic acid chromotography based on 16S rRNA

| Strain name | Strain number | Nucleic acid chromatography | Strain name | Strain number | Nucleic acid chromatography |
| --- | --- | --- | --- | --- | --- |
| *Staphylococcus aureus* | ATCC 12600 | + | *Pantoea agglomerans* | JCM 1236 | + |
| *Staphylococcus epidermidis* | ATCC 14990 | + | *Proteus mirabilis* | JCM 1669 | + |
| *Pseudomonas aeruginosa* | ATCC 10145 | + | *Proteus vulgaris* | JCM 20339 | + |
| *Enterococcus faecalis* | ATCC 19433 | + | *Providencia reugeri* | JCM 1675 | + |
| *Escherichia coli* | ATCC 11775 | + | *Salmonella enterica* | IFO 3313 | + |
| *Enterobacter cloacae* | JCM 1232 | + | *Serratia liquefaciens* | JCM 1245 | + |
| *Klebsiella pneumoniae* | JCM 1662 | + | *Serratia marcesens* | ATCC 274 | + |
| *Campylobacter jejuni* | ATCC700819 | + | *Haemophilus influenzae* | ATCC 33391 | + |
| *Bacteroides fragilis* | JCM 11019 | + | *Fusobacterium necrophorum* subsp *finduliforms* | JCM 3724 | + |
| *Bacteroides thetalotaomicron* | JCM 5827 | + | | | |
| *Bacteroides vulgatus* | JCM 5826 | + | *Bacillus cereus* | IFO 15305 | + |
| *Porphyromonas asaccharolytica* | JCM 6326 | + | *Bacillus subtilis* | JCM 1465 | + |
| *Porphyromonas gingivalis* | JCM 8525 | + | *Staphylococcus haemolyticus* | JCM 2416 | + |
| *Prevotella intermedia* | JCM 12248 | + | *Staphylococcus hominis* | ATCC 27844 | + |
| *Capnocytophaga canimorsus* | ATCC 35979 | + | *Staphylococcus saprophyticus* | JCM 2427 | + |
| *Sphingobacterium multivorum* | IFO 14947 | + | *Enterococcus avium* | JCM 8722 | + |
| *Brevimdimonas diminata* | IFO 14213 | + | *Enterococcus durans* | IFO 13131 | + |
| *Achromobacter xylosoxidans* | IFO 15126 | + | *Enterococcus faecium* | JCM 5804 | + |
| *Alcaligenes faecalis* | JCM 20522 | + | *Lactobacillus acidophilus* | JCM 1132 | + |
| *Burkholderio cepocia* | JCM 5507 | + | *Lactobacillus fermentum* | JCM 1173 | + |
| *Chromobacterium violaceum* | IFO 12614 | + | *Streptococcus agaluctiae* | JCM 5671 | + |
| *Neisseria lactumica* | ATCC 23970 | + | *Streptococcus pneumoniae* | ATCC 33400 | + |
| *Neisseria meningitidis* | ATCC 13077 | + | *Streptococcus pyogenes* | JCM 5674 | + |
| *Stenotrophomonos maltophilia* | JCM 1975 | + | *Streptococcus sanguinis* | JCM 5708 | + |
| *Legionello pneumophila* | JCM 7571 | + | *Clostridium difficile* | JCM 1296 | + |
| *Acinetobacter baumannii* | ATCC 17978 | + | *Clostridium perfringens* | JCM 1290 | + |
| *Acinetobacter calcoaceticus* | JCM 6842 | + | *Peptoniphilus asaccharolyticus* | JCM 1765 | + |
| *Pseudomonas fluorescens* | JCM 5963 | + | *Eggerthella lenta* | JCM 9979 | + |
| *Pseudomonas putida* | JCM 6157 | + | *Corynebacterium diphtheriae* | JCM 1310 | + |
| *Pseudomonas stutzeri* | JCM 5965 | + | *Corynebacterium jeikeium* | JCM 9384 | + |
| *Vibrio vulnificus* | JCM 3725 | + | *Micrococcus lutens* | JCM 1464 | + |
| *Aeromonas hydrophila* | JCM 1027 | + | *Propionibacterium acnes* | JCM 6425 | + |
| *Aeromonas sobria* | JCM 2139 | + | *Gardnerella vaginalis* | JCM 11026 | + |
| *Citrobacter freundii* | JCM 1657 | + | *Candida albicans* | IFO 1385 | − |
| *Citrobacter koseri* | JCM 1659 | + | *Candida glabrata* | NBRC 0622 | − |
| *Edwardsiella tarda* | JCM 1656 | + | *Candida krusei* | IFO 1395 | − |
| *Enterobacter aerogenes* | JCM 1235 | + | *Candida parapsilosis* | IFO 1396 | − |
| *Enterobacter amnigenus* | JCM 1237 | + | *Candida tropicalis* | IFO 1400 | − |
| *Hafnia alvei* | JCM 1666 | + | *Aspergillus fumigatus* | TIMM 0063 | − |
| *Klebsiella oxytoca* | JCM 1665 | + | *Cryptococcus neoformans* | TIMM 0354 | − |
| *Kluyvera intermedia* | JCM 1238 | + | *Trichosporon cutaneum* | JCM 1462 | − |
| *Morganella marganii* | JCM 1672 | + | | | |

Example 10

Detection of PCR Products from Genomic DNAS of Various Fungi by Nucleic Acid Chromatography Using Mask Oligonucleotides 1. Preparation of Template DNAs for PCR Template DNAs for PCR were prepared as genomic DNAs using ZR Fungal/Bacterial DNA MiniPrep (ZYMO RESARCH).

More specifically, each of the following fungi was individually cultured in 3 mL of YPD liquid medium (Q-Biogene) at 30° C. overnight. 1 mL of the obtained test fungal solution was centrifuged at 6,000×g for three minutes, and then the residue was suspended in 500 µL of PBS. Subsequently, the suspension was centrifuged at 6,000×g for three minutes, and then the residue was collected:

*Candida albicans* (abbreviated as "CA", bacterial strain NBRC1385);

*Candida glabrata* (abbreviated as "CG", bacterial strain NBRC0005);

*Candida krusei* (abbreviated as "CK", bacterial strain NBRC0011);

*Candida parapsilosis* (abbreviated as "CP", bacterial strain NBRC1396);

*Candida tropicalis* (abbreviated as "CT", bacterial strain NBRC1400);

*Candida guilliermondii* (abbreviated as "CGu", bacterial strain NBRC0566);

*Candida kefyr* (abbreviated as "CKf", bacterial strain NBRC0586);

*Candida lusitaniae* (abbreviated as "CL", bacterial strain ATCC66035); and

*Candida metapsilosis* (abbreviated as "CM", bacterial strain NBRC0640).

Each sample was dissolved by addition of 300 µL of an enzyme reagent (1 mL of PBS containing 5 mg of Zymolyase 20T (SEIKAGAKU)), and reaction was allowed to take place at 37° C. for one hour.

450 µL of lysis buffer was added and mixed, then the mixture was transferred to a ZR BashingBead Lysis Tube. This was mixed for five minutes by vortexing, and centrifuged at 10,000×g for one minute at 4° C. 400 µL of the supernatant was transferred to a Zymo Spin IV spin filter, and then centrifuged at 7,000×g for one minute.

1200 µL of Fungal/Bacterial DNA Binding Buffer was added to the filtrate, and this was mixed. 800 µL of the mixed solution was transferred to a Zymospin IIC Column, and this was centrifuged at 10,000×g for one minute. 800 µL of the remaining mixed solution was transferred to a Zymospin IIC Column and this was centrifuged at 10,000×g for one minute. The Zymospin IIC Column was transferred to a new Collection tube, 200 µL of DNA Pre wash Buffer was added thereto, and this was centrifuged at 10,000×g for one minute. 500 µL of Fungal/Bacterial DNA wash Buffer was added thereto, and this was centrifuged at 10,000×g for one minute. The Zymospin IIC Column was transferred to a new Eppendorf tube, and 80 µL of DNA Elution Buffer was added thereto, and the mixture was allowed to stand for one minute. This was then centrifuged at 10,000×g for 30 seconds, and the filtrate was used as the template DNA.

2. Nucleic Acid Amplification by PCR

PrimeSTAR HS DNA Polymerase from TAKARA was used for PCR. First, 0.2 µL of PrimeSTAR HS DNA Polymerase (2.5 U/µL), 4 µL of 5× PrimeSTAR Buffer ($Mg^{2+}$ plus), 1.6 µL of dNTP mixture (2.5 mM each), 0.1 ng of template DNA, and of a pair of oligonucleotide primers (10 pmol/µL) at 0.4 µL each were combined, and the volume was adjusted to 20 µL using sterilized water.

The following PCR primers were prepared and used.

```
ITS1F:
                                [SEQ ID NO: 119]
    5'-GTAACAAGGT(T/C)TCCGT-3'

ITS1R:
                                [SEQ ID NO: 120]
    5'-CGTTCTTCATCGATG-3'
```

PCR reactions were carried out according to "Rapid Identification of Microorganisms Using Genetic Analyses" (Japanese Pharmacopeia reference information).

PCR was performed on Veriti Thermal Cycler (Applied Biosystems) under the following reaction conditions: maintaining at 94° C. for one minute; then repeating 30 cycles of reactions at 94° C. for 30 seconds, 55° C. for one minute, and 72° C. for one minute; and then maintaining at 72° C. for five minutes.

3. Evaluation of PCR Products by Agarose Gel Electrophoresis

The evaluation was carried out by a method similar to that of Example 1.

4. Preparation of a Capture Oligonucleotide Labeled with Colloidal Gold Particles The preparation was carried out by a method similar to that of Example 2.

The sequence of the prepared capture oligonucleotide was the following.

```
For ITS1 detection:
                                [SEQ ID NO: 121]
    5'-AGGTGAACCTGCGGAAGGAT-3'
```

5. Preparation of a BSA-Bound Detection Oligonucleotides

The preparation was carried out by a method similar to that of Example 1.

The sequences of the prepared detection oligonucleotides to be bound to BSA were the following.

```
For CA nucleic acid detection:
                                [SEQ ID NO: 122]
    5'-TTGGCGGTGGGCCCAGCCTG-3'

For CG nucleic acid detection:
                                [SEQ ID NO: 123]
    5'-CACACGACTCGACACTTTCT-3'

For CK nucleic acid detection:
                                [SEQ ID NO: 124]
    5'-CTACACTGCGTGAGCGGAAC-3'

For CP nucleic acid detection:
                                [SEQ ID NO: 125]
    5'-TGGTAGGCCTTCTATATGGG-3'

For CT nucleic acid detection:
                                [SEQ ID NO: 126]
    5'-TCTTTGGTGGCGGGAGCAAT-3'
```

6. Preparation of Test Strips to be Used for Nucleic Acid Chromatography

The preparation was carried out by a method similar to that of Example 1.

The BSA-bound detection oligonucleotides prepared for each fungi as described above, were immobilized onto a membrane, and this was cut into strips having a width of 5 mm to produce test strips to be used for nucleic acid chromatography (FIG. 5-1).

7. Preparation of Mask Oligonucleotides

A pair of mask oligonucleotides that hybridize to the 5'-side and 3'-side regions, respectively, of the site on a fungal genomic nucleic acid to which the capture oligonucleotide prepared as described above hybridizes, and which is positioned between the above regions, was prepared for each of the fungi.

Similarly, a pair of mask oligonucleotides that hybridize to the 5'-side and 3'-side regions, respectively, of the site on a fungal genomic nucleic acid to which the detection oligonucleotide prepared as described above hybridizes, and which is positioned between the above regions, was prepared for each of the fungi.

The sequences of the prepared mask oligonucleotides were the following.

```
For CA nucleic acid detection:
                                      [SEQ ID NO: 119]
5'-GTAACAAGGT(T/C)TCCG-3'
(same as the sequence for the above-mentioned
oligonucleotide ITS1F)

For CA nucleic acid detection (CAA2):
                                      [SEQ ID NO: 127]
5'-CATTACTGATTTGCTTAATTGCAC-3'

For CA nucleic acid detection:
                                      [SEQ ID NO: 128]
5'-GTTTTTCTTTGAAACAAACTTGCT-3'

For CA nucleic acid detection:
                                      [SEQ ID NO: 129]
5'-CCGCCAGAGGTCTAAACTTAC-3'

For CG nucleic acid detection:
                                      [SEQ ID NO: 119]
5'-GTAACAAGGT(T/C)TCCG-3'
(same as the sequence for the above-mentioned
oligonucleotide ITS1F)

For CG nucleic acid detection:
                                      [SEQ ID NO: 127]
5'-CATTACTGATTTGCTTAATTGCAC-3'
(same as the sequence for the above-mentioned
oligonucleotide CAA2)

For CG nucleic acid detection:
                                      [SEQ ID NO: 130]
5'-TTCCAAAGGAGGTGTTTTAT-3'

For CG nucleic acid detection:
                                      [SEQ ID NO: 131]
5'-AATTACTACACACAGTGGAGTTTAC-3'

For CK nucleic acid detection:
                                      [SEQ ID NO: 119]
5'-GTAACAAGGT(T/C)TCCG-3'
(same as the sequence for the above-mentioned
oligonucleotide ITS1F)

For CK nucleic acid detection:
                                      [SEQ ID NO: 127]
5'-CATTACTGATTTGCTTAATTGCAC-3'
(same as the sequence for the above-mentioned
oligonucleotide CAA2)

For CK nucleic acid detection:
                                      [SEQ ID NO: 132]
5'-GAAAACAACAACACCTAAAATG-3'

For CP nucleic acid detection:
                                      [SEQ ID NO: 119]
5'-GTAACAAGGT(T/C)TCCG-3
(same as the sequence for the above-mentioned
oligonucleotide ITS1F)

For CP nucleic acid detection:
                                      [SEQ ID NO: 133]
5'-CATTACAGAATGAAAAGTGCTTAAC-3

For CP nucleic acid detection:
                                      [SEQ ID NO: 134]
5'-TCTTTTTTTGAAAACTTTGCTT-3'

For CP nucleic acid detection:
                                      [SEQ ID NO: 135]
5'-GCCTGCCAGAGATTAAACTC-3'

For CT nucleic acid detection:
                                      [SEQ ID NO: 119]
5'-GTAACAAGGT(T/C)TCCG-3
(same as the sequence for the above-mentioned
oligonucleotide ITS1F)

For CT nucleic acid detection:
                                      [SEQ ID NO: 127]
5'-CATTACTGATTTGCTTAATTGCAC-3'
(same as the sequence for the above-mentioned
oligonucleotide CAA2)

For CT nucleic acid detection:
                                      [SEQ ID NO: 136]
5'-CACATGTGTTTTTATTGAACAAATT-3'

For CT nucleic acid detection:
                                      [SEQ ID NO: 137]
5'-CCTACCGCCAGAGGTTATAA-3'
```

8. Detection of Nucleic Acids by Nucleic Acid Chromatography

The test strips prepared for each of the fungi as described above were used for nucleic acid chromatography. The detection oligonucleotides prepared as described above were immobilized via BSA to the test line.

To 1.25 µL of a solution of PCR products from a genomic nucleic acid derived from each of the fungi, which were prepared as described above, 1 µL of the oligonucleotides for masking (4 µM each) were added. 30 µL of development buffer (20% formamide, 1×SSC, 0.1% BSA, 1 mM EDTA, 0.5 M guanidine hydrochloride) for nucleic acid chromatography was added thereto, and the total amount was adjusted to 65 µL by adding TE. After treatment at 95° C. for five minutes, the mixture was rapidly cooled at 4° C. Subsequently, 5 µL of the capture oligonucleotide labeled with colloidal gold particles, which was produced as described above, was added to the solution. Test strips were soaked in this solution, and nucleic acid chromatography was performed.

9. Results

Results of detection by agarose gel electrophoresis and nucleic acid chromatography on PCR products obtained using the genomic DNA from each of the fungi as a template are shown in FIGS. 17 and 18, respectively.

The results showed that, for all of the fungi, the genomic DNAs of interest were amplified by PCR, and the PCR products (target nucleic acids) can be detected specifically with high sensitivity by nucleic acid chromatography using the mask oligonucleotides.

INDUSTRIAL APPLICABILITY

The methods of the present invention for detecting and quantifying nucleic acids by nucleic acid chromatography using mask oligonucleotides, and devices and kits to be used in such methods can detect and quantify an arbitrary nucleic acid (for example, a naturally-occurring nucleic acid, genomic DNA, cDNA, RNA, and a nucleic acid amplified by PCR and such) derived from various organisms including eukaryotes, prokaryotes, viruses, bacteria, and microorganisms simply and with high sensitivity As a result, the use of the methods, devices, and/or kits of the present invention enables simple, quick, and highly precise identification of the presence/absence and degree of bacterial or viral infection of mammals including humans, host organisms, plants, food or drinks, and such; the causes of various diseases suspected to be caused by viral or bacterial infection or genetic mutations (such as infectious diseases, cancer, metabolic diseases, and genetic diseases); and various genetic characteristics due to genetic diversity.

The invention claimed is:

1. A chromatography method for simultaneously detecting two or more different nucleic acids N in a sample, said method is performed in the presence of a lateral flow chromatography device, the device comprises:
 (i) an application zone in contact with an enclosing zone, wherein an oligonucleotide R1' labeled with a label L1 is enclosed on the enclosing zone and is capable of hybridizing to each of two or more different target nucleic acids N;
 (ii) the enclosing zone in contact with both the application zone and a development element;
 (iii) the development element which comprises two or more detection zones for capturing and then detecting nucleic acid hybrids, wherein each of the two or more detection zones is placed at different positions in the development element, wherein each of the detection zones comprise a different one of immobilized oligonucleotides R2' which only specifically hybridizes to one of the two or more different target nucleic acids N; and
 (iv) an absorption zone in contact with the development element to absorb a solution that moves through the lateral flow chromatography device by capillary action,
 wherein the method comprises the steps of:
 a) applying a solution comprising the two or more different target nucleic acids N and a set of at least one of oligonucleotides M1', M2', M3', and M4' to the application zone, wherein at least one of the oligonucleotides M1', M2', M3', and M4' hybridizes to at least one of regions M1, M2, M3, and M4 of each of the different target nucleic acids N and yield different hybridized nucleic acids I, wherein each of the regions M1, M2, M3, and M4 is in a single-stranded region of each of the different target nucleic acids N, and each of the different target nucleic acids N comprises a region R1 that is positioned between the regions M1 and M2, and a region R2 that is different from the region R1 and positioned between the regions M3 and M4;
b) by capillary action in the lateral flow chromatography device, moving the different hybridized nucleic acids I of step a) through the application zone to the enclosing zone, wherein the oligonucleotides R1' labeled with a label L1 on the enclosing zone hybridizes to each of the different hybridized nucleic acids I of step a) and yield different labeled hybridized nucleic acids II;
c) by capillary action in the lateral flow chromatography device, moving the different labeled hybridized nucleic acids II of step b) through the enclosing zone to the two or more detection zones, wherein each of the different labeled hybridized nucleic acids II of step b) specifically hybridizes to a different one of the immobilized oligonucleotides R2' on one of the two or more detection zones; and
d) detecting the labeled hybridized nucleic acids II of step c) on each of the detection zones, thereby simultaneously detect the two or more different nucleic acids N in the sample based on a color generated from the label L1 in each of the detection zones and the position of each of the detection zones in the development element.

2. A chromatography method for simultaneously detecting two or more different nucleic acids N in a sample, said method is performed in the presence of a lateral flow chromatography device, the device comprises:
(i) an application zone in contact with an enclosing zone, wherein an oligonucleotide R1' labeled with a label L1 is enclosed on the enclosing zone and is capable of hybridizing to each of two or more different target nucleic acids N;
(ii) the enclosing zone in contact with both the application zone and a development element;
(iii) the development element which comprises two or more detection zones for capturing and then detecting nucleic acid hybrids, wherein each of the two or more detection zones is placed at different positions in the development element, wherein each of the detection zones comprise a different one of immobilized oligonucleotides R2' which only specifically hybridizes to one of the two or more different target nucleic acids N; and
(iv) an absorption zone in contact with the development element to absorb a solution that moves through the lateral flow chromatography device by capillary action, wherein the method comprises the steps of:
a) applying a solution comprising the two or more different target nucleic acids N and a set of oligonucleotides M1', M2', M3', and M4' to the application zone, wherein the oligonucleotides M1', M2', M3', and M4' hybridize to regions M1, M2, M3, and M4 of each of the different target nucleic acids N and yield different hybridized nucleic acids I, wherein each of the regions M1, M2, M3, and M4 is in a single-stranded region of each of the different target nucleic acids N, and each of the different target nucleic acids N comprises a region R1 that is positioned between the regions M1 and M2, and a region R2 that is different from the region R1 and positioned between the regions M3 and M4;
b) capillary action in the lateral flow chromatography device, moving the different hybridized nucleic acids I of step a) through the application zone to the enclosing zone, wherein the oligonucleotides R1' labeled with a label L1 on enclosing zone hybridizes to each of the different hybridized nucleic acids I of step a) and yield different labeled hybridized nucleic acids II;
c) by capillary action in the lateral flow chromatography device, moving the different labeled hybridized nucleic acids II of step b) through the enclosing zone to the two or more detection zones, wherein each of the different labeled hybridized nucleic acids II of step b) specifically hybridizes to a different one of the immobilized oligonucleotides R2' on one of the two or more detection zones; and
d) detecting the labeled hybridized nucleic acids II of step c) on each of the detection zones, thereby simultaneously detect the two or more different nucleic acids N in the sample based on a color generated from the label L1 in each of the detection zones and the position of each of the detection zones in the development element.

3. The method of claim 1, wherein the at least one of the oligonucleotides M1', M2', M3', and M4' hybridizes to at least one of regions M1, M2, M3, and M4 in step a) comprises one of the following:
(i) hybridization of at least one of the oligonucleotides M1' and M2' to at least one of the regions M1 and M2;
(ii) hybridization of at least one of the oligonucleotides M3' and M4' to at least one of the regions M3 and M4;
(iii) hybridization of at least one of the oligonucleotides M1' and M2' to at least one of the regions M1 and M2, and hybridization of at least one of the oligonucleotides M3' and M4' to at least one of the regions M3 and M4;
(iv) hybridization of the oligonucleotides M1' and M2' to both the regions M1 and M2, respectively;
(v) hybridization of the oligonucleotides M3' and M4' to both the regions M3 and M4, respectively;
(vi) hybridization of the oligonucleotides M1' and M3' to both the regions M1 and M3, respectively;
(vii) hybridization of the oligonucleotides M1' and M4' to both the regions M1 and M4, respectively;
(viii) hybridization of the oligonucleotides M2' and M3' to both the regions M2 and M3, respectively;
(ix) hybridization of the oligonucleotides M2' and M4' to both the regions M2 and M4, respectively; or
(x) hybridization of the oligonucleotides M1' and M2' to both the regions M1 and M2, respectively, and hybridization of the oligonucleotides M3' and M4' to both the regions M3 and M4, respectively.

4. The method of claim 1 or 2, wherein the label L1 is a colloidal metal particle or a colored latex particle.

5. The method of claim 4, wherein the colloidal metal particle is a colloidal gold particle, a colloidal platinum particle, a colloidal platinum-gold particle, a palladium particle, a colloidal silver particle, a colloidal rhodium particle, a colloidal ruthenium particle, or a colloidal iridium particle.

6. The method of claim 1 or 2, wherein the device is in a case made of a moisture-impermeable solid material.

7. The method of claim 1 or 2, wherein each of the different target nucleic acids N is produced by denaturing double-stranded nucleic acids.

8. The method of claim 1 or 2, wherein each of the different target nucleic acids N is a DNA or an RNA.

9. The method of claim 1 or 2, wherein each of the different target nucleic acids N is a nucleic acid derived from a genome of an eukaryote, a prokaryote, a bacterium, or a virus; or a nucleic acid derived from a genome fragment produced by cleavage of a genome with a restriction enzyme; or an artificially amplified nucleic acid.

10. The method of claim 9, wherein each the different nucleic acids N derived from the genome of the bacterium is one of the following:
   a) a genomic nucleic acid of *Staphylococcus aureus*;
   b) a genomic nucleic acid of *Staphylococcus epidermis*;
   c) a genomic nucleic acid of *Pseudomonas aeruginosa*;
   d) a genomic nucleic acid of *Enterococcus faecalis*;
   e) a genomic nucleic acid of *Escherichia coil*;
   f) a genomic nucleic acid of *Enterobacter cloacae*; or
   g) a genomic nucleic acid of *Kiebsiella pneumoniae*.

11. The method of claim 1 or 2, wherein step b) or c) is performed in a buffer containing at least one denaturant or chaotropic agent, or containing at least one denaturant or chaotropic agent and at least one inorganic salt.

12. The method of clam 2, wherein the label L1 is a colloidal metal particle.

13. The method of claim 12, wherein the colloidal metal particle is a colloidal gold particle, a colloidal platinum particle, a colloidal platinum-gold particle, a palladium particle, a colloidal silver particle, a colloidal rhodium particle, a colloidal ruthenium particle, or a colloidal iridium particle.

14. The method of one of claims 2, 12, and 13, wherein the device is in a case made of a moisture-impermeable solid material.

15. The method of one of claims 2, 12, and 13, wherein each of the different target nucleic acids N is produced by denaturing double-stranded nucleic acids.

16. The method of one of claims 2, 12, and 13, wherein each of the different target nucleic acids N is a DNA.

17. The method of claim 16, wherein each of the different target nucleic acids N is an artificially amplified nucleic acid.

18. The method of one of claims 2, 12, and 13, wherein step b) or c) is performed in a buffer containing at least one denaturant or chaotropic agent, or containing at least one denaturant or chaotropic agent and at least one inorganic salt.

* * * * *